United States Patent
Judd et al.

(10) Patent No.: US 8,883,784 B2
(45) Date of Patent: Nov. 11, 2014

(54) APOPTOSIS-INDUCING AGENTS FOR THE TREATMENT OF CANCER AND IMMUNE AND AUTOIMMUNE DISEASES

(71) Applicant: AbbVie Inc., North Chicago, IL (US)

(72) Inventors: Andrew S. Judd, Grayslake, IL (US); Andrew J. Souers, Evanston, IL (US); Zhi-Fu Tao, Vernon Hills, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/964,556

(22) Filed: Aug. 12, 2013

(65) Prior Publication Data
US 2014/0073640 A1 Mar. 13, 2014

Related U.S. Application Data

(60) Provisional application No. 61/682,370, filed on Aug. 13, 2012.

(51) Int. Cl.
| | | |
|---|---|---|
| *C07D 417/04* | (2006.01) | |
| *A61K 31/4725* | (2006.01) | |
| *A61K 31/5377* | (2006.01) | |
| *A61K 31/4985* | (2006.01) | |
| *A61K 31/5025* | (2006.01) | |
| *A61K 45/06* | (2006.01) | |
| *C07D 471/04* | (2006.01) | |
| *C07D 487/04* | (2006.01) | |
| *C07D 401/04* | (2006.01) | |
| *C07D 417/14* | (2006.01) | |
| *C07D 513/04* | (2006.01) | |

(52) U.S. Cl.
CPC .......... *C07D 417/14* (2013.01); *A61K 31/5377* (2013.01); *A61K 31/4725* (2013.01); *A61K 31/4985* (2013.01); *A61K 31/5025* (2013.01); *A61K 45/06* (2013.01); *C07D 471/04* (2013.01); *C07D 487/04* (2013.01); *C07D 401/04* (2013.01); *C07D 513/04* (2013.01)
USPC .............. 514/234.2; 514/233.8; 514/248; 514/249; 514/300; 514/301; 514/307; 544/117; 544/128; 544/236; 544/350; 546/114; 546/118; 546/144

(58) Field of Classification Search
None
See application file for complete search history.

(56) References Cited

U.S. PATENT DOCUMENTS

2013/0096120 A1    4/2013   Wang et al.

FOREIGN PATENT DOCUMENTS

| WO | 2010080503 A1 | 7/2010 |
| WO | 2011150016 A1 | 12/2011 |

OTHER PUBLICATIONS

International Searching Authority, "International Search Report for PCT/US2013/054525," (Mailed Jan. 13, 2014) (3 pp.).
International Searching Authority, "Written Opinion for PCT/US2013/054525," (Mailed Jan. 13, 2014) (9 pp.).
Rega, Michele F., et al., "Structure-Based Discovery of a New Class of Bcl-xl Antagonists," National Institute of Healthy, (2007), vol. 35, No. 4, pp. 344-353.

*Primary Examiner* — Zinna Northington Davis
(74) *Attorney, Agent, or Firm* — Jones Day

(57) ABSTRACT

Disclosed are compounds which inhibit the activity of anti-apoptotic Bcl-xL proteins, compositions containing the compounds and methods of treating diseases during which is expressed anti-apoptotic Bcl-xL protein.

14 Claims, No Drawings

APOPTOSIS-INDUCING AGENTS FOR THE TREATMENT OF CANCER AND IMMUNE AND AUTOIMMUNE DISEASES

This application claims the benefit of U.S. Provisional Application No. 61/682,370, filed Aug. 13, 2012.

FIELD OF THE INVENTION

This invention pertains to compounds which inhibit the activity of Bcl-xL anti-apoptotic proteins, compositions containing the compounds, and methods of treating diseases during which anti-apoptotic Bcl-xL proteins are expressed.

BACKGROUND OF THE INVENTION

Apoptosis is recognized as an essential biological process for tissue homeostasis of all living species. In mammals in particular, it has been shown to regulate early embryonic development. Later in life, cell death is a default mechanism by which potentially dangerous cells (e.g., cells carrying cancerous defects) are removed. Several apoptotic pathways have been uncovered, and one of the most important involves the Bcl-2 family of proteins, which are key regulators of the mitochondrial (also called "intrinsic") pathway of apoptosis. See, Danial, N. N. and Korsmeyer, S. J. *Cell* (2004) 116, 205-219. The structural homology domains BH1, BH2, BH3 and BH4 are characteristic of this family of proteins. The Bcl-2 family of proteins can be further classified into three subfamilies depending on how many of the homology domains each protein contains and on its biological activity (i.e., whether it has pro- or anti-apoptotic function).

The first subgroup contains proteins having all 4 homology domains, i.e., BH1, BH2, BH3 and BH4. Their general effect is anti-apoptotic, that is to preserve a cell from starting a cell death process. Proteins such as, for example, Bcl-2, Bcl-w, Bcl-xL, Mcl-1 and Bfl-1/A1 are members of this first subgroup. Proteins belonging to the second subgroup contain the three homology domains BH1, BH2 and BH3, and have a pro-apoptotic effect. The two main representative proteins of this second subgroup are Bax and Bak. Finally, the third subgroup is composed of proteins containing only the BH3 domain and members of this subgroup are usually referred to as "BH3-only proteins." Their biological effect on the cell is pro-apoptotic. Bim, Bid, Bad, Bik, Noxa, Hrk, Bmf, and Puma are examples of this third subfamily of proteins. The exact mechanism by which the Bcl-2 family proteins regulate cell death is still not entirely known and understanding this mechanism is an active area of research in the science community. In one hypothesis of regulation of cell death by Bcl-2 family proteins, the BH3-only proteins are further categorized as either "activator" (e.g., Bim and Bid) or "sensitizer" (e.g., Bad, Bik, Noxa, Hrk, Bmf, and Puma) proteins depending on their regulatory function.

The key to tissue homeostasis is achieving the delicate balance in the interactions among the three subgroups of protein in cells. Recent studies have tried to elucidate the mechanisms by which pro-apoptotic and anti-apoptotic subgroups of Bcl-2 family proteins interact to allow a cell to undergo programmed cell death. After receiving intra- or extracellular signals in cells, post-translational or transcriptional activation of BH3-only proteins occurs. The BH3-only proteins are the primary inducers of an apoptotic cascade that includes, as one step, the activation of the pro-apoptotic proteins Bax and Bak on the mitochondrial membrane in cells. Upon activation of Bax and/or Bak that are either already anchored to the mitochondrial membrane or migrate to this membrane, Bax and/or Bak oligomerize to result in mitochondrial outer membrane permeabilization (MOMP), the release of cytochrome C, and downstream activation of effector caspases, to ultimately result in cell apoptosis. Some researchers hypothesize that certain BH3-only proteins (e.g., Puma, Bim, Bid) are "activators" in that these proteins directly engage pro-apoptotic proteins Bax and Bak to initiate MOMP, while other BH3-only proteins (e.g., Bad, Bik and Noxa) are "sensitizers" and induce Bax and Bak oligomerization indirectly by binding anti-apoptotic proteins (e.g., Bcl-2, Bcl-xL, Bcl-w, Mcl-1) and displacing and "freeing-up" the "activator" BH3-only proteins, which subsequently bind to and activate pro-apoptotic proteins (e.g., Bax, Bak) to induce cell death. Other researchers suggest that anti-apoptotic proteins engage and sequester Bax and Bak directly and all BH3-only proteins regulates this interaction by binding to anti-apoptotic proteins (e.g., Bcl-2, Bcl-xL, Bcl-w, Mcl-1) which results in the release Bax and Bak. See, Adams, J. M. and Cory S. *Oncogene* (2007) 26, 1324-1337; Willis, S, N. et al. *Science* (2007) 315, 856-859. Although the exact interactions through which the anti- and pro-apoptotic Bcl-2 family proteins regulate apoptosis remain under debate, there is a large body of scientific evidence to show that compounds which inhibit the binding of BH3-only proteins to anti-apoptotic Bcl-2 family proteins promote apoptosis in cells.

Dysregulated apoptotic pathways have been implicated in the pathology of many significant diseases such as neurodegenerative conditions (up-regulated apoptosis), such as for example, Alzheimer's disease; and proliferative diseases (down-regulated apoptosis) such as for example, cancer, autoimmune diseases and pro-thrombotic conditions.

In one aspect, the implication that down-regulated apoptosis (and more particularly the Bcl-2 family of proteins) is involved in the onset of cancerous malignancy has revealed a novel way of targeting this still elusive disease. Research has shown, for example, the anti-apoptotic proteins, Bcl-2 and Bcl-xL, are over-expressed in many cancer cell types. See, Zhang J. Y., *Nature Reviews/Drug Discovery*, (2002) 1, 101; Kirkin, V. et al. *Biochimica et Biophysica Acta* (2004) 1644, 229-249; and Amundson, S. A. et al. *Cancer Research* (2000) 60, 6101-6110. The effect of this deregulation is the survival of altered cells which would otherwise have undergone apoptosis in normal conditions. The repetition of these defects associated with unregulated proliferation is thought to be the starting point of cancerous evolution. Additionally, research has shown that BH3-only proteins can act as tumor suppressors when expressed in diseased animals.

These findings as well as numerous others have made possible the emergence of new strategies in drug discovery for targeting cancer. If a small molecule that could mimic the effect of BH3-only proteins were able to enter the cell and overcome the anti-apoptotic protein over-expression, then it could be possible to reset the apoptotic process. This strategy can have the advantage that it can alleviate the problem of drug resistance which is usually a consequence of apoptotic deregulation (abnormal survival).

Researchers also have demonstrated that platelets also contain the necessary apoptotic machinery (e.g., Bax, Bak, Bcl-xL, Bcl-2, cytochrome c, caspase-9, caspase-3 and APAF-1) to execute programmed cell death through the intrinsic apoptotic pathway. Although circulating platelet production is a normal physiological process, a number of diseases are caused or exacerbated by excess of, or undesired activation of, platelets. The above suggests that therapeutic agents capable of inhibiting anti-apoptotic proteins in platelets and reducing the number of platelets in mammals maybe useful in treating pro-thrombotic conditions and diseases that are characterized by an excess of, or undesired activation of, platelets.

We have developed a class of small molecule BH3-only protein mimetics, i.e., ABT-737 and ABT-263, that bind strongly to a subset of anti-apoptotic Bcl-2 proteins including Bcl-2, Bcl-w and Bcl-xL, but only weakly to Mcl-1 and A1, and exhibits mechanism-based cytotoxicity. These compounds were tested in animal studies and demonstrated cytotoxic activity in certain xenograft models as single agents, as well as enhanced the effects of a number of chemotherapeutic agents on other xenograft models when used in combination. See, Tse, C. et al. *Cancer Res* (2008) 68, 3421-3428; and van Delft, M. F. et al. *Cancer Cell* (2006) 10, 389-399. These in vivo studies suggest the potential utility of inhibitors of anti-apoptotic Bcl-2 family proteins for the treatment of diseases that involve a dysregulated apoptotic pathway.

The natural expression levels of anti-apoptotic Bcl-2 family proteins members vary in different cell types. For example, in young platelets, Bcl-xL protein is highly expressed and plays an important role in regulating cell death (life span) of platelets. Also, in certain cancer cell types, the cancer cell's survival is attributed to the dysregulation of the apoptotic pathway caused by the over-expression of one or more anti-apoptotic Bcl-2 protein family members. In view of the important role for Bcl-2 family of proteins in regulating apoptosis in both cancerous and normal (i.e., non-cancerous) cells, and the recognized inter-cell type variability of Bcl-2 family protein expression, it is advantageous to have a small molecule inhibitor that selectively targets and preferably binds to one type or a subset of anti-apoptotic Bcl-2 protein (s), for example, to an anti-apoptotic Bcl-2 family member that overexpressed in a certain cancer type. Such a selective compound also may confer certain advantages in the clinical setting, by providing, for example, the flexibility to select a dosing regimen, a reduced on-target toxic effect in normal cells, among others (e.g., lymphopenia has been observed in Bcl-2 deficient mice). See, Nakayama, K. et al. *PNAS* (1994) 91, 3700-3704.

In view of the above, there is a need in the art for small molecules therapeutics that can selectively inhibit the activity of one type or a subset of anti-apoptotic Bcl-2 proteins, for example, of a Bcl-xL anti-apoptotic protein. The present invention fulfills at least this need.

SUMMARY OF THE INVENTION

One embodiment pertains to compounds and therapeutically acceptable salts, metabolites, prodrugs, salts of metabolites, and salts of prodrugs thereof, which are inhibitors of anti-apoptotic Bcl-xL proteins, the compounds having Formula (I)

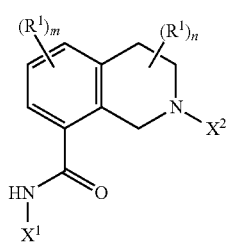

Formula (I)

wherein $X^1$ is heteroaryl; optionally substituted with one, two, three, or four $R^4$;

$X^2$ is

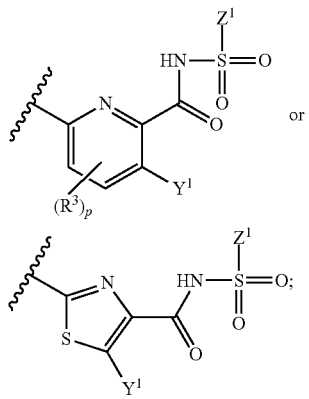

$Y^1$ is hydrogen, $(CH_2)_tR^5$, $(CH_2)_tOR^5$, $(CH_2)_tNHR^5$, $(CH_2)_tN(R^5)_2$, or $(CH_2)_tSR^5$;

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^6R^7$, $OR^6$, CN, $NO_2$, halogen, $C(O)OR^6$, $C(O)NR^6R^7$, $NR^6C(O)R^7$, $NR^6S(O)_2R^8$, $NR^6S(O)R^8$, $S(O)_2R^8$, $S(O)R^8$ and $R^8$;

$R^5$ is aryl or heterocyclyl; optionally substituted with one, two, three, or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $CO(O)H$, $C(O)H$, $OH$, $CN$, $N_3$, $NO_2$, $F$, $Cl$, $Br$ and $I$;

$R^6$ and $R^7$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^8$, at each occurrence, is independently selected from the group consisting of $C_{1-4}$ alkyl, $C_{2-4}$ alkenyl, $C_{2-4}$ alkynyl and $C_{1-4}$ haloalkyl;

$R^6$ and $R^7$, or $R^6$ and $R^8$, at each occurrence, together with the atom to which each is attached, are optionally combined to form a heterocyclyl;

$R^9$, at each occurrence, is independently selected from the group consisting of $C_{1-6}$ alkyl, $C_{2-6}$ alkenyl, $C_{2-6}$ alkynyl, and $C_{1-6}$ haloalkyl;

t is 1, 2, or 3;
m is 0, 1, 2, or 3;
n is 0, 1, 2, 3, 4, 5, or 6;
p is 0, 1, or 2;

$Z^1$ is aryl, heteroaryl, cycloalkyl, cycloalkenyl, heterocycloalkyl, or heterocycloalkenyl;

wherein $Z^1$ is unsubstituted or substituted with one or two or three or four or five independently selected $R^{10}$, $OR^{10}$, $SR^{10}$, $S(O)R^{10}$, $SO_2R^{10}$, $C(O)R^{10}$, $C(O)OR^{19}$, $OC(O)R^{10}$, $NHR^{10}$, $N(R^{10})_2$, $C(N)C(O)R^{10}$, $C(O)NHR^{10}$, $C(O)N(R^{10})_2$, $C(O)NHOH$, $C(O)NHOR^{10}$, $C(O)NHSO_2R^{10}$, $NHC(O)R^{10}$, $NR^{10}C(O)R^{10}$, $NHC(O)OR^{19}$, $NR^{10}C(O)OR^{10}$, $NR^{10}C(O)NHR^{10}$, $NR^{10}C(O)N(R^{10})_2$, $NHC(O)NH_2$, $NHC(O)NHR^{10}$, $NHC(O)N(R^{10})_2$, $SO_2NH_2$, $SO_2NHR^{10}$, $SO_2N(R^{19})_2$, $NHS(O)R^{10}$, $NHSO_2R^{10}$, $NR^{10}SO_2R^{10}$, $NHSO_2NHR^{10}$, $N(CH_3)SO_2N(CH_3)R^{10}$, (O), $NH_2$, $NO_2$, $N_3$, OH, F, Cl, Br, I, CN, $CF_3$, $OCF_3$, $CF_2CF_3$, $OCF_2CF_3$, $C(O)H$, $C(O)OH$, $C(N)NH_2$, $C(N)NHR^{10}$, $C(N)N(R^{10})_2$, CNOH, $CNOCH_3$, or $C(O)NH_2$ substituents;

$R^{10}$ is $R^{11}$, $R^{12}$, $R^{13}$ or $R^{14}$;

$R^{11}$ is aryl;

$R^{12}$ is heteroaryl;

$R^{13}$ is cycloalkyl, cycloalkenyl, cycloalkynyl, heterocycloalkyl or heterocycloalkenyl;

$R^{14}$ is alkyl, alkenyl or alkynyl, each of which is unsubstituted or substituted with one or two or three independently selected $R^{15D}$, $NC(R^{15A})(R^{15B})$, $R^{15}$, $OR^{15}$, $SR^{15}$, $S(O)R^{15}$, $SO_2R^{15}$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NHC(O)OR^{15}$, $SO_2NH_2$, $SO_2NHR^{15}$, $SO_2N(R^{15})_2$, $NHC(O)NH_2$, $NHC(O)NHR^{15}$, $NHC(O)CH(CH_3)NHC(O)CH(CH_3)NH_2$, $NHC(O)CH(CH_3)NHC(O)CH(CH_3)NHR^{15}$, OH, (O), $C(O)OH$, $N_3$, CN, $NH_2$, $CF_3$, $CF_2CF_3$, F, Cl, Br or I substituents;

$R^{15A}$ and $R^{15B}$ are independently selected alkyl or, together with the N to which they are attached, $R^{15C}$;

$R^{15C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^{15D}$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{15}$ is $R^{16}$, $R^{17}$, $R^{18}$ or $R^{19}$;

$R^{16}$ is aryl;

$R^{17}$ is heteroaryl;

$R^{18}$ is cycloalkyl, cycloalkenyl, heterocycloalkyl, or heterocycloalkenyl; and $R^{19}$ is alkyl. In another embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (I), $X^1$ is

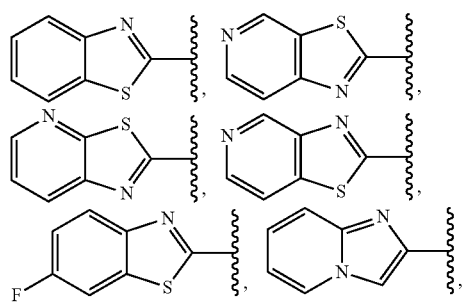

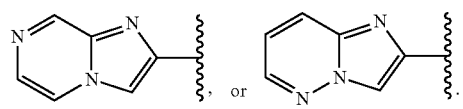

In another embodiment of Formula (I), $X^1$ is

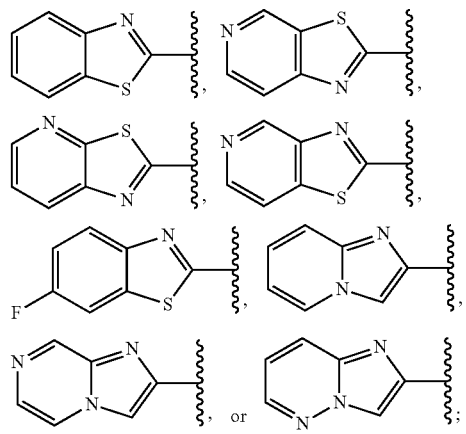

and $X^2$ is

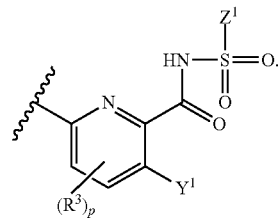

In another embodiment of Formula (I), $X^1$ is

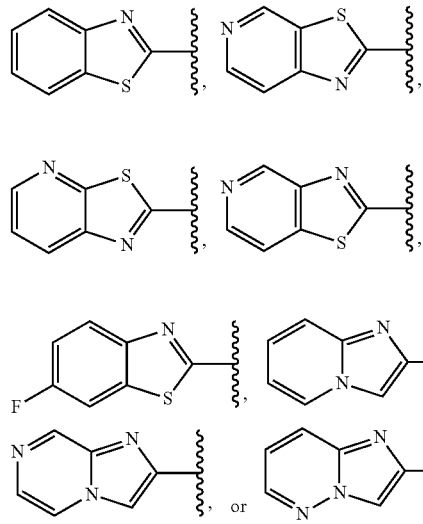

and $X^2$ is
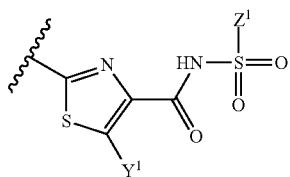
In another embodiment of Formula (I), $X^1$ is
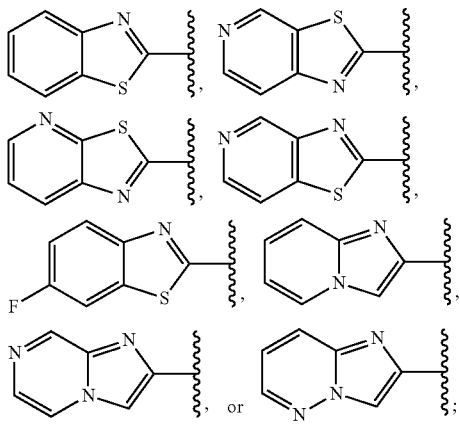
$X^2$ is
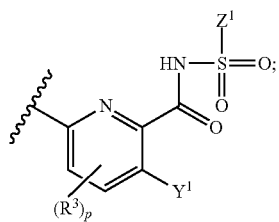
and $Y^1$ is hydrogen. In another embodiment of Formula (I), $X^1$ is
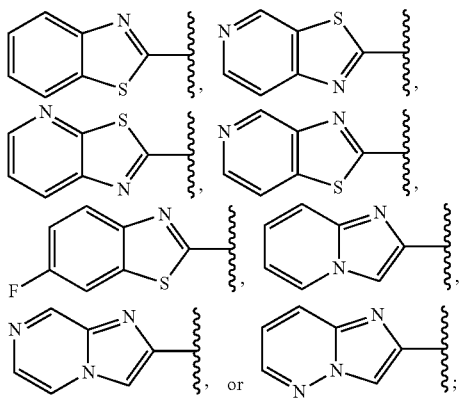
$X^2$ is
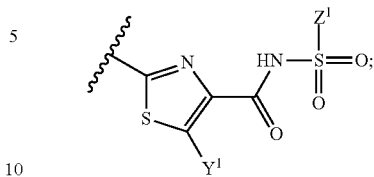
and $Y^1$ is hydrogen. In another embodiment of Formula (I), $X^1$ is
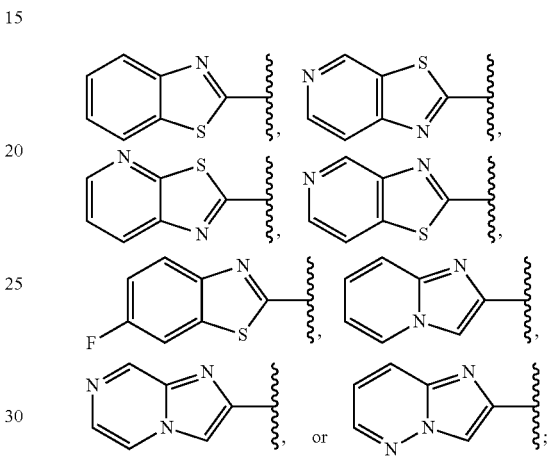
$X^2$ is
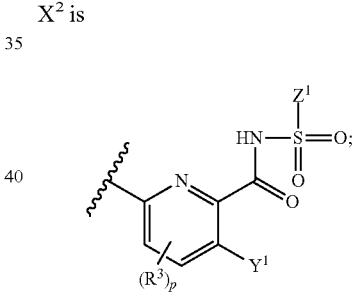
$Y^1$ is $(CH_2)_t R^5$; $R^5$ is aryl; and t is 1, 2, or 3. In another embodiment of Formula (I), $X^1$ is
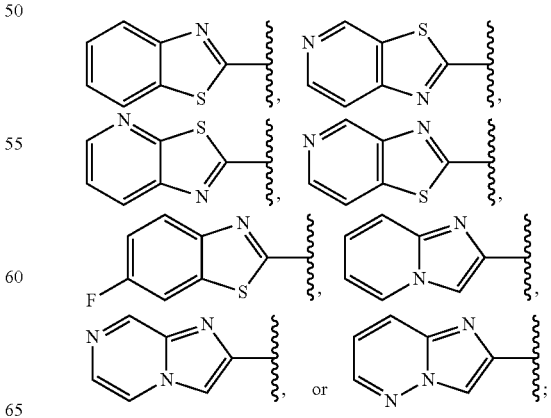

$X^2$ is

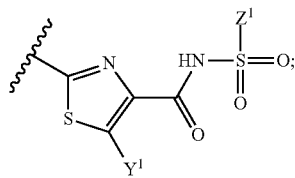

$Y^1$ is $(CH_2)_tR^5$; $R^5$ is aryl; and t is 1, 2, or 3. In another embodiment of Formula (I), $Z^1$ is unsubstituted or substituted phenyl. In another embodiment of Formula (I), $Z^1$ is phenyl; and $Z^1$ is substituted with $NHR^{10}$ and $SO_2CF_3$, $SO_2CF_2Cl$, $CF_3$, $NO_2$, or F.

Still another embodiment pertains to a compound having Formula (I), selected from the group consisting of N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(6-{[(4-{[(2R)-4-(morpholin-4-yl)-1-(phenyl sulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide;

N-(1,3-benzothiazol-2-yl)-2-(4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(5-benzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(5-benzyl-4-{[(4-{[3-(dimethylamino)propyl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-[(trifluoromethyl)sulfonyl]phenyl)sulfonyl]carbamoyl}-5-(2-phenylethyl)-1,3-thiazol-2-yl]-1,2,3,4-tetrahydroisoquinoline-8-carboxamide;

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-nitrophenyl)sulfonyl]carbamoyl}-5-(2-phenylethyl)-1,3-thiazol-2-yl]-1,2,3,4-tetrahydroisoquinoline-8-carboxamide;

N-(1,3-benzothiazol-2-yl)-2-(4-{[(4-{[(2R)-4-hydroxy-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

N-(imidazo[1,2-a]pyridin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-a]pyridin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(imidazo[1,2-a]pyrazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-a]pyrazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(imidazo[1,2-b]pyridazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-b]pyridazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(6-fluoro-1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(6-fluoro-1,3-benzothiazol-2-yl)-2-(4-{[(4-{[(2R)-4-(morpholin-4-yl)-1-(phenylsulfanyl)butan-2-yl]amino}-

3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(1,3-benzothiazol-2-yl)-2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]

amino}phenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-b]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-c]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[4,5-c]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-a]pyridin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(imidazo[1,2-a]pyrazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-a]pyrazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(imidazo[1,2-b]pyridazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-b]pyridazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(6-fluoro-1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(6-fluoro-1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]

carbamoyl}pyridin-2-yl)-N-(imidazo[1,2-a]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

N-(6-fluoro-1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(6-fluoro-1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

N-(1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-b]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-c]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[4,5-c]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-a]pyridin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(imidazo[1,2-a]pyrazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-a]pyrazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(imidazo[1,2-b]pyridazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-b]pyridazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(6-fluoro-1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(6-fluoro-1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(1,3-benzothiazol-2-yl)-2-(6-{[(4-{[(2R)-4-(dimethylamino)-1-phenoxybutan-2-yl]amino}-3-nitrophenyl)sulfonyl]carbamoyl}pyridin-2-yl)-1,2,3,4-tetrahydroisoquinoline-8-carboxamide;

N-(1,3-benzothiazol-2-yl)-2-(4-{[(4-{[(2R)-4-(dimethylamino)-1-phenoxybutan-2-yl]amino}-3-nitrophenyl)sulfonyl]carbamoyl}-1,3-thiazol-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-1,2,3,4-tetrahydroisoquinoline-8-carboxamide;

N-(1,3-benzothiazol-2-yl)-2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; and therapeutically acceptable salts thereof.

Still another embodiment pertains to a compound having Formula (I), selected from the group consisting of N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(6-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide;

N-(1,3-benzothiazol-2-yl)-2-(4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-(5-benzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-(5-benzyl-4-{[(4-{[3-(dimethylamino)propyl]amino}-3-nitrophenyl)sulfonyl]carbamoyl}-1,3-thiazol-2-yl)-1,2,3,4-tetrahydroisoquinoline-8-carboxamide;
N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;
N-(1,3-benzothiazol-2-yl)-2-[4-{[(4-{[3-(dimethylamino)propyl]amino}-3-[(trifluoromethyl)sulfonyl]phenyl)sulfonyl]carbamoyl}-5-(2-phenylethyl)-1,3-thiazol-2-yl]-1,2,3,4-tetrahydroisoquinoline-8-carboxamide;
N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-[4-{[(4-{[3-(dimethylamino)propyl]amino}-3-nitrophenyl)sulfonyl]carbamoyl}-5-(2-phenylethyl)-1,3-thiazol-2-yl]-1,2,3,4-tetrahydroisoquinoline-8-carboxamide;
N-(1,3-benzothiazol-2-yl)-2-(4-{[(4-{[(2R)-4-hydroxy-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide;
and therapeutically acceptable salts thereof.

Another embodiment pertains to a composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said composition comprising an excipient and a therapeutically effective amount of a compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient a therapeutically effective amount of a compound of Formula (I).

Another embodiment pertains to a method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said method comprising administering to the patient therapeutically effective amount of the compound of Formula (I) and a therapeutically effective amount of one additional therapeutic agent or more than one additional therapeutic agent.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, cyclooxtanyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. Examples of spirocyclic carbocyclyls include spiropentanyl, spiro[3.5]nonanyl, and spiro[2.5]octanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl (tricyclo[3.3.1.1$^{3,7}$]decanyl). In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, cyclohexyl, cycloheptanyl, and cyclooctanyl. A cycloalkyl may alternatively be polycyclic or contain more than one ring. Examples of polycyclic cycloalkyls include bridged, fused, and spirocyclic carbocyclyls. Examples of bridged cycloalkyls include adamantanyl (tricyclo[3.3.1.1$^{3,7}$]decanyl), and bicyclo[3.1.1]heptanyl.

The term "$C_x$-$C_y$ cycloalkyl" means a cycloalkyl ring system containing from x to y carbon atoms. For example "$C_3$-$C_7$ cycloalkyl" means a cycloalkyl ring system containing from 3 to 7 carbon atoms.

The term "cycloalkenyl" (alone or in combination with another term(s)) means a partially saturated cyclic hydrocarbyl substituent containing from 3 to 14 carbon ring atoms. A cycloalkenyl may be a single carbon ring, which typically contains from 3 to 8 carbon ring atoms and more typically from 4 to 6 ring atoms. Examples of single-ring cycloalkenyls include cyclopentenyl, and cyclohexenyl. A cycloalkenyl may alternatively be polycyclic or contain more than one ring. Examples of polycyclic cycloalkenyls include bridged, fused, and spirocyclic carbocyclyls. Examples of bridged cycloalkenyls include bicyclo[2.2.1]hept-2-enyl.

The term "$C_x$-$C_y$ cycloalkenyl" means a cycloalkenyl ring system containing from x to y carbon atoms. For example "$C_4$-$C_7$ cycloalkenyl" means a cycloalkenyl ring system containing from 4 to 7 carbon atoms.

The term "aryl" (alone or in combination with another term(s)) means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be unsaturated while the remaining ring(s) may be saturated, partially saturated or unsaturated. Examples of aryls include phenyl, naphthalenyl, indenyl, indanyl, and tetrahydronapthyl.

The term "heteroarylene" means a divalent heteroarene.

The term "arylene" means a divalent arene.

The term "phenylene" means a divalent benzene.

In some instances, the number of carbon atoms in a substituent (e.g., alkyl, alkenyl, alkynyl, cycloalkyl, heterocyclyl, heteroaryl, and aryl) is indicated by the prefix "$C_x$-$C_y$-", wherein x is the minimum and y is the maximum number of carbon atoms. Thus, for example, "$C_1$-$C_6$-alkyl" refers to an alkyl containing from 1 to 6 carbon atoms. Illustrating further, "$C_3$-$C_8$-cycloalkyl" means a saturated hydrocarbyl ring containing from 3 to 8 carbon ring atoms.

The term "$C_{x-y}$ branched chain alkyl" means a saturated hydrocarbyl substituent containing from x to y carbons wherein attachment occurs through a dialkyl trivalent- or trialkyl tetravalent-carbon radical. Examples of such substituents include isopentanyl (pentan-3-yl), neopentanyl (2,2-dimethylpropan-2-yl), heptan-4-yl, and 2,6-dimethylheptan-4-yl.

The term, "$C_{3-11}$ branched chain alkyl" means a saturated hydrocarbyl substituent containing from 3 to 11 carbons wherein attachment occurs through a dialkyl trivalent- or trialkyl tetravalent-carbon radical.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "hydroxyalkyl" (alone or in combination with another term(s)) means alkyl-OH.

The term "alkylamino" (alone or in combination with another term(s)) means alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means replacement by a sulfur radical, i.e. a thiaether substituent means an ether substituent wherein a divalent sulfur atom is in the place of the ether oxygen atom. Such a substituent may be depicted as —S—. For example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, tetrahydropyranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), 1,4-dioxanyl, dioxothiomorpholinyl, oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, diazepinyl, pyridonyl (including pyrid-2(1H)-onyl and pyrid-4(1H)-onyl), furan-2(5H)-onyl, pyrimidonyl (including pyramid-2(1H)- onyl and pyramid-4(3H)-onyl), oxazol-2(3H)-onyl, 1H-imidazol-2(3H)-onyl, pyridazin-3(2H)-onyl, and pyrazin-2(1H)-onyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. Examples of bridged heterocyclyls include 2-oxatricyclo[3.3.1.1$^{3,7}$]decane. In a fused-ring heterocyclyl, two or more rings may be fused together, such that two rings share one common bond. Examples of fused ring heterocyclyls containing two or three rings include imidazopyrazinyl (including imidazo[1,2-a]pyrazinyl), imidazopyridinyl (including imidazo[1,2-a]pyridinyl), imidazopyridazinyl (including imidazo[1,2-b]pyridazinyl), thiazolopyridinyl (including thiazolo[5,4-c]pyridinyl, thiazolo[5,4-b]pyridinyl, thiazolo[4,5-b]pyridinyl, and thiazolo[4,5-c]pyridinyl), indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as dihydrochromenyl, tetrahydroisoquinolinyl, indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), benzo[d]thiazolyl, and benzisoxazinyl (including 1,2-benzisoxazinyl or 1,4-benzisoxazinyl).

The term "heterocycloalkyl" (alone or in combination with another term(s)) means a saturated heterocyclyl.

The term "$C_x$-$C_y$ heterocycloalkyl" means a heterocycloalkyl ring system containing from x to y ring atoms. For example "$C_3$-$C_7$ heterocycloalkyl" means a heterocycloalkyl ring system containing 3 to 7 ring atoms.

The term "heterocycloalkenyl" (alone or in combination with another term(s)) means a partially saturated heterocyclyl.

The term "$C_x$-$C_y$ heterocycloalkenyl" means a heterocycloalkenyl ring system containing from x to y ring atoms. For example "$C_3$-$C_7$ heterocycloalkenyl" means a heterocycloalkenyl ring system containing from 3 to 7 ring atoms.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryls include 6-membered ring substituents such as pyridyl, pyrazyl, pyrimidinyl, pyridazinyl, and 1,3,5-, 1,2,4- or 1,2,3-triazinyl; 5-membered ring substituents such as triazolyl, pyrrolyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as imidazopyrazinyl (including imidazo[1,2-a]pyrazinyl) imidazopyridinyl (including imidazo[1,2-a]pyridinyl), imidazopyridazinyl (including imidazo[1,2-b]pyridazinyl), thiazolopyridinyl (including thiazolo[5,4-c]pyridinyl, thiazolo[5,4-b]pyridinyl, thiazolo[4,5-b]pyridinyl, and thiazolo[4,5-c]pyridinyl), benzo[d]thiazolyl, benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

The term "$C_x$-$C_y$ heteroaryl" means a heteroaryl ring system containing from x to y ring atoms. For example "$C_5$-$C_6$ heteroaryl" means a heteroaryl ring system containing from 5 to 6 ring atoms.

The term "heteroarylene" means a divalent heteroaryl group.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

The term "NH protecting group," as used herein, means trichloroethoxycarbonyl, tribromoethoxycarbonyl, benzyloxycarbonyl, para-nitrobenzylcarbonyl, ortho-bromobenzyloxycarbonyl, chloroacetyl, dichloroacetyl, trichloroacetyl, trifluoroacetyl, phenylacetyl, formyl, acetyl, benzoyl, tert-amyloxycarbonyl, tert-butoxycarbonyl, para-methoxybenzyloxycarbonyl, 3,4-dimethoxybenzyl-oxycarbonyl, 4-(phenylazo)benzyloxycarbonyl, 2-furfuryl-oxycarbonyl, diphenylmethoxycarbonyl, 1,1-dimethylpropoxy-carbonyl, isopropoxycarbonyl, phthaloyl, succinyl, alanyl, leucyl, 1-adamantyloxycarbonyl, 8-quinolyloxycarbonyl, benzyl, diphenylmethyl, triphenylmethyl, 2-nitrophenylthio, methanesulfonyl, para-toluenesulfonyl, N,N-dimethylaminomethylene, benzylidene, 2-hydroxybenzylidene, 2-hydroxy-5-chlorobenzylidene, 2-hydroxy-1-naphthyl-methylene, 3-hydroxy-4-pyridylmethylene, cyclohexylidene, 2-ethoxycarbonylcyclohexylidene, 2-ethoxycarbonylcyclopentylidene, 2-acetylcyclohexylidene, 3,3-dimethyl-5-oxycyclohexylidene, diphenylphosphoryl, dibenzylphosphoryl, 5-methyl-2-oxo-2H-1,3-dioxol-4-yl-methyl, trimethylsilyl, triethylsilyl, and triphenylsilyl.

The term "C(O)OH protecting group," as used herein, means methyl, ethyl, n-propyl, isopropyl, 1,1-dimethylpropyl, n-butyl, tert-butyl, phenyl, naphthyl, benzyl, diphenylmethyl, triphenylmethyl, para-nitrobenzyl, para-methoxybenzyl, bis(para-methoxyphenyl)methyl, acetylmethyl, benzoylmethyl, para-nitrobenzoylmethyl, para-bromobenzoylmethyl, para-methanesulfonylbenzoylmethyl, 2-tetrahydropyranyl 2-tetrahydrofuranyl, 2,2,2-trichloroethyl, 2-(trimethylsilyl)ethyl, acetoxymethyl, propionyloxymethyl, pivaloyloxymethyl, phthalimidomethyl, succinimidomethyl, cyclopropyl, cyclobutyl, cyclopentyl, cyclohexyl, methoxymethyl, methoxyethoxymethyl, 2-(trimethylsilyl)ethoxymethyl, benzyloxymethyl, methylthiomethyl, 2-methylthioethyl, phenylthiomethyl, 1,1-dimethyl-2-propenyl, 3-methyl-3-butenyl, allyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

The term "OH or SH protecting group," as used herein, means benzyloxycarbonyl, 4-nitrobenzyloxycarbonyl, 4-bromobenzyloxycarbonyl, 4-methoxybenzyloxycarbonyl, 3,4-dimethoxybenzyloxycarbonyl, methoxycarbonyl, ethoxycarbonyl, tert-butoxycarbonyl, 1,1-dimethylpropoxycarbonyl, isopropoxycarbonyl, isobutyloxycarbonyl, diphenylmethoxycarbonyl, 2,2,2-trichloroethoxycarbonyl, 2,2,2-tribromoethoxycarbonyl, 2-(trimethylsilyl)ethoxycarbonyl, 2-(phenylsulfonyl)ethoxycarbonyl, 2-(triphenylphosphonio)ethoxycarbonyl, 2-furfuryloxycarbonyl, 1-adamantyloxycarbonyl, vinyloxycarbonyl, allyloxycarbonyl, S-benzylthiocarbonyl, 4-ethoxy-1-naphthyloxycarbonyl, 8-quinolyloxycarbonyl, acetyl, formyl, chloroacetyl, dichloroacetyl, trichloroacetyl, trifluoroacetyl, methoxyacetyl, phenoxyacetyl, pivaloyl, benzoyl, methyl, tert-butyl, 2,2,2-trichloroethyl, 2-trimethylsilylethyl, 1,1-dimethyl-2-propenyl, 3-methyl-3-butenyl, allyl, benzyl (phenylmethyl), para-methoxybenzyl, 3,4-dimethoxybenzyl, diphenylmethyl, triphenylmethyl, tetrahydrofuryl, tetrahydropyranyl, tetrahydrothiopyranyl, methoxymethyl, methylthiomethyl, benzyloxymethyl, 2-methoxyethoxymethyl, 2,2,2-trichloroethoxymethyl, 2-(trimethylsilyl)ethoxymethyl, 1-ethoxyethyl, methanesulfonyl, para-toluenesulfonyl, trimethylsilyl, triethylsilyl, triisopropylsilyl, diethylisopropylsilyl, tert-butyldimethylsilyl, tert-butyldiphenylsilyl, diphenylmethylsilyl, and tert-butylmethoxyphenylsilyl.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers. Substituents around a cycloalkyl or heterocycloalkyl are sometimes designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^{2}H$, $^{3}H$, $^{13}C$, $^{14}C$, $^{15}N$, $^{18}O$, $^{32}P$, $^{35}S$, $^{18}F$, $^{36}Cl$ and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7511013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of Bcl-xL inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., *Advances in*

*Drug Research Vol.* 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to Bcl-xL activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Suitable groups for $X^1$, $X^2$, $R^1$, $R^2$, m, and n in compounds of Formula (I) are independently selected. The described embodiments of the present invention may be combined. Such combination is contemplated and within the scope of the present invention. For example, it is contemplated that embodiments for any of $X^1$, $X^2$, $R^1$, $R^2$, m, and n can be combined with embodiments defined for any other of $X^1$, $X^2$, $R^1$, $R^2$, m, and n.

One embodiment pertains to compounds and therapeutically acceptable salts, metabolites, prodrugs, salts of metabolites, and salts of prodrugs thereof, which are inhibitors of anti-apoptotic Bcl-xL proteins, the compounds having Formula (I)

Formula (I)

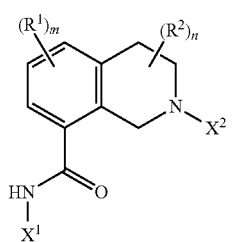

wherein $X^1$ is heteroaryl; optionally substituted with one, two, three, or four $R^4$;

$X^2$ is

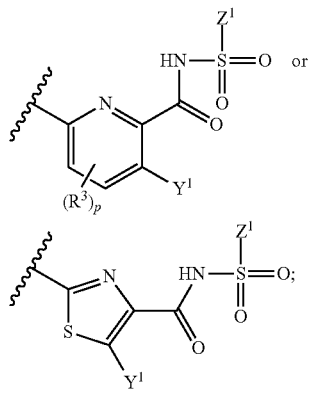

$Y^1$ is hydrogen, $(CH_2)_tR^5$, $(CH_2)_tOR^5$, $(CH_2)_tNHR^5$, $(CH_2)_tN(R^5)_2$, or $(CH_2)_tSR^5$;

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^6R^7$, $OR^6$, CN, $NO_2$, halogen, $C(O)OR^6$, $C(O)NR^6R^7$, $NR^6C(O)R^7$, $NR^6S(O)_2R^8$, $NR^6S(O)R^8$, $S(O)_2R^8$, $S(O)R^8$ and $R^8$;

$R^5$ is aryl or heterocyclyl; optionally substituted with one, two, three, or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $CO(O)H$, $C(O)H$, $OH$, $CN$, $N_3$, $NO_2$, F, Cl, Br and I;

$R^6$ and $R^7$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^8$, at each occurrence, is independently selected from the group consisting of $C_{1-4}$ alkyl, $C_{2-4}$ alkenyl, $C_{2-4}$ alkynyl and $C_{1-4}$ haloalkyl;

$R^6$ and $R^7$, or $R^6$ and $R^8$, at each occurrence, together with the atom to which each is attached, are optionally combined to form a heterocyclyl;

$R^9$, at each occurrence, is independently selected from the group consisting of $C_{1-6}$ alkyl, $C_{2-6}$ alkenyl, $C_{2-6}$ alkynyl, and $C_{1-6}$ haloalkyl;

t is 1, 2, or 3;

m is 0, 1, 2, or 3;

n is 0, 1, 2, 3, 4, 5, or 6;

p is 0, 1, or 2;

$Z^1$ is aryl, heteroaryl, cycloalkyl, cycloalkenyl, heterocycloalkyl, or heterocycloalkenyl;

wherein $Z^1$ is unsubstituted or substituted with one or two or three or four or five independently selected $R^{10}$, $OR^{10}$, $SR^{10}$, $S(O)R^{10}$, $SO_2R^{10}$, $C(O)R^{10}$, $C(O)OR^{10}$, $OC(O)R^{10}$, $NHR^{10}$, $N(R^{10})_2$, $C(N)C(O)R^{10}$, $C(O)NHR^{10}$, $C(O)N(R^{10})_2$, $C(O)NHOH$, $C(O)NHOR^{10}$, $C(O)NHSO_2R^{10}$, $NHC(O)R^{10}$, $NR^{10}C(O)R^{10}$, $NHC(O)OR^{10}$, $NR^{10}C(O)OR^{10}$, $NR^{10}C(O)NHR^{10}$, $NR^{10}C(O)N(R^{10})_2$, $NHC(O)NH_2$, $NHC(O)NHR^{10}$, $NHC(O)N(R^{10})_2$, $SO_2NH_2$, $SO_2NHR^{10}$, $SO_2N(R^{10})_2$, $NHS(O)R^{10}$, $NHSO_2R^{10}$, $NR^{10}SO_2R^{10}$, $NHSO_2NHR^{10}$, $N(CH_3)SO_2N(CH_3)R^{10}$, $(O)$, $NH_2$, $NO_2$, $N_3$, $OH$, $F$, $Cl$, $Br$, $I$, $CN$, $CF_3$, $OCF_3$, $CF_2CF_3$, $OCF_2CF_3$, $C(O)H$, $C(O)OH$, $C(N)NH_2$, $C(N)NHR^{10}$, $C(N)N(R^{10})_2$, $CNOH$, $CNOCH_3$, or $C(O)NH_2$ substituents;

$R^{10}$ is $R^{11}$, $R^{12}$, $R^{13}$ or $R^{14}$;

$R^{11}$ is aryl;

$R^{12}$ is heteroaryl;

$R^{13}$ is cycloalkyl, cycloalkenyl, cycloalkynyl, heterocycloalkyl or heterocycloalkenyl;

$R^{14}$ is alkyl, alkenyl or alkynyl, each of which is unsubstituted or substituted with one or two or three independently selected $R^{15D}$, $NC(R^{15A})(R^{15B})$, $R^{15}$, $OR^{15}$, $SR^{15}$, $S(O)R^{15}$, $SO_2R^{15}$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NHC(O)OR^{15}$, $SO_2NH_2$, $SO_2NHR^{15}$, $SO_2N(R^{15})_2$, $NHC(O)NH_2$, $NHC(O)NHR^{15}$, $NHC(O)CH(CH_3)NHC(O)CH(CH_3)NH_2$, $NHC(O)CH(CH_3)NHC(O)CH(CH_3)NHR^{15}$, $OH$, $(O)$, $C(O)OH$, $N_3$, $CN$, $NH_2$, $CF_3$, $CF_2CF_3$, $F$, $Cl$, $Br$ or $I$ substituents;

$R^{15A}$ and $R^{15B}$ are independently selected alkyl or, together with the N to which they are attached, $R^{15C}$;

$R^{15C}$ is aziridin-1-yl, azetidin-1-yl, pyrrolidin-1-yl or piperidin-1-yl, each having one $CH_2$ moiety unreplaced or replaced with O, $C(O)$, $CNOH$, $CNOCH_3$, S, $S(O)$, $SO_2$ or NH;

$R^{15D}$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{15}$ is $R^{16}$, $R^{17}$, $R^{18}$ or $R^{19}$;

$R^{16}$ is aryl;

$R^{17}$ is heteroaryl;

$R^{18}$ is cycloalkyl, cycloalkenyl, heterocycloalkyl, or heterocycloalkenyl;

$R^{19}$ is alkyl, alkenyl or alkynyl, each of which is unsubstituted or substituted with one or two or three independently selected $R^{20}$, $OR^{20}$, $SR^{20}$, $S(O)R^{20}$, $SO_2R^{29}$, $C(O)R^{20}$, $CO(O)R^{20}$, $OC(O)R^{20}$, $OC(O)OR^{20}$, $NH_2$, $NHR^{20}$, $N(R^{20})_2$, $NHC(O)R^{20}$, $NR^{20}C(O)R^{20}$, $NHS(O)_2R^{20}$, $NR^{20}S(O)_2R^{20}$, $NHC(O)OR^{20}$, $NR^{20}C(O)OR^{20}$, $NHC(O)NH_2$, $NHC(O)NHR^{20}$, $NHC(O)N(R^{20})_2$, $NR^{20}C(O)NHR^{20}$, $NR^{20}C(O)N(R^{20})_2$, $C(O)NH_2$, $C(O)NHR^{20}$, $C(O)N(R^{20})_2$, $C(O)NHOH$, $C(O)NHOR^{20}$, $C(O)NHSO_2R^{20}$, $C(O)NR^{20}SO_2R^{20}$, $SO_2NH_2$, $SO_2NHR^{20}$, $SO_2N(R^{20})_2$, $C(O)H$, $C(O)OH$, $C(N)NH_2$, $C(N)NHR^{20}$, $C(N)N(R^{20})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{20}$ is $R^{21}$, $R^{22}$, $R^{23}$ or $R^{24}$;

$R^{21}$ is aryl;

$R^{22}$ is heteroaryl;

$R^{23}$ is cycloalkane, cycloalkene, heterocycloalkane or heterocycloalkene;

$R^{24}$ is alkyl, alkenyl or alkynyl;

wherein the cyclic moieties represented by $R^{11}$, $R^{12}$, $R^{13}$, $R^{15C}$, $R^{15D}$, $R^{16}$, $R^{17}$, $R^{18}$, $R^{21}$, $R^{22}$, and $R^{23}$ are independently unsubstituted, further unsubstituted, substituted or further substituted with one or more independently selected $R^{25}$, $OR^{25}$, $SR^{25}$, $S(O)R^{25}$, $SO_2R^{25}$, $C(O)R^{25}$, $CO(O)R^{25}$, $OC(O)R^{25}$, $OC(O)OR^{25}$, $NH_2$, $NHR^{25}$, $N(R^{25})_2$, $NHC(O)R^{25}$, $NR^{25}C(O)R^{25}$, $NHS(O)_2R^{25}$, $NR^{25}S(O)_2R^{25}$, $NHC(O)OR^{25}$, $NR^{25}C(O)OR^{25}$, $NHC(O)NH_2$, $NHC(O)NHR^{25}$, $NHC(O)N(R^{25})_2$, $NR^{25}C(O)NHR^{25}$, $NR^{25}C(O)N(R^{25})_2$, $C(O)NH_2$, $C(O)NHR^{25}$, $C(O)N(R^{25})_2$, $C(O)NHOH$, $C(O)NHOR^{25}$, $C(O)NHSO_2R^{25}$, $C(O)NR^{25}SO_2R^{25}$, $SO_2NH_2$, $SO_2NHR^{25}$, $SO_2N(R^{25})_2$, $C(O)H$, $C(O)OH$, $C(N)NH_2$, $C(N)NHR^{25}$, $C(N)N(R^{25})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{25}$ is $R^{26}$, $R^{27}$, $R^{28}$ or $R^{29}$;

$R^{26}$ is aryl;

$R^{27}$ is heteroaryl;

$R^{28}$ is cycloalkyl, cycloalkenyl, heterocycloalkyl or heterocycloalkenyl;

$R^{29}$ is alkyl, alkenyl, or alkynyl, each of which is unsubstituted or substituted with one or two or three independently selected $R^{30}$, $OR^{30}$, $SR^{30}$, $S(O)R^{30}$, $SO_2R^{39}$, $C(O)R^{30}$, $CO(O)R^{30}$, $OC(O)R^{30}$, $OC(O)OR^{30}$, $NH_2$, $NHR^{30}$, $N(R^{30})_2$, $NHC(O)R^{30}$, $NR^{30}C(O)R^{30}$, $NHS(O)_2R^{30}$, $NR^{30}S(O)_2R^{30}$, $NHC(O)OR^{30}$, $NR^{30}C(O)OR^{30}$, $NHC(O)NH_2$, $NHC(O)NHR^{30}$, $NHC(O)N(R^{30})_2$, $NR^{30}C(O)NHR^{30}$, $NR^{30}C(O)N(R^{30})_2$, $C(O)NH_2$, $C(O)NHR^{30}$, $C(O)N(R^{30})_2$, $C(O)NHOH$, $C(O)NHOR^{30}$, $C(O)NHSO_2R^{30}$, $C(O)NR^{30}SO_2R^{30}$, $SO_2NH_2$, $SO_2NHR^{30}$, $SO_2N(R^{30})_2$, $C(O)H$, $C(O)OH$, $C(N)NH_2$, $C(N)NHR^{30}$, $C(N)N(R^{30})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{30}$ is $R^{31}$, $R^{32}$, $R^{33}$ or $R^{34}$;

$R^{31}$ is aryl;

$R^{32}$ is heteroaryl;

$R^{33}$ is cycloalkyl, cycloalkenyl, heterocycloalkyl or heterocycloalkenyl;

$R^{34}$ is alkyl, alkenyl, or alkenyl, each of which is unsubstituted or substituted with one or two or three independently selected $R^{35}$, $OR^{35}$, $SR^{35}$, $S(O)R^{35}$, $SO_2R^{35}$, $C(O)R^{35}$, $CO(O)R^{35}$, $OC(O)R^{35}$, $OC(O)OR^{35}$, $NH_2$, $NHR^{35}$, $N(R^{35})_2$, $NHC(O)R^{35}$, $NR^{35}C(O)R^{35}$, $NHS(O)_2R^{35}$, $NR^{35}S(O)_2R^{35}$, $NHC(O)OR^{35}$, $NR^{35}C(O)OR^{35}$, $NHC(O)NH_2$, $NHC(O)NHR^{35}$, $NHC(O)N(R^{35})_2$, $NR^{35}C(O)NHR^{35}$, $NR^{35}C(O)N(R^{35})_2$, $C(O)NH_2$, $C(O)NHR^{35}$, $C(O)N(R^{35})_2$, $C(O)NHOH$, $C(O)NHOR^{35}$, $C(O)NHSO_2R^{35}$, $C(O)NR^{35}SO_2R^{35}$, $SO_2NH_2$, $SO_2NHR^{35}$, $SO_2N(R^{35})_2$, $C(O)H$, $C(O)OH$, $C(N)NH_2$, $C(N)NHR^{35}$, $C(N)N(R^{35})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{35}$ is alkyl, alkenyl, alkynyl, aryl, heteroaryl, cycloalkyl, cycloalkenyl, heterocycloalkyl or heterocycloalkenyl;

wherein the cyclic moieties represented by $R^{26}$, $R^{27}$, $R^{28}$, $R^{31}$, $R^{32}$, $R^{33}$, and $R^{35}$ are unsubstituted or substituted with one or more independently selected $R^{36}$, $OR^{36}$, $SR^{36}$, $S(O)R^{36}$, $SO_2R^{36}$, $C(O)R^{36}$, $CO(O)R^{36}$, $OC(O)R^{36}$, $OC(O)OR^{36}$, $NH_2$, $NHR^{36}$, $N(R^{36})_2$, $NHC(O)R^{36}$, $NR^{36}C(O)R^{36}$, $NHS(O)_2R^{36}$, $NR^{36}S(O)_2R^{36}$, $NHC(O)OR^{36}$, $NR^{36}C(O)OR^{36}$, $NHC(O)NH_2$, $NHC(O)NHR^{36}$, $NHC(O)N(R^{36})_2$, $NR^{36}C(O)NHR^{36}$, $NR^{36}C(O)N(R^{36})_2$, $C(O)NH_2$, $C(O)NHR^{36}$, $C(O)N(R^{36})_2$, $C(O)NHOH$, $C(O)NHOR^{36}$, $C(O)NHSO_2R^{36}$, $C(O)NR^{36}SO_2R^{36}$, $SO_2NH_2$, $SO_2NHR^{36}$, $SO_2N(R^{36})_2$, $C(O)H$, $C(O)OH$, $C(N)NH_2$, $C(N)NHR^{36}$, $C(N)N(R^{36})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{36}$ is $R^{37}$, $R^{38}$, $R^{30}$ or $R^{40}$;

$R^{37}$ is aryl;

$R^{38}$ is heteroaryl;

$R^{30}$ is cycloalkyl, cycloalkenyl, heterocycloalkyl or heterocycloalkenyl;

$R^{40}$ is alkyl, alkenyl, or alkenyl, each of which is unsubstituted or substituted with one or two or three independently selected $R^{41}$, $OR^{41}$, $SR^{41}$, $S(O)R^{41}$, $SO_2R^{41}$, $C(O)R^{41}$, $CO(O)R^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $NHS(O)_2R^{41}$, $N R^{41}S(O)_2R^{41}$, $NHC(O)OR^{41}$, $NR^{41}C(O)OR^{41}$, $NHC(O)NH_2$, $NHC(O)NHR^{41}$, $NHC(O)N(R^{41})_2$, $NR^{41}C(O)NHR^{41}$, $NR^{41}C(O)N(R^{41})_2$, $C(O)NH_2$, $C(O)NHR^{41}$, $C(O)N(R^{41})_2$, $C(O)NHOH$, $C(O)NHOR^{41}$, $C(O)NHSO_2R^{41}$, $C(O)NR^{41}SO_2R^{41}$, $SO_2NH_2$, $SO_2NHR^{41}$, $SO_2N(R^{41})_2$, $C(O)H$, $C(O)OH$, $C(N)NH_2$, $C(N)NHR^{41}$, $C(N)N(R^{41})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents;

$R^{41}$ is alkyl, alkenyl, alkenyl, aryl, heteroaryl, cycloalkyl, cycloalkenyl, heterocycloalkyl, or heterocycloalkenyl; and the moieties represented by $R^{37}$, $R^{38}$, and $R^{39}$ are unsubstituted or substituted with one or more independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, $(O)$, $CN$, $N_3$, $NO_2$, $CF_3$, $CF_2CF_3$, $OCF_3$, $OCF_2CF_3$, $F$, $Cl$, $Br$ or $I$ substituents.

In one embodiment of Formula (I), $X^1$ is heteroaryl; optionally substituted with one, two, three, or four $R^4$;

$X^2$ is $Y^1$ is hydrogen, $(CH_2)_tR^5$, $(CH_2)_tOR^5$, $(CH_2)_tNHR^5$, $(CH_2)_tN(R^5)_2$, or $(CH_2)_tSR^5$;

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^6R^7$, $OR^6$, $CN$, $NO_2$, halogen, $C(O)OR^6$, $C(O)NR^6R^7$, $NR^6C(O)R^7$, $NR^6S(O)_2R^8$, $NR^6S(O)R^8$, $S(O)_2R^8$, $S(O)R^8$ and $R^8$;

$R^5$ is aryl or heterocyclyl; optionally substituted with one, two, three, or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $CO(O)H$, $C(O)H$, $OH$, $CN$, $N_3$, $NO_2$, $F$, $Cl$, $Br$ and $I$;

$R^6$ and $R^7$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^8$, at each occurrence, is independently selected from the group consisting of $C_{1-4}$ alkyl, $C_{2-4}$ alkenyl, $C_{2-4}$ alkynyl and $C_{1-4}$ haloalkyl;

$R^6$ and $R^7$, or $R^6$ and $R^8$, at each occurrence, together with the atom to which each is attached, are optionally combined to form a heterocyclyl;

$R^9$, at each occurrence, is independently selected from the group consisting of $C_{1-6}$ alkyl, $C_{2-6}$ alkenyl, $C_{2-6}$ alkynyl, and $C_{1-6}$ haloalkyl;

t is 1, 2, or 3;

m is 0, 1, 2, or 3;

n is 0, 1, 2, 3, 4, 5, or 6;

p is 0, 1, or 2;

$Z^1$ is aryl, heteroaryl, cycloalkyl, cycloalkenyl, heterocloalkyl, or heterocycloalkenyl;

wherein $Z^1$ is unsubstituted or substituted with one or two or three or four or five independently selected $R^{10}$, $OR^{10}$, $SR^{10}$, $S(O)R^{10}$, $SO_2R^{10}$, $C(O)R^{10}$, $C(O)OR^{10}$, $OC(O)R^{10}$, $NHR^{10}$, $N(R^{10})_2$, $C(N)C(O)R^{10}$, $C(O)NHR^{10}$, $C(O)N(R^{10})_2$, $C(O)NHOH$, $C(O)NHOR^{10}$, $C(O)NHSO_2R^{10}$, $NHC(O)R^{10}$, $NR^{10}C(O)R^{10}$, $NHC(O)OR^{10}$, $NR^{10}C(O)OR^{10}$, $NR^{10}C(O)NHR^{10}$, $NR^{10}C(O)N(R^{10})_2$, $NHC(O)NH_2$, $NHC(O)NHR^{10}$, $NHC(O)N(R^{10})_2$, $SO_2NH_2$, $SO_2NHR^{10}$, $SO_2N(R^{10})_2$, $NHS(O)R^{10}$, $NHSO_2R^{10}$, $NR^{10}SO_2R^{10}$, $NHSO_2NHR^{10}$, $N(CH_3)SO_2N(CH_3)R^{10}$, $(O)$, $NH_2$, $NO_2$, $N_3$, $OH$, $F$, $Cl$, $Br$, $I$, $CN$, $CF_3$, $OCF_3$, $CF_2CF_3$, $OCF_2CF_3$, $C(O)H$, $C(O)OH$, $C(N)NH_2$, $C(N)NHR^{10}$, $C(N)N(R^{10})_2$, $CNOH$, $CNOCH_3$, or $C(O)NH_2$ substituents;

$R^{10}$ is $R^{11}$, $R^{12}$, $R^{13}$ or $R^{14}$;

$R^{11}$ is aryl;

$R^{12}$ is heteroaryl;

$R^{13}$ is cycloalkyl, cycloalkenyl, cycloalkynyl, heterocycloalkyl or heterocycloalkenyl;

$R^{14}$ is alkyl, alkenyl or alkynyl, each of which is unsubstituted or substituted with one or two or three independently selected $R^{15D}$, $NC(R^{15A})(R^{15B})$, $R^{15}$, $OR^{15}$, $SR^{15}$, $S(O)R^{15}$, $SO_2R^{15}$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NHC(O)OR^{15}$, $SO_2NH_2$, $SO_2NHR^{15}$, $SO_2N(R^{15})_2$, $NHC(O)NH_2$, $NHC(O)NHR^{15}$, $NHC(O)CH(CH_3)NHC(O)CH(CH_3)NH_2$, $NHC(O)CH(CH_3)NHC(O)CH(CH_3)NHR^{15}$, $OH$, $(O)$, $C(O)OH$, $N_3$, $CN$, $NH_2$, $CF_3$, $CF_2CF_3$, $F$, $Cl$, $Br$ or $I$ substituents;

$R^{15A}$ and $R^{15B}$ are independently selected alkyl or, together with the N to which they are attached, $R^{15C}$;

$R^{15C}$ is aziridin-1-yl, azetidin-1-yl, pyrrolidin-1-yl or piperidin-1-yl, each having one $CH_2$ moiety unreplaced or replaced with $O$, $C(O)$, $CNOH$, $CNOCH_3$, $S$, $S(O)$, $SO_2$ or $NH$;

$R^{15D}$ is $C_2$-$C_5$-spiroalkyl, each of which is unsubstituted or substituted with $OH$, $(O)$, $N_3$, $CN$, $CF_3$, $CF_2CF_3$, $F$, $Cl$, $Br$, $I$, $NH_2$, $NH(CH_3)$ or $N(CH_3)_2$;

$R^{15}$ is $R^{16}$, $R^{17}$, $R^{18}$ or $R^{19}$;

$R^{16}$ is aryl;

$R^{17}$ is heteroaryl;

$R^{18}$ is cycloalkyl, cycloalkenyl, heterocycloalkyl, or heterocycloalkenyl; and $R^{19}$ is alkyl.

In one embodiment of Formula (I), m is 0, 1, 2, or 3; n is 0, 1, 2, 3, 4, 5, or 6; and p is 0, 1, or 2. In another embodiment of Formula (I), n is 0 or 1. In another embodiment of Formula (I), n is 0 or 1; and each $R^2$ is independently deuterium or $C_{1-6}$ alkyl. In another embodiment of Formula (I), m, n, and p are 0.

In one embodiment of Formula (I), $X^1$ is heteroaryl, which is optionally substituted with one, two, three or four $R^4$. In another embodiment of Formula (I), $X^1$ is heteroaryl, which is unsubstituted. In another embodiment of Formula (I), $X^1$ is heteroaryl, which is substituted with one $R^4$. In another embodiment of Formula (I), $X^1$ is heteroaryl, which is substituted with two $R^4$. In another embodiment of Formula (I), $X^1$ is heteroaryl, which is substituted with one $R^4$, and $R^4$ is $OR^6$ or halogen. In another embodiment of Formula (I), $X^1$ is heteroaryl, which is substituted with two $R^4$, and each $R^4$ is independently $OR^6$ or halogen. In another embodiment of Formula (I), $X^1$ is heteroaryl, which is substituted with one $R^4$, and $R^4$ is halogen. In another embodiment of Formula (I), $X^1$ is heteroaryl, which is substituted with two $R^4$, and each $R^4$ is independently F. In another embodiment of Formula (I), $X^1$ is heteroaryl, which is substituted with one $R^4$, and $R^4$ is F.

In one embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$. In another embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$. In another embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is $OR^6$ or halogen. In another embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently $OR^6$ or halogen. In another embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is Cl, F, or methoxy. In another embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two $R^4$, and each $R^4$ is independently F. In another embodiment of Formula (I), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one $R^4$, and $R^4$ is independently F.

In one embodiment of Formula (I), $X^1$ is benzo[d]thiazolyl, which is optionally substituted with one, two, three or four $R^4$. In another embodiment of Formula (I), $X^1$ is benzo[d]thiazolyl, which is unsubstituted. In another embodiment of Formula (I), $X^1$ is benzo[d]thiazolyl, which is substituted with one $R^4$. In another embodiment of Formula (I), $X^1$ is benzo[d]thiazolyl, which is substituted with two $R^4$. In another embodiment of Formula (I), $X^1$ is benzo[d]thiazolyl, which is substituted with one $R^4$, and $R^4$ is $OR^6$ or halogen. In another embodiment of Formula (I), $X^1$ is benzo[d]thiazolyl, which is substituted with two $R^4$, and each $R^4$ is independently $OR^6$ or halogen. In another embodiment of Formula (I), $X^1$ is benzo[d]thiazolyl, which is substituted with one $R^4$, and $R^4$ is Cl, F, or methoxy. In another embodiment of Formula (I), $X^1$ is benzo[d]thiazolyl, which is substituted with two $R^4$, and each $R^4$ is independently F. In another embodiment of Formula (I), $X^1$ is benzo[d]thiazolyl, which is substituted with one $R^4$, and $R^4$ is independently F.

In one embodiment of Formula (I), $X^1$ is

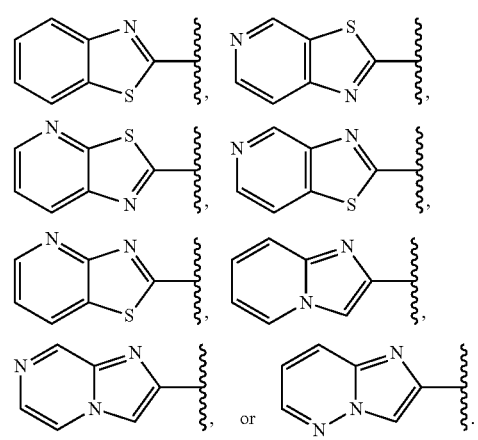

In another embodiment of Formula (I), $X^1$ is

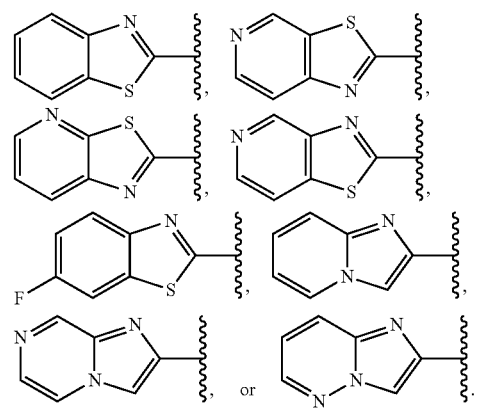

In another embodiment of Formula (I), $X^1$ is

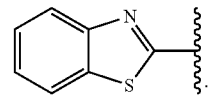 [SMILES: *c1nc2ccccc2s1]

In one embodiment of Formula (I), $X^2$ is

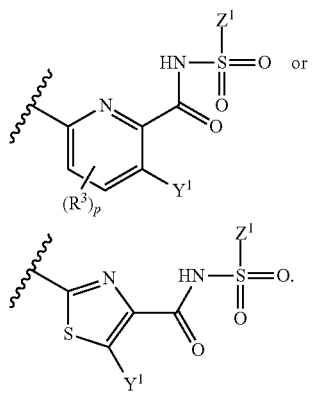

In another embodiment of Formula (I), $X^2$ is

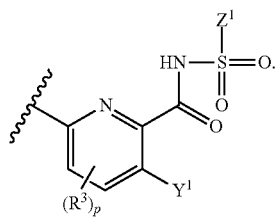

In another embodiment of Formula (I), $X^2$ is

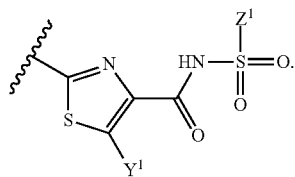

In one embodiment of Formula (I), $Y^1$ is hydrogen, $(CH_2)_t R^5$, $(CH_2)_t OR^5$, $(CH_2)_t NHR^5$, $(CH_2)_t N(R^5)_2$, or $(CH_2)_t SR^5$. In another embodiment of Formula (I), $Y^1$ is hydrogen or $(CH_2)_t R^5$. In another embodiment of Formula (I), $Y^1$ is hydrogen. In another embodiment of Formula (I), $Y^1$ is $(CH_2)_t R^5$; $R^5$ is optionally substituted phenyl or heteroaryl; and t is 1, 2, or 3. In another embodiment of Formula (I), $Y^1$ is $(CH_2)_t R^5$; $R^5$ is phenyl; and t is 1, 2, or 3.

In one embodiment of Formula (I), $Z^1$ is aryl, heteroaryl, cycloalkyl, cycloalkenyl, heterocycloalkyl, or heterocycloalkenyl. In another embodiment of Formula (I), $Z^1$ is unsubstituted or substituted phenyl or pyridinyl. In another embodiment of Formula (I), $Z^1$ is unsubstituted or substituted phenyl.

In one embodiment of Formula (I), $Z^1$ is substituted with one or two or three or four or five independently selected $R^{10}$, $OR^{10}$, $SR^{10}$, $S(O)R^{10}$, $SO_2R^{10}$, $C(O)R^{10}$, $C(O)OR^{10}$, $OC(O)R^{10}$, $NHR^{10}$, $N(R^{10})_2$, $C(N)C(O)R^{10}$, $C(O)NHR^{10}$, $C(O)N(R^{10})_2$, $C(O)NHOH$, $C(O)NHOR^{10}$, $C(O)NHSO_2R^{10}$, $NHC(O)R^{10}$, $NR^{10}C(O)R^{10}$, $NHC(O)OR^{10}$, $NR^{10}C(O)OR^{10}$, $NR^{10}C(O)NHR^{10}$, $NR^{10}C(O)N(R^{10})_2$, $NHC(O)NH_2$, $NHC(O)NHR^{10}$, $NHC(O)N(R^{10})_2$, $SO_2NH_2$, $SO_2NHR^{10}$, $SO_2N(R^{10})_2$, $NHS(O)R^{10}$, $NHSO_2R^{10}$, $NR^{10}SO_2R^{10}$, $NHSO_2NHR^{10}$, $N(CH_3)SO_2N(CH_3)R^{10}$, $(O)$, $NH_2$, $NO_2$, $N_3$, OH, F, Cl, Br, I, CN, $CF_3$, $OCF_3$, $CF_2CF_3$, $OCF_2CF_3$, $C(O)H$, $C(O)OH$, $C(N)NH_2$, $C(N)NHR^{10}$, $C(N)N(R^{10})_2$, CNOH, $CNOCH_3$, or $C(O)NH_2$ substituents. In another embodiment of Formula (I), $Z^1$ is substituted with two independently selected $SO_2R^{10}$, $NHR^{10}$, $CF_3$, $NO_2$, or F. In another embodiment of Formula (I), $Z^1$ is substituted with $NHR^{10}$ and $SO_2R^{10}$, $NO_2$, $CF_3$, or F. In another embodiment of Formula (I), $Z^1$ is substituted with $NHR^{10}$ and $SO_2CF_3$, $SO_2CF_2Cl$, $CF_3$, $NO_2$, or F. In one embodiment of Formula (I), $Z^1$ is substituted with $NHR^{10}$ and $SO_2CF_3$, $SO_2CF_2Cl$, $CF_3$, $NO_2$, or F; wherein $R^{10}$ is $R^{14}$; $R^{14}$ is alkyl which is unsubstituted or substituted with one or two or three independently selected OH, $R^{15}$, $OR^{15}$, $SR^{15}$, or $N(R^{15})_2$ substituents; $R^{15}$ is $R^{16}$, $R^{18}$ or $R^{19}$; $R^{16}$ is aryl; $R^{18}$ is heterocycloalkyl; and $R^{19}$ is alkyl.

In one embodiment of Formula (I), $X^1$ is heteroaryl; optionally substituted with one, two, three, or four $R^4$; $X^2$ is

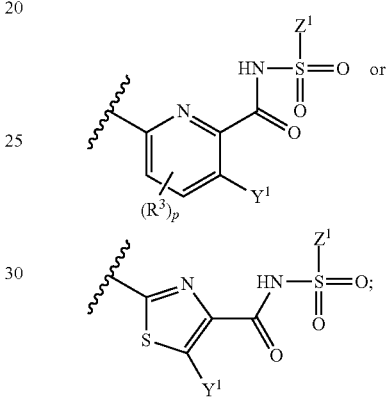

$Y^1$ is hydrogen or $(CH_2)_t R^5$;
$R^4$, at each occurrence, is halogen;
$R^5$ is aryl;
t is 1, 2, or 3;
m is 0;
n is 0;
p is 0;
$Z^1$ is aryl;
wherein $Z^1$ is substituted with one or two or three or four or five independently selected $SO_2R^{10}$, $NHR^{10}$, $NO_2$, F, or $CF_3$, substituents;
$R^{10}$ is $R^{14}$;
$R^{14}$ is alkyl, which is unsubstituted or substituted with one or two or three independently selected $R^{15}$, $OR^{15}$, $SR^{15}$, $N(R^{15})_2$, OH, $CF_3$, F, or Cl substituents;
$R^{15}$ is $R^{16}$, $R^{18}$ or $R^{19}$;
$R^{16}$ is aryl;
$R^{18}$ is heterocycloalkyl; and
$R^{19}$ is alkyl.

Still another embodiment pertains to a compound having Formula (I) selected from the group consisting of
N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;
N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-(6-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide;

N-(1,3-benzothiazol-2-yl)-2-(4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(5-benzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(5-benzyl-4-{[(4-{[3-(dimethylamino)propyl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-[(trifluoromethyl)sulfonyl]phenyl)sulfonyl]carbamoyl}-5-(2-phenylethyl)-1,3-thiazol-2-yl]-1,2,3,4-tetrahydroisoquinoline-8-carboxamide;

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-nitrophenyl)sulfonyl]carbamoyl}-5-(2-phenylethyl)-1,3-thiazol-2-yl]-1,2,3,4-tetrahydroisoquinoline-8-carboxamide;

N-(1,3-benzothiazol-2-yl)-2-(4-{[(4-{[(2R)-4-hydroxy-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

N-(imidazo[1,2-a]pyridin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-a]pyridin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(imidazo[1,2-a]pyrazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-a]pyrazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(imidazo[1,2-b]pyridazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-b]pyridazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(6-fluoro-1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(6-fluoro-1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(1,3-benzothiazol-2-yl)-2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-[6-({[3-(methylsulfonyl)-4-{[(2R)-4-(morpholin-4-yl)-1-(phenylsulfanyl)butan-2-yl]

amino}phenyl]sulfonyl}carbamoyl)pyridin-2-yl]-1,2,3,4-tetrahydroisoquinoline-8-carboxamide;

N-(1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-b]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-c]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[4,5-c]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-a]pyridin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(imidazo[1,2-a]pyrazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-a]pyrazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(imidazo[1,2-b]pyridazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-b]pyridazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(6-fluoro-1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(6-fluoro-1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

N-(6-fluoro-1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(6-fluoro-1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

N-(1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-b]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-c]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[4,5-c]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-a]pyridin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(imidazo[1,2-a]pyrazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-a]pyrazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(imidazo[1,2-b]pyridazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-b]pyridazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(6-fluoro-1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(6-fluoro-1,3-benzothiazol-2-yl)-2-[44 {[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(1,3-benzothiazol-2-yl)-2-(6-{[(4-{[(2R)-4-(dimethylamino)-1-phenoxybutan-2-yl]amino}-3-nitrophenyl)sulfonyl]carbamoyl}pyridin-2-yl)-1,2,3,4-tetrahydroisoquinoline-8-carboxamide;

N-(1,3-benzothiazol-2-yl)-2-(4-{[(4-{[(2R)-4-(dimethylamino)-1-phenoxybutan-2-yl]amino}-3-nitrophenyl)sulfonyl]carbamoyl}-1,3-thiazol-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol- 2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-1,2,3,4-tetrahydroisoquinoline-8-carboxamide;

N-(1,3-benzothiazol-2-yl)-2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; and therapeutically acceptable salts, metabolites, prodrugs, salts of metabolites, and salts of prodrugs thereof.

Still another embodiment pertains to a compound having Formula (I), selected from the group consisting of N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(6-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide;

N-(1,3-benzothiazol-2-yl)-2-(4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(5-benzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(5-benzyl-4-{[(4-{[3-(dimethylamino)propyl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-[(trifluoromethyl)sulfonyl]phenyl)sulfonyl]carbamoyl}-5-(2-phenylethyl)-1,3-thiazol-2-yl]-1,2,3,4-tetrahydroisoquinoline-8-carboxamide;

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-nitrophenyl)sulfonyl]carbamoyl}-5-(2-phenylethyl)-1,3-thiazol-2-yl]-1,2,3,4-tetrahydroisoquinoline-8-carboxamide;

N-(1,3-benzothiazol-2-yl)-2-(4-{[(4-{[(2R)-4-hydroxy-1-(phenylsulfanyl)butan-2-yl]amino}-3-[(trifluoromethyl)

sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide; and therapeutically acceptable salts, metabolites, prodrugs, salts of metabolites, and salts of prodrugs thereof.

In another aspect, the present invention provides compounds of Formula (II)

(II)

and therapeutically acceptable salts, metabolites, prodrugs, salts of metabolites, and salts of prodrugs thereof, wherein $X^1, Y^1, Z^1, R^1, R^2, R^3$, m, n, and p are as described herein for Formula (I).

One embodiment pertains to compounds and therapeutically acceptable salts, metabolites, prodrugs, salts of metabolites, and salts of prodrugs thereof, which are inhibitors of anti-apoptotic Bcl-xL proteins, the compounds having Formula (II)

Formula (II)

wherein $X^1$ is heteroaryl; optionally substituted with one, two, three, or four $R^4$;

$Y^1$ is hydrogen, $(CH_2)_tR^5$, $(CH_2)_tOR^5$, $(CH_2)_tNHR^5$, $(CH_2)_tN(R^5)_2$, or $(CH_2)_tSR^5$;

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^4$, at each occurrence, is independently selected from the group consisting of $NR^6R^7$, $OR^6$, CN, $NO_2$, halogen, C(O)$OR^6$, C(O)$NR^6R^7$, $NR^6C(O)R^7$, $NR^6S(O)_2R^8$, $NR^6S(O)R^8$, $S(O)_2R^8$, $S(O)R^8$ and $R^8$;

$R^5$ is aryl or heterocyclyl; optionally substituted with one, two, three, or four substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, C(O)NHOH, $C(O)NHOR^9$, $C(O)NHSO_2R^9$, $C(O)NR^9SO_2R^9$, $SO_2NH_2$, $SO_2NHR^9$, $SO_2N(R^9)_2$, CO(O)H, C(O)H, OH, CN, $N_3$, $NO_2$, F, Cl, Br and I;

$R^6$ and $R^7$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;

$R^8$, at each occurrence, is independently selected from the group consisting of $C_{1-4}$ alkyl, $C_{2-4}$ alkenyl, $C_{2-4}$ alkynyl and $C_{1-4}$ haloalkyl;

$R^6$ and $R^7$, or $R^6$ and $R^8$, at each occurrence, together with the atom to which each is attached, are optionally combined to form a heterocyclyl;

$R^9$, at each occurrence, is independently selected from the group consisting of $C_{1-6}$ alkyl, $C_{2-6}$ alkenyl, $C_{2-6}$ alkynyl, and $C_{1-6}$ haloalkyl;

t is 1, 2, or 3;

m is 0, 1, 2, or 3;

n is 0, 1, 2, 3, 4, 5, or 6;

p is 0, 1, or 2;

$Z^1$ is aryl, heteroaryl, cycloalkyl, cycloalkenyl, heterocycloalkyl, or heterocycloalkenyl;

wherein $Z^1$ is unsubstituted or substituted with one or two or three or four or five independently selected $R^{10}$, $OR^{10}$, $SR^{10}$, $S(O)R^{10}$, $SO_2R^{10}$, $C(O)R^{10}$, $C(O)OR^{10}$, $OC(O)R^{10}$, $NHR^{10}$, $N(R^{10})_2$, $C(N)C(O)R^{10}$, $C(O)NHR^{10}$, $C(O)N(R^{10})_2$, C(O)NHOH, $C(O)NHOR^{10}$, $C(O)NHSO_2R^{10}$, $NHC(O)R^{10}$, $NR^{10}C(O)R^{10}$, $NHC(O)OR^{10}$, $NR^{10}C(O)OR^{10}$, $NR^{10}C(O)NHR^{10}$, $NR^{10}C(O)N(R^{10})_2$, $NHC(O)NH_2$, $NHC(O)NHR^{10}$, $NHC(O)N(R^{10})_2$, $SO_2NH_2$, $SO_2NHR^{10}$, $SO_2N(R^{10})_2$, $NHS(O)R^{10}$, $NHSO_2R^{10}$, $NR^{10}SO_2R^{10}$, $NHSO_2NHR^{10}$, $N(CH_3)SO_2N(CH_3)R^{10}$, (O), $NH_2$, $NO_2$, $N_3$, OH, F, Cl, Br, I, CN, $CF_3$, $OCF_3$, $CF_2CF_3$, $OCF_2CF_3$, C(O)H, C(O)OH, $C(N)NH_2$, $C(N)NHR^{10}$, $C(N)N(R^{10})_2$, CNOH, $CNOCH_3$, or $C(O)NH_2$ substituents;

$R^{10}$ is $R^{11}$, $R^{12}$, $R^{13}$ or $R^{14}$;

$R^{11}$ is aryl;

$R^{12}$ is heteroaryl;

$R^{13}$ is cycloalkyl, cycloalkenyl, cycloalkynyl, heterocycloalkyl or heterocycloalkenyl;

$R^{14}$ is alkyl, alkenyl or alkynyl, each of which is unsubstituted or substituted with one or two or three independently selected $R^{15D}$, $NC(R^{15A})(R^{15B})$, $R^{15}$, $OR^{15}$, $SR^{15}$, $S(O)R^{15}$, $SO_2R^{15}$, $NHR^{15}$, $N(R^{15})_2$, $C(O)R^{15}$, $C(O)NH_2$, $C(O)NHR^{15}$, $C(O)N(R^{15})_2$, $NHC(O)R^{15}$, $NR^{15}C(O)R^{15}$, $NHSO_2R^{15}$, $NHC(O)OR^{15}$, $SO_2NH_2$, $SO_2NHR^{15}$, $SO_2N(R^{15})_2$, $NHC(O)NH_2$, $NHC(O)NHR^{15}$, $NHC(O)CH(CH_3)NHC(O)CH(CH_3)NH_2$, $NHC(O)CH(CH_3)NHC(O)CH(CH_3)NHR^{15}$, OH, (O), C(O)OH, $N_3$, CN, $NH_2$, $CF_3$, $CF_2CF_3$, F, Cl, Br or I substituents;

$R^{15A}$ and $R^{15B}$ are independently selected alkyl or, together with the N to which they are attached, $R^{15C}$;

$R^{15C}$ is aziridin-1-yl, azetidin-1-yl, pyrrolidin-1-yl or piperidin-1-yl, each having one $CH_2$ moiety unreplaced or replaced with O, C(O), CNOH, $CNOCH_3$, S, S(O), $SO_2$ or NH;

$R^{15D}$ is $C_2$-$C_5$-spiroalkyl, each of which is unsubstituted or substituted with OH, (O), $N_3$, CN, $CF_3$, $CF_2CF_3$, F, Cl, Br, I, $NH_2$, $NH(CH_3)$ or $N(CH_3)_2$;

$R^{15}$ is $R^{16}$, $R^{17}$, $R^{18}$ or $R^{19}$;

$R^{16}$ is aryl;

$R^{17}$ is heteroaryl;

$R^{18}$ is cycloalkyl, cycloalkenyl, heterocycloalkyl, or heterocycloalkenyl;

$R^{19}$ is alkyl, alkenyl or alkynyl, each of which is unsubstituted or substituted with one or two or three independently selected $R^{20}$, $OR^{20}$, $SR^{20}$, $S(O)R^{20}$, $SO_2R^{20}$, $C(O)R^{20}$, $CO(O)R^{20}$, $OC(O)R^{20}$, $OC(O)OR^{20}$, $NH_2$, $NHR^{20}$, $N(R^{20})_2$, $NHC(O)R^{20}$, $NR^{20}C(O)R^{20}$, $NHS(O)_2R^{20}$, $NR^{20}S(O)_2R^{20}$, $NHC(O)OR^{20}$, $NR^{20}C(O)OR^{20}$, $NHC(O)NH_2$, $NHC(O)NHR^{20}$, $NHC(O)N(R^{20})_2$, $NR^{20}C(O)NHR^{20}$, $NR^{20}C(O)N(R^{20})_2$, $C(O)NH_2$, $C(O)NHR^{20}$, $C(O)N(R^{20})_2$, $C(O)NHOH$, $C(O)NHOR^{20}$, $C(O)NHSO_2R^{20}$, $C(O)NR^{20}SO_2R^{20}$, $SO_2NH_2$, $SO_2NHR^{20}$, $SO_2N(R^{20})_2$, $C(O)H$, $C(O)OH$, $C(N)NH_2$, $C(N)NHR^{20}$, $C(N)N(R^{20})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{20}$ is $R^{21}$, $R^{22}$, $R^{23}$ or $R^{24}$;

$R^{21}$ is aryl;

$R^{22}$ is heteroaryl;

$R^{23}$ is cycloalkane, cycloalkene, heterocycloalkane or heterocycloalkene;

$R^{24}$ is alkyl, alkenyl or alkynyl;

wherein the cyclic moieties represented by $R^{11}$, $R^{12}$, $R^{13}$, $R^{15C}$, $R^{15D}$, $R^{16}$, $R^{17}$, $R^{18}$, $R^{21}$, $R^{22}$, and $R^{23}$ are independently unsubstituted, further unsubstituted, substituted or further substituted with one or more independently selected $R^{25}$, $OR^{25}$, $SR^{25}$, $S(O)R^{25}$, $SO_2R^{25}$, $C(O)R^{25}$, $CO(O)R^{25}$, $OC(O)R^{25}$, $OC(O)OR^{25}$, $NH_2$, $NHR^{25}$, $N(R^{25})_2$, $NHC(O)R^{25}$, $NR^{25}C(O)R^{25}$, $NHS(O)_2R^{25}$, $NR^{25}S(O)_2R^{25}$, $NHC(O)OR^{25}$, $NR^{25}C(O)OR^{25}$, $NHC(O)NH_2$, $NHC(O)NHR^{25}$, $NHC(O)N(R^{25})_2$, $NR^{25}C(O)NHR^{25}$, $NR^{25}C(O)N(R^{25})_2$, $C(O)NH_2$, $C(O)NHR^{25}$, $C(O)N(R^{25})_2$, $C(O)NHOH$, $C(O)NHOR^{25}$, $C(O)NHSO_2R^{25}$, $C(O)NR^{25}SO_2R^{25}$, $SO_2NH_2$, $SO_2NHR^{25}$, $SO_2N(R^{25})_2$, $C(O)H$, $C(O)OH$, $C(N)NH_2$, $C(N)NHR^{25}$, $C(N)N(R^{25})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{25}$ is $R^{26}$, $R^{27}$, $R^{28}$ or $R^{29}$;

$R^{26}$ is aryl;

$R^{27}$ is heteroaryl;

$R^{28}$ is cycloalkyl, cycloalkenyl, heterocycloalkyl or heterocycloalkenyl;

$R^{29}$ is alkyl, alkenyl, or alkynyl, each of which is unsubstituted or substituted with one or two or three independently selected $R^{30}$, $OR^{30}$, $SR^{30}$, $S(O)R^{30}$, $SO_2R^{30}$, $C(O)R^{30}$, $CO(O)R^{30}$, $OC(O)R^{30}$, $OC(O)OR^{30}$, $NH_2$, $NHR^{30}$, $N(R^{30})_2$, $NHC(O)R^{30}$, $NR^{30}C(O)R^{30}$, $NHS(O)_2R^{30}$, $NR^{30}S(O)_2R^{30}$, $NHC(O)OR^{30}$, $NR^{30}C(O)OR^{30}$, $NHC(O)NH_2$, $NHC(O)NHR^{30}$, $NHC(O)N(R^{30})_2$, $NR^{30}C(O)NHR^{30}$, $NR^{30}C(O)N(R^{30})_2$, $C(O)NH_2$, $C(O)NHR^{30}$, $C(O)N(R^{30})_2$, $C(O)NHOH$, $C(O)NHOR^{30}$, $C(O)NHSO_2R^{30}$, $C(O)NR^{30}SO_2R^{30}$, $SO_2NH_2$, $SO_2NHR^{30}$, $SO_2N(R^{30})_2$, $C(O)H$, $C(O)OH$, $C(N)NH_2$, $C(N)NHR^{30}$, $C(N)N(R^{30})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{30}$ is $R^{31}$, $R^{32}$, $R^{33}$ or $R^{34}$;

$R^{31}$ is aryl;

$R^{32}$ is heteroaryl;

$R^{33}$ is cycloalkyl, cycloalkenyl, heterocycloalkyl or heterocycloalkenyl;

$R^{34}$ is alkyl, alkenyl, or alkynyl, each of which is unsubstituted or substituted with one or two or three independently selected $R^{35}$, $OR^{35}$, $SR^{35}$, $S(O)R^{35}$, $SO_2R^{35}$, $C(O)R^{35}$, $CO(O)R^{35}$, $OC(O)R^{35}$, $OC(O)OR^{35}$, $NH_2$, $NHR^{35}$, $N(R^{35})_2$, $NHC(O)R^{35}$, $NR^{35}C(O)R^{35}$, $NHS(O)_2R^{35}$, $NR^{35}S(O)_2R^{35}$, $NHC(O)OR^{35}$, $NR^{35}C(O)OR^{35}$, $NHC(O)NH_2$, $NHC(O)NHR^{35}$, $NHC(O)N(R^{35})_2$, $NR^{35}C(O)NHR^{35}$, $NR^{35}C(O)N(R^{35})_2$, $C(O)NH_2$, $C(O)NHR^{35}$, $C(O)N(R^{35})_2$, $C(O)NHOH$, $C(O)NHOR^{35}$, $C(O)NHSO_2R^{35}$, $C(O)NR^{35}SO_2R^{35}$, $SO_2NH_2$, $SO_2NHR^{35}$, $SO_2N(R^{35})_2$, $C(O)H$, $C(O)OH$, $C(N)NH_2$, $C(N)NHR^{35}$, $C(N)N(R^{35})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{35}$ is alkyl, alkenyl, alkynyl, aryl, heteroaryl, cycloalkyl, cycloalkenyl, heterocycloalkyl or heterocycloalkenyl;

wherein the cyclic moieties represented by $R^{26}$, $R^{27}$, $R^{28}$, $R^{31}$, $R^{32}$, $R^{33}$, and $R^{35}$ are unsubstituted or substituted with one or more independently selected $R^{36}$, $OR^{36}$, $SR^{36}$, $S(O)R^{36}$, $SO_2R^{36}$, $C(O)R^{36}$, $CO(O)R^{36}$, $OC(O)R^{36}$, $OC(O)OR^{36}$, $NH_2$, $NHR^{36}$, $N(R^{36})_2$, $NHC(O)R^{36}$, $NR^{36C}(O)R^{36}$, $NHS(O)_2 R^{36}$, $NR^{36}S(O)_2R^{36}$, $NHC(O)OR^{36}$, $NR^{36}C(O)OR^{36}$, $NHC(O)NH_2$, $NHC(O)NHR^{36}$, $NHC(O)N(R^{36})_2$, $NR^{36}C(O)NHR^{36}$, $NR^{36}C(O)N(R^{36})_2$, $C(O)NH_2$, $C(O)NHR^{36}$, $C(O)N(R^{36})_2$, $C(O)NHOH$, $C(O)NHOR^{36}$, $C(O)NHSO_2R^{36}$, $C(O)NR^{36}SO_2R^{36}$, $SO_2NH_2$, $SO_2NHR^{36}$, $SO_2N(R^{36})_2$, $C(O)H$, $C(O)OH$, $C(N)NH_2$, $C(N)NHR^{36}$, $C(N)N(R^{36})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{36}$ is $R^{37}$, $R^{38}$, $R^{30}$ or $R^{40}$;

$R^{37}$ is aryl;

$R^{38}$ is heteroaryl;

$R^{39}$ is cycloalkyl, cycloalkenyl, heterocycloalkyl or heterocycloalkenyl;

$R^{40}$ is alkyl, alkenyl, or alkenyl, each of which is unsubstituted or substituted with one or two or three independently selected $R^{41}$, $OR^{41}$, $SR^{41}$, $S(O)R^{41}$, $SO_2R^{41}$, $C(O)R^{41}$, $CO(O)R^{41}$, $OC(O)R^{41}$, $OC(O)OR^{41}$, $NH_2$, $NHR^{41}$, $N(R^{41})_2$, $NHC(O)R^{41}$, $NR^{41}C(O)R^{41}$, $NHS(O)_2R^{41}$, $N R^{41}S(O)_2R^{41}$, $NHC(O)OR^{41}$, $NR^{41}C(O)OR^{41}$, $NHC(O)NH_2$, $NHC(O)NHR^{41}$, $NHC(O)N(R^{41})_2$, $NR^{41}C(O)NHR^{41}$, $NR^{41}C(O)N(R^{41})_2$, $C(O)NH_2$, $C(O)NHR^{41}$, $C(O)N(R^{41})_2$, $C(O)NHOH$, $C(O)NHOR^{41}$, $C(O)NHSO_2R^{41}$, $C(O)NR^{41}SO_2R^{41}$, $SO_2NH_2$, $SO_2NHR^{41}$, $SO_2N(R^{41})_2$, $C(O)H$, $C(O)OH$, $C(N)NH_2$, $C(N)NHR^{41}$, $C(N)N(R^{41})_2$, $CNOH$, $CNOCH_3$, $OH$, $(O)$, $CN$, $N_3$, $NO_2$, $CF_3$, $CF_2CF_3$, $OCF_3$, $OCF_2CF_3$, F, Cl, Br or I substituents;

$R^{41}$ is alkyl, alkenyl, alkynyl, aryl, heteroaryl, cycloalkyl, cycloalkenyl, heterocycloalkyl, or heterocycloalkenyl; and the moieties represented by $R^{37}$, $R^{38}$, and $R^{39}$ are unsubstituted or substituted with one or more independently selected $NH_2$, $C(O)NH_2$, $C(O)NHOH$, $SO_2NH_2$, $CF_3$, $CF_2CF_3$, $C(O)H$, $C(O)OH$, $C(N)NH_2$, $OH$, $(O)$, $CN$, $N_3$, $NO_2$, $CF_3$, $CF_2CF_3$, $OCF_3$, $OCF_2CF_3$, F, Cl, Br or I substituents.

In one embodiment of Formula (II), $X^1$ is heteroaryl; optionally substituted with one, two, three, or four $R^4$;

$Y^1$ is hydrogen, $(CH_2)_tR^5$, $(CH_2)_tOR^5$, $(CH_2)_tNHR^5$, $(CH_2)_tN(R^5)_2$, or $(CH_2)_tSR^5$;

$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^3$, at each occurrence, is independently selected from the group consisting of halo, $C_{1-6}$ alkyl, $C_{2-6}$ alkenyl, $C_{2-6}$ alkynyl, and $C_{1-6}$ haloalkyl;

R$^4$, at each occurrence, is independently selected from the group consisting of NR$^6$R$^7$, OR$^6$, CN, NO$_2$, halogen, C(O) OR$^6$, C(O)NR$^6$R$^7$, NR$^6$C(O)R$^7$, NR$^6$S(O)$_2$R$^8$, NR$^6$S(O)R$^8$, S(O)$_2$R$^8$, S(O)R$^8$ and R$^8$;

R$^5$ is aryl or heterocyclyl; optionally substituted with one, two, three, or four substituents independently selected from the group consisting of R$^9$, OR$^9$, SR$^9$, S(O)R$^9$, SO$_2$R$^9$, C(O) R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC (O)OR$^9$, NR$^9$C(O)OR$^9$, NHC(O)NH$_2$, NHC(O)NHR$^9$, NHC (O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O) NHSO$_2$R$^9$, C(O)NR$^9$SO$_2$R$^9$, SO$_2$NH$_2$, SO$_2$NHR$^9$, SO$_2$N (R$^9$)$_2$, CO(O)H, C(O)H, OH, CN, N$_3$, NO$_2$, F, Cl, Br and I;

R$^6$ and R$^7$, at each occurrence, are each independently selected from the group consisting of hydrogen, C$_{1-4}$ alkyl, C$_{2-4}$ alkenyl, C$_{2-4}$ alkynyl, C$_{1-4}$ haloalkyl and (CH$_2$)$_{1-4}$ phenyl;

R$^8$, at each occurrence, is independently selected from the group consisting of C$_{1-4}$ alkyl, C$_{2-4}$ alkenyl, C$_{2-4}$ alkynyl and C$_{1-4}$ haloalkyl;

R$^6$ and R$^7$, or R$^6$ and R$^8$, at each occurrence, together with the atom to which each is attached, are optionally combined to form a heterocyclyl;

R$^9$, at each occurrence, is independently selected from the group consisting of C$_{1-6}$ alkyl, C$_{2-6}$ alkenyl, C$_{2-6}$ alkynyl, and C$_{1-6}$ haloalkyl;

t is 1, 2, or 3;
m is 0, 1, 2, or 3;
n is 0, 1, 2, 3, 4, 5, or 6;
p is 0, 1, or 2;

Z$^1$ is aryl, heteroaryl, cycloalkyl, cycloalkenyl, heterocycloalkyl, or heterocycloalkenyl;

wherein Z$^1$ is unsubstituted or substituted with one or two or three or four or five independently selected R$^{10}$, OR$^{10}$, SR$^{10}$, S(O)R$^{10}$, SO$_2$R$^{10}$, C(O)R$^{10}$, C(O)OR$^{10}$, OC(O)R$^{10}$, NHR$^{10}$, N(R$^{10}$)$_2$, C(N)C(O)R$^{10}$, C(O)NHR$^{10}$, C(O)N(R$^{10}$)$_2$, C(O)NHOH, C(O)NHOR$^{10}$, C(O)NHSO$_2$R$^{10}$, NHC(O)R$^{10}$, NR$^{10}$C(O)R$^{10}$, NHC(O)OR$^{10}$, NR$^{10}$C(O)OR$^{10}$, NR$^{10}$C(O) NHR$^{10}$, NR$^{10}$C(O)N(R$^{10}$)$_2$, NHC(O)NH$_2$, NHC(O)NHR$^{10}$, NHC(O)N(R$^{10}$)$_2$, SO$_2$NH$_2$, SO$_2$NHR$^{10}$, SO$_2$N(R$^{10}$)$_2$, NHS (O)R$^{10}$, NHSO$_2$R$^{10}$, NR$^{10}$SO$_2$R$^{10}$, NHSO$_2$NHR$^{10}$, N(CH$_3$) SO$_2$N(CH$_3$)R$^{10}$, (O), NH$_2$, NO$_2$, N$_3$, OH, F, Cl, Br, I, CN, CF$_3$, OCF$_3$, CF$_2$CF$_3$, OCF$_2$CF$_3$, C(O)H, C(O)OH, C(N)NH$_2$, C(N)NHR$^{10}$, C(N)N(R$^{10}$)$_2$, CNOH, CNOCH$_3$, or C(O)NH$_2$ substituents;

R$^{10}$ is R$^{11}$, R$^{12}$, R$^{13}$ or R$^{14}$;
R$^{11}$ is aryl;
R$^{12}$ is heteroaryl;
R$^{13}$ is cycloalkyl, cycloalkenyl, cycloalkynyl, heterocycloalkyl or heterocycloalkenyl;
R$^{14}$ is alkyl, alkenyl or alkynyl, each of which is unsubstituted or substituted with one or two or three independently selected R$^{15D}$, NC(R$^{15A}$)(R$^{15B}$), R$^{15}$, OR$^{15}$, SR$^{15}$, S(O)R$^{15}$, SO$_2$R$^{15}$, NHR$^{15}$, N(R$^{15}$)$_2$, C(O)R$^{15}$, C(O)NH$_2$, C(O)NHR$^{15}$, C(O)N(R$^{15}$)$_2$, NHC(O)R$^{15}$, NR$^{15}$C(O)R$^{15}$, NHSO$_2$R$^{15}$, NHC(O)OR$^{15}$, SO$_2$NH$_2$, SO$_2$NHR$^{15}$, SO$_2$N(R$^{15}$)$_2$, NHC(O) NH$_2$, NHC(O)NHR$^{15}$, NHC(O)CH(CH$_3$)NHC(O)CH(CH$_3$) NH$_2$, NHC(O)CH(CH$_3$)NHC(O)CH(CH$_3$)NHR$^{15}$, OH, (O), C(O)OH, N$_3$, CN, NH$_2$, CF$_3$, CF$_2$CF$_3$, F, Cl, Br or I substituents;

R$^{15A}$ and R$^{15B}$ are independently selected alkyl or, together with the N to which they are attached, R$^{15C}$;

R$^{15C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

R$^{15D}$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{15}$ is R$^{16}$; R$^{17}$; R$^{18}$ or R$^{19}$;
R$^{16}$ is aryl;
R$^{17}$ is heteroaryl;
R$^{18}$ is cycloalkyl, cycloalkenyl, heterocycloalkyl, or heterocycloalkenyl; and
R$^{19}$ is alkyl.

In one embodiment of Formula (II), m is 0, 1, 2, or 3; n is 0, 1, 2, 3, 4, 5, or 6; and p is 0, 1, or 2. In another embodiment of Formula (II), n is 0 or 1. In another embodiment of Formula (II), n is 0 or 1; and each R$^2$ is independently deuterium or C$_{1-6}$ alkyl. In another embodiment of Formula (II), m, n, and p are 0.

In one embodiment of Formula (II), X$^1$ is heteroaryl, which is optionally substituted with one, two, three or four R$^4$. In another embodiment of Formula (II), X$^1$ is heteroaryl, which is unsubstituted. In another embodiment of Formula (II), X$^1$ is heteroaryl, which is substituted with one R$^4$. In another embodiment of Formula (II), X$^1$ is heteroaryl, which is substituted with two R$^4$. In another embodiment of Formula (II), X$^1$ is heteroaryl, which is substituted with one R$^4$, and R$^4$ is OR$^6$ or halogen. In another embodiment of Formula (II), X$^1$ is heteroaryl, which is substituted with two R$^4$, and each R$^4$ is independently OR$^6$ or halogen. In another embodiment of Formula (II), X$^1$ is heteroaryl, which is substituted with one R$^4$, and R$^4$ is halogen. In another embodiment of Formula (II), X$^1$ is heteroaryl, which is substituted with two R$^4$, and each R$^4$ is independently F. In another embodiment of Formula (II), X$^1$ is heteroaryl, which is substituted with one R$^4$, and R$^4$ is F.

In one embodiment of Formula (II), X$^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four R$^4$. In another embodiment of Formula (II), X$^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (II), X$^1$ is benzo[d]thiazolyl, thiazolo[5,4-b]pyridinyl, thiazolo[4,5-c]pyridinyl, imidazo [1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R$^4$. In another embodiment of Formula (II), X$^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R$^4$. In another embodiment of Formula (II), X$^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R$^4$, and R$^4$ is OR$^6$ or halogen. In another embodiment of Formula (II), X$^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R$^4$, and each R$^4$ is independently OR$^6$ or halogen. In another embodiment of Formula (II), X$^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R⁴, and R⁴ is Cl, F, or methoxy. In another embodiment of Formula (II), X¹ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R⁴, and each R⁴ is independently F. In another embodiment of Formula (II), X¹ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R⁴, and R⁴ is independently F.

In one embodiment of Formula (II), X¹ is benzo[d]thiazolyl, which is optionally substituted with one, two, three or four R⁴. In another embodiment of Formula (II), X¹ is benzo[d]thiazolyl, which is unsubstituted. In another embodiment of Formula (II), X¹ is benzo[d]thiazolyl, which is substituted with one R⁴. In another embodiment of Formula (II), X¹ is benzo[d]thiazolyl, which is substituted with two R⁴. In another embodiment of Formula (II), X¹ is benzo[d]thiazolyl, which is substituted with one R⁴, and R⁴ is OR⁶ or halogen. In another embodiment of Formula (II), X¹ is benzo[d]thiazolyl, which is substituted with two R⁴, and each R⁴ is independently OR⁶ or halogen. In another embodiment of Formula (II), X¹ is benzo[d]thiazolyl, which is substituted with one R⁴, and R⁴ is Cl, F, or methoxy. In another embodiment of Formula (II), X¹ is benzo[d]thiazolyl, which is substituted with two R⁴, and each R⁴ is independently F. In another embodiment of Formula (II), X¹ is benzo[d]thiazolyl, which is substituted with one R⁴, and R⁴ is independently F.

In one embodiment of Formula (II), X¹ is

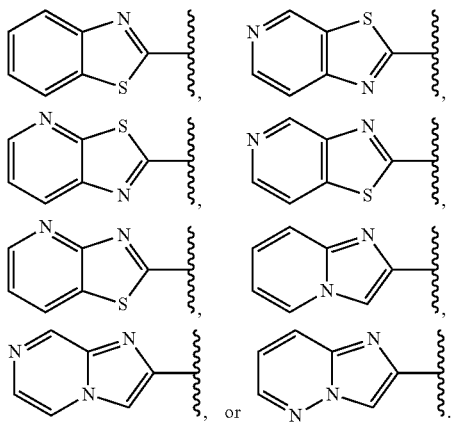

In another embodiment of Formula (II), X¹ is

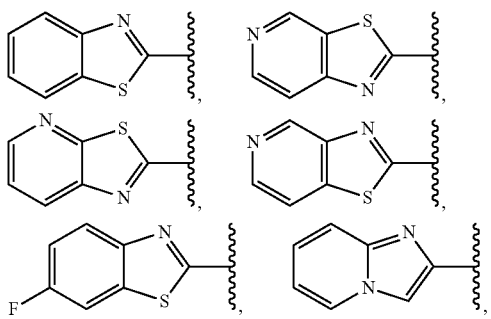

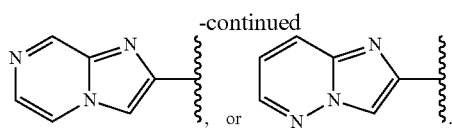

In another embodiment of Formula (II), X¹ is

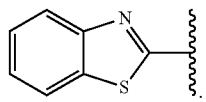 [SMILES: *c1nc2ccccc2s1]

In one embodiment of Formula (II), Y¹ is hydrogen, $(CH_2)_t R^5$, $(CH_2)_t OR^5$, $(CH_2)_t NHR^5$, $(CH_2)_t N(R^5)_2$, or $(CH_2)_t SR^5$. In another embodiment of Formula (II), Y¹ is hydrogen or $(CH_2)_t R^5$. In another embodiment of Formula (II), Y¹ is hydrogen. In another embodiment of Formula (II), Y¹ is $(CH_2)_t R^5$; R⁵ is optionally substituted phenyl or heteroaryl; and t is 1, 2, or 3. In another embodiment of Formula (II), Y¹ is $(CH_2)_t R^5$; R⁵ is phenyl; and t is 1, 2, or 3.

In one embodiment of Formula (II), Z¹ is aryl, heteroaryl, cycloalkyl, cycloalkenyl, heterocycloalkyl, or heterocycloalkenyl. In another embodiment of Formula (II), Z¹ is unsubstituted or substituted phenyl or pyridinyl. In another embodiment of Formula (II), Z¹ is unsubstituted or substituted phenyl.

In one embodiment of Formula (II), Z¹ is substituted with one or two or three or four or five independently selected R¹⁰, OR¹⁰, SR¹⁰, S(O)R¹⁰, SO₂R¹⁰, C(O)R¹⁰, C(O)OR¹⁰, OC(O)R¹⁰, NHR¹⁰, N(R¹⁰)₂, C(N)C(O)R¹⁰, C(O)NHR¹⁰, C(O)N(R¹⁰)₂, C(O)NHOH, C(O)NHOR¹⁰, C(O)NHSO₂R¹⁰, NHC(O)R¹⁰, NR¹⁰C(O)R¹⁰, NHC(O)OR¹⁰, NR¹⁰C(O)OR¹⁰, NR¹⁰C(O)NHR¹⁰, NR¹⁰C(O)N(R¹⁰)₂, NHC(O)NH₂, NHC(O)NHR¹⁰, NHC(O)N(R¹⁰)₂, SO₂NH₂, SO₂NHR¹⁰, SO₂N(R¹⁰)₂, NHS(O)R¹⁰, NHSO₂R¹⁰, NR¹⁰SO₂R¹⁰, NHSO₂NHR¹⁰, N(CH₃)SO₂N(CH₃)R¹⁰, (O), NH₂, NO₂, N₃, OH, F, Cl, Br, I, CN, CF₃, OCF₃, CF₂CF₃, OCF₂CF₃, C(O)H, C(O)OH, C(N)NH₂, C(N)NHR¹⁰, C(N)N(R¹⁰)₂, CNOH, CNOCH₃, or C(O)NH₂ substituents. In another embodiment of Formula (II), Z¹ is substituted with two independently selected SO₂R¹⁰, NHR¹⁰, CF₃, NO₂, or F. In another embodiment of Formula (II), Z¹ is substituted with NHR¹⁰ and SO₂R¹⁰, NO₂, CF₃, or F. In another embodiment of Formula (II), Z¹ is substituted with NHR¹⁰ and SO₂CF₃, SO₂CF₂Cl, CF₃, NO₂, or F. In one embodiment of Formula (II), Z¹ is substituted with NHR¹⁰ and SO₂CF₃, SO₂CF₂Cl, CF₃, NO₂, or F; wherein R¹⁰ is R¹⁴; R¹⁴ is alkyl which is unsubstituted or substituted with one or two or three independently selected OH, R¹⁵, OR¹⁵, SR¹⁵, or N(R¹⁵)₂ substituents; R¹⁵ is R¹⁶, R¹⁸ or R¹⁹; R¹⁶ is aryl; R¹⁸ is heterocycloalkyl; and R¹⁹ is alkyl.

In one embodiment of Formula (II), X¹ is heteroaryl; optionally substituted with one, two, three, or four R⁴;
Y¹ is hydrogen or $(CH_2)_t R^5$;
R⁴, at each occurrence, is halogen;
R⁵ is aryl;
t is 1, 2, or 3;
m is 0;
n is 0;
p is 0;
Z¹ is aryl;
wherein Z¹ is substituted with one or two or three or four or five independently selected SO₂R¹⁰, NHR¹⁰, NO₂, F, or CF₃, substituents;

$R^{10}$ is $R^{14}$;

$R^{14}$ is alkyl, which is unsubstituted or substituted with one or two or three independently selected $R^{15}$, $OR^{15}$, $SR^{15}$, $N(R^{15})_2$, OH, $CF_3$, F, or Cl substituents;

$R^{15}$ is $R^{16}$, $R^{18}$ or $R^{19}$;

$R^{16}$ is aryl;

$R^{18}$ is heterocycloalkyl; and $R^{19}$ is alkyl.

Still another embodiment pertains to a compound having Formula (II) selected from the group consisting of N-(1,3-benzothiazol-2-yl)-2-(6-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide;

N-(imidazo[1,2-a]pyridin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-a]pyrazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-b]pyridazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(6-fluoro-1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(1,3-benzothiazol-2-yl)-2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyrazin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-b]pyridazin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(6-fluoro-1,3-benzothiazol-2-yl)-1,2,3,4-tetrahydroisoquinoline-8-carboxamide;

N-(1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-b]pyridin-2-yl)-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-c]pyridin-2-yl)-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-a]pyrazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-b]pyridazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(6-fluoro-1,3-benzothiazol-2-yl)-2-[64 {[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide;

N-(6-fluoro-1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-b]pyridin-2-yl)-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-c]pyridin-2-yl)-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-a]pyrazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-b]pyridazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(6-fluoro-1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(1,3-benzothiazol-2-yl)-2-(6-{[(4-{[(2R)-4-(dimethylamino)-1-phenoxybutan-2-yl]amino}-3-nitrophenyl)sulfonyl]carbamoyl}pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyrazin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-b]pyridazin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyrazin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-b]pyridazin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

and therapeutically acceptable salts, metabolites, prodrugs, salts of metabolites, and salts of prodrugs thereof.

In another aspect, the present invention provides compounds of Formula (III)

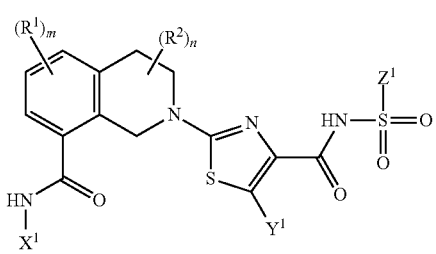

(III)

and therapeutically acceptable salts, metabolites, prodrugs, salts of metabolites, and salts of prodrugs thereof, wherein $X^1$, $Y^1$, $Z^1$, $R^1$, $R^2$, m, and n are as described herein for Formula (I).

One embodiment pertains to compounds and therapeutically acceptable salts, metabolites, prodrugs, salts of metabolites, and salts of prodrugs thereof, which are inhibitors of anti-apoptotic Bcl-xL proteins, the compounds having Formula (III)

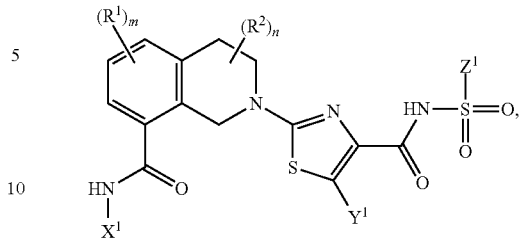

Formula (III)

wherein
$X^1$ is heteroaryl; optionally substituted with one, two, three, or four $R^4$;
$Y^1$ is hydrogen, $(CH_2)_tR^5$, $(CH_2)_tOR^5$, $(CH_2)_tNHR^5$, $(CH_2)_tN(R^5)_2$, or $(CH_2)_tSR^5$;
$R^1$, at each occurrence, is independently selected from the group consisting of halo, $C_{1-6}$ alkyl, $C_{2-6}$ alkenyl, $C_{2-6}$ alkynyl, and $C_{1-6}$ haloalkyl;
$R^2$, at each occurrence, is independently selected from the group consisting of deuterium, halo, $C_{1-6}$ alkyl, $C_{2-6}$ alkenyl, $C_{2-6}$ alkynyl, and $C_{1-6}$ haloalkyl;
two $R^2$ that are attached to the same carbon atom, together with said carbon atom, optionally form a ring selected from the group consisting of heterocycloalkyl, heterocycloalkenyl, cycloalkyl, and cycloalkenyl;
$R^4$, at each occurrence, is independently selected from the group consisting of $NR^6R^7$, $OR^6$, CN, $NO_2$, halogen, C(O)$OR^6$, C(O)$NR^6R^7$, $NR^6C(O)R^7$, $NR^6S(O)_2R^8$, $NR^6S(O)R^8$, $S(O)_2R^8$, $S(O)R^8$ and $R^8$;
$R^5$ is aryl or heterocyclyl; optionally substituted with one, two, three, or four substituents independently selected from the group consisting of $R^9$, $OR^9$, $SR^9$, $S(O)R^9$, $SO_2R^9$, C(O)$R^9$, CO(O)$R^9$, OC(O)$R^9$, OC(O)$OR^9$, $NH_2$, $NHR^9$, $N(R^9)_2$, $NHC(O)R^9$, $NR^9C(O)R^9$, $NHS(O)_2R^9$, $NR^9S(O)_2R^9$, NHC(O)$OR^9$, $NR^9C(O)OR^9$, NHC(O)$NH_2$, NHC(O)$NHR^9$, NHC(O)N($R^9)_2$, $NR^9C(O)NHR^9$, $NR^9C(O)N(R^9)_2$, C(O)$NH_2$, C(O)$NHR^9$, C(O)N($R^9)_2$, C(O)NHOH, C(O)$NHOR^9$, C(O)$NHSO_2R^9$, C(O)$NR^9SO_2R^9$, $SO_2NH_2$, $SO_2NHR^9$, $SO_2N(R^9)_2$, CO(O)H, C(O)H, OH, CN, $N_3$, $NO_2$, F, Cl, Br and I;
$R^6$ and $R^7$, at each occurrence, are each independently selected from the group consisting of hydrogen, $C_{1-4}$ alkyl, $C_{2-4}$ alkenyl, $C_{2-4}$ alkynyl, $C_{1-4}$ haloalkyl and $(CH_2)_{1-4}$ phenyl;
$R^8$, at each occurrence, is independently selected from the group consisting of $C_{1-4}$ alkyl, $C_{2-4}$ alkenyl, $C_{2-4}$ alkynyl and $C_{1-4}$ haloalkyl;
$R^6$ and $R^7$, or $R^6$ and $R^8$, at each occurrence, together with the atom to which each is attached, are optionally combined to form a heterocyclyl;
$R^9$, at each occurrence, is independently selected from the group consisting of $C_{1-6}$ alkyl, $C_{2-6}$ alkenyl, $C_{2-6}$ alkynyl, and $C_{1-6}$ haloalkyl;
t is 1, 2, or 3;
m is 0, 1, 2, or 3;
n is 0, 1, 2, 3, 4, 5, or 6;
$Z^1$ is aryl, heteroaryl, cycloalkyl, cycloalkenyl, heterocloalkyl, or heterocycloalkenyl;
wherein $Z^1$ is unsubstituted or substituted with one or two or three or four or five independently selected $R^{10}$, $OR^{10}$, $SR^{10}$, $S(O)R^{10}$, $SO_2R^{10}$, C(O)$R^{10}$, C(O)$OR^{19}$, OC(O)$R^{10}$, $NHR^{10}$, N($R^{10})_2$, C(N)C(O)$R^{10}$, C(O)$NHR^{10}$, C(O)N($R^{10})_2$, C(O)NHOH, C(O)$NHOR^{10}$, C(O)$NHSO_2R^{10}$, $NHC(O)R^{10}$, $NR^{10}C(O)R^{10}$, NHC(O)$OR^{19}$, $NR^{10}C(O)OR^{19}$, $NR^{10}C(O)NHR^{10}$, $NR^{10}C(O)N(R^{10})_2$, NHC(O)$NH_2$, NHC(O)$NHR^{10}$, NHC(O)N(R$^{10}$)$_2$, SO$_2$NH$_2$, SO$_2$NHR$^{10}$, SO$_2$N(R$^{19}$)$_2$, NHS(O)R$^{19}$, NHSO$_2$R$^{10}$, NR$^{10}$SO$_2$R$^{10}$, NHSO$_2$NHR$^{10}$, N(CH$_3$)SO$_2$N(CH$_3$)R$^{10}$, (O), NH$_2$, NO$_2$, N$_3$, OH, F, Cl, Br, I, CN, CF$_3$, OCF$_3$, CF$_2$CF$_3$, OCF$_2$CF$_3$, C(O)H, C(O)OH, C(N)NH$_2$, C(N)NHR$^{10}$, C(N)N(R$^{10}$)$_2$, CNOH, CNOCH$_3$, or C(O)NH$_2$ substituents;

R$^{10}$ is R$^{11}$, R$^{12}$, R$^{13}$ or R$^{14}$;

R$^{11}$ is aryl;

R$^{12}$ is heteroaryl;

R$^{13}$ is cycloalkyl, cycloalkenyl, cycloalkynyl, heterocloalkyl or heterocycloalkenyl;

R$^{14}$ is alkyl, alkenyl or alkynyl, each of which is unsubstituted or substituted with one or two or three independently selected R$^{15B}$, NC(R$^{15A}$)(R$^{15B}$), R$^{15}$, OR$^{15}$, SR$^{15}$, S(O)R$^{15}$, SO$_2$R$^{15}$, NHR$^{15}$, N(R$^{15}$)$_2$, C(O)R$^{15}$, C(O)NH$_2$, C(O)NHR$^{15}$, C(O)N(R$^{15}$)$_2$, NHC(O)R$^{15}$, NR$^{15}$C(O)R$^{15}$, NHSO$_2$R$^{15}$, NHC(O)OR$^{15}$, SO$_2$NH$_2$, SO$_2$NHR$^{15}$, SO$_2$N(R$^{15}$)$_2$, NHC(O)NH$_2$, NHC(O)NHR$^{15}$, NHC(O)CH(CH$_3$)NHC(O)CH(CH$_3$)NH$_2$, NHC(O)CH(CH$_3$)NHC(O)CH(CH$_3$)NHR$^{15}$, OH, (O), C(O)OH, N$_3$, CN, NH$_2$, CF$_3$, CF$_2$CF$_3$, F, Cl, Br or I substituents;

R$^{15A}$ and R$^{15B}$ are independently selected alkyl or, together with the N to which they are attached, R$^{15C}$;

R$^{15C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

R$^{15D}$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

R$^{15}$ is R$^{16}$, R$^{17}$, R$^{18}$ or R$^{19}$;

R$^{16}$ is aryl;

R$^{17}$ is heteroaryl;

R$^{18}$ is cycloalkyl, cycloalkenyl, heterocycloalkyl, or heterocycloalkenyl;

R$^{19}$ is alkyl, alkenyl or alkynyl, each of which is unsubstituted or substituted with one or two or three independently selected R$^{20}$, OR$^{20}$, SR$^{20}$, S(O)R$^{20}$, SO$_2$R$^{20}$, C(O)R$^{20}$, CO(O)R$^{20}$, OC(O)R$^{20}$, OC(O)OR$^{20}$, NH$_2$, NHR$^{20}$, N(R$^{20}$)$_2$, NHC(O)R$^{20}$, NR$^{20}$C(O)R$^{20}$, NHS(O)$_2$R$^{20}$, NR$^{20}$S(O)$_2$R$^{20}$, NHC(O)OR$^{20}$, NR$^{20}$C(O)OR$^{20}$, NHC(O)NH$_2$, NHC(O)NHR$^{20}$, NHC(O)N(R$^{20}$)$_2$, NR$^{20}$C(O)NHR$^{20}$, NR$^{20}$C(O)N(R$^{20}$)$_2$, C(O)NH$_2$, C(O)NHR$^{20}$, C(O)N(R$^{20}$)$_2$, C(O)NHOH, C(O)NHOR$^{20}$, C(O)NHSO$_2$R$^{20}$, C(O)NR$^{20}$SO$_2$R$^{20}$, SO$_2$NH$_2$, SO$_2$NHR$^{20}$, SO$_2$N(R$^{20}$)$_2$, C(O)H, C(O)OH, C(N)NH$_2$, C(N)NHR$^{20}$, C(N)N(R$^{20}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{20}$ is R$^{21}$, R$^{22}$, R$^{23}$ or R$^{24}$;

R$^{21}$ is aryl;

R$^{22}$ is heteroaryl;

R$^{23}$ is cycloalkane, cycloalkene, heterocycloalkane or heterocycloalkene;

R$^{24}$ is alkyl, alkenyl or alkynyl;

wherein the cyclic moieties represented by R$^{11}$, R$^{12}$, R$^{13}$, R$^{15C}$, R$^{15D}$, R$^{16}$, R$^{17}$, R$^{18}$, R$^{21}$, R$^{22}$, and R$^{23}$ are independently unsubstituted, further unsubstituted, substituted or further substituted with one or more independently selected R$^{25}$, OR$^{25}$, SR$^{25}$, S(O)R$^{25}$, SO$_2$R$^{25}$, C(O)R$^{25}$, CO(O)R$^{25}$, OC(O)R$^{25}$, OC(O)OR$^{25}$, NH$_2$, NHR$^{25}$, N(R$^{25}$)$_2$, NHC(O)R$^{25}$, NR$^{25}$C(O)R$^{25}$, NHS(O)$_2$R$^{25}$, NR$^{25}$S(O)$_2$R$^{25}$, NHC(O)OR$^{25}$, NR$^{25}$C(O)OR$^{25}$, NHC(O)NH$_2$, NHC(O)NHR$^{25}$, NHC(O)N(R$^{25}$)$_2$, NR$^{25}$C(O)NHR$^{25}$, NR$^{25}$C(O)N(R$^{25}$)$_2$, C(O)NH$_2$, C(O)NHR$^{25}$, C(O)N(R$^{25}$)$_2$, C(O)NHOH, C(O)NHOR$^{25}$, C(O)NHSO$_2$R$^{25}$, C(O)NR$^{25}$SO$_2$R$^{25}$, SO$_2$NH$_2$, SO$_2$NHR$^{25}$, SO$_2$N(R$^{25}$)$_2$, C(O)H, C(O)OH, C(N)NH$_2$, C(N)NHR$^{25}$, C(N)N(R$^{25}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{25}$ is R$^{26}$, R$^{27}$, R$^{28}$ or R$^{29}$;

R$^{26}$ is aryl;

R$^{27}$ is heteroaryl;

R$^{28}$ is cycloalkyl, cycloalkenyl, heterocycloalkyl or heterocycloalkenyl;

R$^{29}$ is alkyl, alkenyl, or alkynyl, each of which is unsubstituted or substituted with one or two or three independently selected R$^{30}$, OR$^{30}$, SR$^{30}$, S(O)R$^{30}$, SO$_2$R$^{30}$, C(O)R$^{30}$, CO(O)R$^{30}$, OC(O)R$^{30}$, OC(O)OR$^{30}$, NH$_2$, NHR$^{30}$, N(R$^{30}$)$_2$, NHC(O)R$^{30}$, NR$^{30}$C(O)R$^{30}$, NHS(O)$_2$R$^{30}$, NR$^{30}$S(O)$_2$R$^{30}$, NHC(O)OR$^{30}$, NR$^{30}$C(O)OR$^{30}$, NHC(O)NH$_2$, NHC(O)NHR$^{30}$, NHC(O)N(R$^{30}$)$_2$, NR$^{30}$C(O)NHR$^{30}$, NR$^{30}$C(O)N(R$^{30}$)$_2$, C(O)NH$_2$, C(O)NHR$^{30}$, C(O)N(R$^{30}$)$_2$, C(O)NHOH, C(O)NHOR$^{30}$, C(O)NHSO$_2$R$^{30}$, C(O)NR$^{30}$SO$_2$R$^{30}$, SO$_2$NH$_2$, SO$_2$NHR$^{30}$, SO$_2$N(R$^{30}$)$_2$, C(O)H, C(O)OH, C(N)NH$_2$, C(N)NHR$^{30}$, C(N)N(R$^{30}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{30}$ is R$^{31}$, R$^{32}$, R$^{33}$ or R$^{34}$;

R$^{31}$ is aryl;

R$^{32}$ is heteroaryl;

R$^{33}$ is cycloalkyl, cycloalkenyl, heterocycloalkyl or heterocycloalkenyl;

R$^{34}$ is alkyl, alkenyl, or alkenyl, each of which is unsubstituted or substituted with one or two or three independently selected R$^{35}$, OR$^{35}$, SR$^{35}$, S(O)R$^{35}$, SO$_2$R$^{35}$, C(O)R$^{35}$, CO(O)R$^{35}$, OC(O)R$^{35}$, OC(O)OR$^{35}$, NH$_2$, NHR$^{35}$, N(R$^{35}$)$_2$, NHC(O)R$^{35}$, NR$^{35}$C(O)R$^{35}$, NHS(O)$_2$R$^{35}$, NR$^{35}$S(O)$_2$R$^{35}$, NHC(O)OR$^{35}$, NR$^{35}$C(O)OR$^{35}$, NHC(O)NH$_2$, NHC(O)NHR$^{35}$, NHC(O)N(R$^{35}$)$_2$, NR$^{35}$C(O)NHR$^{35}$, NR$^{35}$C(O)N(R$^{35}$)$_2$, C(O)NH$_2$, C(O)NHR$^{35}$, C(O)N(R$^{35}$)$_2$, C(O)NHOH, C(O)NHOR$^{35}$, C(O)NHSO$_2$R$^{35}$, C(O)NR$^{35}$SO$_2$R$^{35}$, SO$_2$NH$_2$, SO$_2$NHR$^{35}$, SO$_2$N(R$^{35}$)$_2$, C(O)H, C(O)OH, C(N)NH$_2$, C(N)NHR$^{35}$, C(N)N(R$^{35}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{35}$ is alkyl, alkenyl, alkynyl, aryl, heteroaryl, cycloalkyl, cycloalkenyl, heterocycloalkyl or heterocycloalkenyl;

wherein the cyclic moieties represented by R$^{26}$, R$^{27}$, R$^{28}$, R$^{31}$, R$^{32}$, R$^{33}$, and R$^{35}$ are unsubstituted or substituted with one or more independently selected R$^{36}$, OR$^{36}$, SR$^{36}$, S(O)R$^{36}$, SO$_2$R$^{36}$, C(O)R$^{36}$, CO(O)R$^{36}$, OC(O)R$^{36}$, OC(O)OR$^{36}$, NH$_2$, NHR$^{36}$, N(R$^{36}$)$_2$, NHC(O)R$^{36}$, NR$^{36}$C(O)R$^{36}$, NHS(O)$_2$ R$^{36}$, NR$^{36}$S(O)$_2$R$^{36}$, NHC(O)OR$^{36}$, NR$^{36}$C(O)OR$^{36}$, NHC(O)NH$_2$, NHC(O)NHR$^{36}$, NHC(O)N(R$^{36}$)$_2$, NR$^{36}$C(O)NHR$^{36}$, NR$^{36}$C(O)N(R$^{36}$)$_2$, C(O)NH$_2$, C(O)NHR$^{36}$, C(O)N(R$^{36}$)$_2$, C(O)NHOH, C(O)NHOR$^{36}$, C(O)NHSO$_2$R$^{36}$, C(O)NR$^{36}$SO$_2$R$^{36}$, SO$_2$NH$_2$, SO$_2$NHR$^{36}$, SO$_2$N(R$^{36}$)$_2$, C(O)H, C(O)OH, C(N)NH$_2$, C(N)NHR$^{36}$, C(N)N(R$^{36}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

R$^{36}$ is R$^{37}$, R$^{38}$, R$^{30}$ or R$^{40}$;

R$^{37}$ is aryl;

R$^{38}$ is heteroaryl;

R$^{39}$ is cycloalkyl, cycloalkenyl, heterocycloalkyl or heterocycloalkenyl;

R$^{40}$ is alkyl, alkenyl, or alkenyl, each of which is unsubstituted or substituted with one or two or three independently selected R$^{41}$, OR$^{41}$, SR$^{41}$, S(O)R$^{41}$, SO$_2$R$^{41}$, C(O)R$^{41}$, CO(O)R$^{41}$, OC(O)R$^{41}$, OC(O)OR$^{41}$, NH$_2$, NHR$^{41}$, N(R$^{41}$)$_2$, NHC(O)R$^{41}$, NR$^{41}$C(O)R$^{41}$, NHS(O)$_2$R$^{41}$, N R$^{41}$S(O)$_2$R$^{41}$, NHC(O)OR$^{41}$, NR$^{41}$C(O)OR$^{41}$, NHC(O)NH$_2$, NHC(O)NHR$^{41}$, NHC(O)N(R$^{41}$)$_2$, NR$^{41}$C(O)NHR$^{41}$, NR$^{41}$C(O)N(R$^{41}$)$_2$, C(O)NH$_2$, C(O)NHR$^{41}$, C(O)N(R$^{41}$)$_2$, C(O)NHOH, C(O)NHOR$^{41}$, C(O)NHSO$_2$R$^{41}$, C(O)NR$^{41}$SO$_2$R$^{41}$, $SO_2NH_2$, $SO_2NHR^{41}$, $SO_2N(R^{41})_2$, C(O)H, C(O)OH, C(N)NH$_2$, C(N)NHR$^{41}$, C(N)N(R$^{41}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I substituents;

$R^{41}$ is alkyl, alkenyl, alkenyl, aryl, heteroaryl, cycloalkyl, cycloalkenyl, heterocycloalkyl, or heterocycloalkenyl; and the moieties represented by $R^{37}$, $R^{38}$, and $R^{39}$ are unsubstituted or substituted with one or more independently selected NH$_2$, C(O)NH$_2$, C(O)NHOH, SO$_2$NH$_2$, CF$_3$, CF$_2$CF$_3$, C(O)H, C(O)OH, C(N)NH$_2$, OH, (O), CN, N$_3$, NO$_2$, CF$_3$, CF$_2$CF$_3$, OCF$_3$, OCF$_2$CF$_3$, F, Cl, Br or I substituents.

In one embodiment of Formula (III), $X^1$ is heteroaryl; optionally substituted with one, two, three, or four $R^4$;

$Y^1$ is hydrogen, $(CH_2)_tR^5$, $(CH_2)_tOR^5$, $(CH_2)_tNHR^5$, $(CH_2)_tN(R^5)_2$, or $(CH_2)_tSR^5$;

$R^1$, at each occurrence, is independently selected from the group consisting of halo, C$_{1-6}$ alkyl, C$_{2-6}$ alkenyl, C$_{2-6}$ alkynyl, and C$_{1-6}$ haloalkyl;

$R^2$, at each occurrence, is independently selected from the group consisting of deuterium, halo, C$_{1-6}$ alkyl, C$_{2-6}$ alkenyl, C$_{2-6}$ alkynyl, and C$_{1-6}$ haloalkyl;

two $R^2$ that are attached to the same carbon atom, together with said carbon atom, optionally form a ring selected from the group consisting of heterocycloalkyl, heterocycloalkenyl, cycloalkyl, and cycloalkenyl;

$R^4$, at each occurrence, is independently selected from the group consisting of NR$^6$R$^7$, OR$^6$, CN, NO$_2$, halogen, C(O)OR$^6$, C(O)NR$^6$R$^7$, NR$^6$C(O)R$^7$, NR$^6$S(O)$_2$R$^8$, NR$^6$S(O)R$^8$, S(O)$_2$R$^8$, S(O)R$^8$ and R$^8$;

$R^5$ is aryl or heterocyclyl; optionally substituted with one, two, three, or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, CO(O)H, C(O)H, OH, CN, N$_3$, NO$_2$, F, Cl, Br and I;

$R^6$ and $R^7$, at each occurrence, are each independently selected from the group consisting of hydrogen, C$_{1-4}$ alkyl, C$_{2-4}$ alkenyl, C$_{2-4}$ alkynyl, C$_{1-4}$ haloalkyl and (CH$_2$)$_{1-4}$ phenyl;

$R^8$, at each occurrence, is independently selected from the group consisting of C$_{1-4}$ alkyl, C$_{2-4}$ alkenyl, C$_{2-4}$ alkynyl and C$_{1-4}$ haloalkyl;

$R^6$ and $R^7$, or $R^6$ and $R^8$, at each occurrence, together with the atom to which each is attached, are optionally combined to form a heterocyclyl;

$R^9$, at each occurrence, is independently selected from the group consisting of C$_{1-6}$ alkyl, C$_{2-6}$ alkenyl, C$_{2-6}$ alkynyl, and C$_{1-6}$ haloalkyl;

t is 1, 2, or 3;

m is 0, 1, 2, or 3;

n is 0, 1, 2, 3, 4, 5, or 6;

$Z^1$ is aryl, heteroaryl, cycloalkyl, cycloalkenyl, heterocycloalkyl, or heterocycloalkenyl;

wherein $Z^1$ is unsubstituted or substituted with one or two or three or four or five independently selected R$^{10}$, OR$^{10}$, SR$^{10}$, S(O)R$^{10}$, SO$_2$R$^{10}$, C(O)R$^{10}$, C(O)OR$^{19}$, OC(O)R$^{10}$, NHR$^{10}$, N(R$^{10}$)$_2$, C(N)C(O)R$^{10}$, C(O)NHR$^{10}$, C(O)N(R$^{10}$)$_2$, C(O)NHOH, C(O)NHOR$^{10}$, C(O)NHSO$_2$R$^{10}$, NHC(O)R$^{10}$, NR$^{10}$C(O)R$^{10}$, NHC(O)OR$^{19}$, NR$^{10}$C(O)OR$^{19}$, NR$^{10}$C(O)NHR$^{10}$, NR$^{10}$C(O)N(R$^{10}$)$_2$, NHC(O)NH$_2$, NHC(O)NHR$^{10}$, NHC(O)N(R$^{10}$)$_2$, SO$_2$NH$_2$, SO$_2$NHR$^{10}$, SO$_2$N(R$^{19}$)$_2$, NHS(O)R$^{19}$, NHSO$_2$R$^{10}$, NR$^{10}$SO$_2$R$^{10}$, NHSO$_2$NHR$^{10}$, N(CH$_3$)SO$_2$N(CH$_3$)R$^{10}$, (O), NH$_2$, NO$_2$, N$_3$, OH, F, Cl, Br, I, CN, CF$_3$, OCF$_3$, CF$_2$CF$_3$, OCF$_2$CF$_3$, C(O)H, C(O)OH, C(N)NH$_2$, C(N)NHR$^{10}$, C(N)N(R$^{10}$)$_2$, CNOH, CNOCH$_3$, or C(O)NH$_2$ substituents;

$R^{10}$ is $R^{11}$, $R^{12}$, $R^{13}$ or $R^{14}R^{11}$ is aryl;

$R^{12}$ is heteroaryl;

$R^{13}$ is cycloalkyl, cycloalkenyl, cycloalkynyl, heterocycloalkyl or heterocycloalkenyl;

$R^{14}$ is alkyl, alkenyl or alkynyl, each of which is unsubstituted or substituted with one or two or three independently selected $R^{15D}$, NC(R$^{15A}$)(R$^{15B}$), R$^{15}$, OR$^{15}$, SR$^{15}$, S(O)R$^{15}$, SO$_2$R$^{15}$, NHR$^{15}$, N(R$^{15}$)$_2$, C(O)R$^{15}$, C(O)NH$_2$, C(O)NHR$^{15}$, C(O)N(R$^{15}$)$_2$, NHC(O)R$^{15}$, NR$^{15}$C(O)R$^{15}$, NHSO$_2$R$^{15}$, NHC(O)OR$^{15}$, SO$_2$NH$_2$, SO$_2$NHR$^{15}$, SO$_2$N(R$^{15}$)$_2$, NHC(O)NH$_2$, NHC(O)NHR$^{15}$, NHC(O)CH(CH$_3$)NHC(O)CH(CH$_3$)NH$_2$, NHC(O)CH(CH$_3$)NHC(O)CH(CH$_3$)NHR$^{15}$, OH, (O), C(O)OH, N$_3$, CN, NH$_2$, CF$_3$, CF$_2$CF$_3$, F, Cl, Br or I substituents;

$R^{15A}$ and $R^{15B}$ are independently selected alkyl or, together with the N to which they are attached, $R^{15C}$;

$R^{15C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;

$R^{15D}$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;

$R^{15}$ is $R^{16}$, $R^{17}$, $R^{18}$ or $R^{19}$;

$R^{16}$ is aryl;

$R^{17}$ is heteroaryl;

$R^{18}$ is cycloalkyl, cycloalkenyl, heterocycloalkyl, or heterocycloalkenyl; and $R^{19}$ is alkyl.

In one embodiment of Formula (III), m is 0, 1, 2, or 3; and n is 0, 1, 2, 3, 4, 5, or 6. In another embodiment of Formula (III), n is 0 or 1. In another embodiment of Formula (III), n is 0 or 1; and each $R^2$ is independently deuterium or C$_{1-6}$ alkyl. In another embodiment of Formula (III), m, and n.

In one embodiment of Formula (III), $X^1$ is heteroaryl, which is optionally substituted with one, two, three or four $R^4$. In another embodiment of Formula (III), $X^1$ is heteroaryl, which is unsubstituted. In another embodiment of Formula (III), $X^1$ is heteroaryl, which is substituted with one $R^4$. In another embodiment of Formula (III), $X^1$ is heteroaryl, which is substituted with two $R^4$. In another embodiment of Formula (III), $X^1$ is heteroaryl, which is substituted with one $R^4$, and $R^4$ is OR$^6$ or halogen. In another embodiment of Formula (III), $X^1$ is heteroaryl, which is substituted with two $R^4$, and each $R^4$ is independently OR$^6$ or halogen. In another embodiment of Formula (III), $X^1$ is heteroaryl, which is substituted with one $R^4$, and $R^4$ is halogen. In another embodiment of Formula (III), $X^1$ is heteroaryl, which is substituted with two $R^4$, and each $R^4$ is independently F. In another embodiment of Formula (III), $X^1$ is heteroaryl, which is substituted with one $R^4$, and $R^4$ is F.

In one embodiment of Formula (III), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four $R^4$. In another embodiment of Formula (III), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are unsubstituted. In another embodiment of Formula (III), $X^1$ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5- b]pyridinyl, imidazo[1,2-a]pyrazinyl, or imidazo[1,2-b]pyridazinyl, which are substituted with one R⁴. In another embodiment of Formula (III), X¹ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R⁴. In another embodiment of Formula (III), X¹ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R⁴, and R⁴ is OR⁶ or halogen. In another embodiment of Formula (III), X¹ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R⁴, and each R⁴ is independently OR⁶ or halogen. In another embodiment of Formula (III), X¹ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R⁴, and R⁴ is Cl, F, or methoxy. In another embodiment of Formula (III), X¹ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with two R⁴, and each R⁴ is independently F. In another embodiment of Formula (III), X¹ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are substituted with one R⁴, and R⁴ is independently F.

In one embodiment of Formula (III), X¹ is benzo[d]thiazolyl, which is optionally substituted with one, two, three or four R⁴. In another embodiment of Formula (III), X¹ is benzo[d]thiazolyl, which is unsubstituted. In another embodiment of Formula (III), X¹ is benzo[d]thiazolyl, which is substituted with one R⁴. In another embodiment of Formula (III), X¹ is benzo[d]thiazolyl, which is substituted with two R⁴. In another embodiment of Formula (III), X¹ is benzo[d]thiazolyl, which is substituted with one R⁴, and R⁴ is OR⁶ or halogen. In another embodiment of Formula (III), X¹ is benzo[d]thiazolyl, which is substituted with two R⁴, and each R⁴ is independently OR⁶ or halogen. In another embodiment of Formula (III), X¹ is benzo[d]thiazolyl, which is substituted with one R⁴, and R⁴ is Cl, F, or methoxy. In another embodiment of Formula (III), X¹ is benzo[d]thiazolyl, which is substituted with two R⁴, and each R⁴ is independently F. In another embodiment of Formula (III), X¹ is benzo[d]thiazolyl, which is substituted with one R⁴, and R⁴ is independently F.

In one embodiment of Formula (III), X¹ is

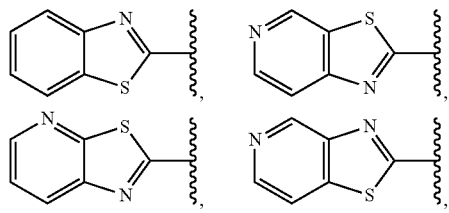

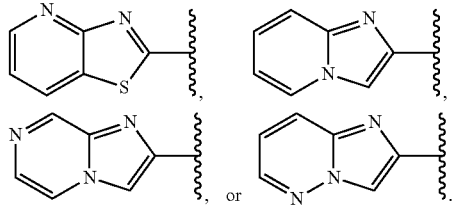

In another embodiment of Formula (III), X¹ is

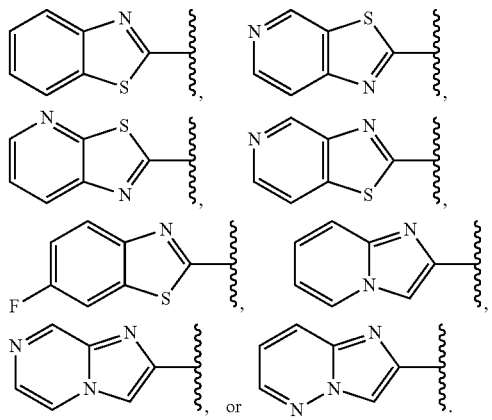

In another embodiment of Formula (III), X¹ is

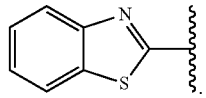 [SMILES: *c1nc2ccccc2s1]

In one embodiment of Formula (III), Y¹ is hydrogen, (CH₂)ₜR⁵, (CH₂)ₜOR⁵, (CH₂)ₜNHR⁵, (CH₂)ₜN(R⁵)₂, or (CH₂)ₜSR⁵. In another embodiment of Formula (III), Y¹ is hydrogen or (CH₂)ₜR⁵. In another embodiment of Formula (III), Y¹ is hydrogen. In another embodiment of Formula (III), Y¹ is (CH₂)ₜR⁵; R⁵ is optionally substituted phenyl or heteroaryl; and t is 1, 2, or 3. In another embodiment of Formula (III), Y¹ is (CH₂)ₜR⁵; R⁵ is phenyl; and t is 1, 2, or 3.

In one embodiment of Formula (III), Z¹ is aryl, heteroaryl, cycloalkyl, cycloalkenyl, heterocycloalkyl, or heterocycloalkenyl. In another embodiment of Formula (III), Z¹ is unsubstituted or substituted phenyl or pyridinyl. In another embodiment of Formula (III), Z¹ is unsubstituted or substituted phenyl.

In one embodiment of Formula (III), Z¹ is substituted with one or two or three or four or five independently selected R¹⁰, OR¹⁰, SR¹⁰, S(O)R¹⁰, SO₂R¹⁰, C(O)R¹⁰, C(O)OR¹⁰, OC(O)R¹⁰, NHR¹⁰, N(R¹⁰)₂, C(N)C(O)R¹⁰, C(O)NHR¹⁰, C(O)N(R¹⁰)₂, C(O)NHOH, C(O)NHOR¹⁰, C(O)NHSO₂R¹⁰, NHC(O)R¹⁰, NR¹⁰C(O)R¹⁰, NHC(O)OR¹⁰, NR¹⁰C(O)OR¹⁰, NR¹⁰C(O)NHR¹⁰, NR¹⁰C(O)N(R¹⁰)₂, NHC(O)NH₂, NHC(O)NHR¹⁰, NHC(O)N(R¹⁰)₂, SO₂NH₂, SO₂NHR¹⁰, SO₂N(R¹⁰)₂, NHS(O)R¹⁰, NHSO₂R¹⁰, NR¹⁰SO₂R¹⁰, NHSO₂NHR¹⁰, N(CH₃)SO₂N(CH₃)R¹⁰, (O), NH₂, NO₂, N₃, OH, F, Cl, Br, I, CN, CF₃, OCF₃, CF₂CF₃, OCF₂CF₃, C(O)H, C(O)OH, C(N)NH₂, C(N)NHR¹⁰, C(N)N(R¹⁰)₂, CNOH, CNOCH₃, or C(O)NH₂ substituents. In another embodiment of Formula (III), Z¹ is substituted with two independently selected $SO_2R^{10}$, $NHR^{10}$, $CF_3$, $NO_2$, or F. In another embodiment of Formula (III), $Z^1$ is substituted with $NHR^{10}$ and $SO_2R^{10}$, $NO_2$, $CF_3$, or F. In another embodiment of Formula (III), $Z^1$ is substituted with $NHR^{10}$ and $SO_2CF_3$, $SO_2CF_2Cl$, $CF_3$, $NO_2$, or F.

In one embodiment of Formula (III), $Z^1$ is substituted with $NHR^{10}$ and $SO_2CF_3$, $SO_2CF_2Cl$, $CF_3$, $NO_2$, or F; wherein $R^{10}$ is $R^{14}$; $R^{14}$ is alkyl which is unsubstituted or substituted with one or two or three independently selected OH, $R^{15}$, $OR^{15}$, $SR^{15}$, or $N(R^{15})_2$ substituents; $R^{15}$ is $R^{16}$, $R^{18}$ or $R^{19}$; $R^{16}$ is aryl; $R^{18}$ is heterocycloalkyl; and $R^{19}$ is alkyl.

In one embodiment of Formula (III), $X^1$ is heteroaryl; optionally substituted with one, two, three, or four $R^4$;
$Y^1$ is hydrogen or $(CH_2)_tR^5$;
$R^4$, at each occurrence, is halogen;
$R^5$ is aryl;
t is 1, 2, or 3;
m is 0;
n is 0;
$Z^1$ is aryl;
wherein $Z^1$ is substituted with one or two or three or four or five independently selected $SO_2R^{10}$, $NHR^{10}$, $NO_2$, F, or $CF_3$, substituents;
$R^{10}$ is $R^{14}$;
$R^{14}$ is alkyl, which is unsubstituted or substituted with one or two or three independently selected $R^{15}$, $OR^{15}$, $SR^{15}$, $N(R^{15})_2$, OH, $CF_3$, F, or Cl substituents;
$R^{15}$ is $R^{16}$, $R^{18}$ or $R^{19}$;
$R^{16}$ is aryl;
$R^{18}$ is heterocycloalkyl; and
$R^{19}$ is alkyl.

Still another embodiment pertains to a compound having Formula (III) selected from the group consisting of
N-(1,3-benzothiazol-2-yl)-2-(4-{[(4-{[(2R)-4-hydroxy-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide;
2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;
2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;
2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;
N-(imidazo[1,2-a]pyridin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;
N-(imidazo[1,2-a]pyrazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;
N-(imidazo[1,2-b]pyridazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;
N-(6-fluoro-1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;
N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;
2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;
2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;
2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyridin-2-yl)-1,2,3,4-tetrahydroisoquinoline-8-carboxamide;
2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;
2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;
2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;
N-(1,3-benzothiazol-2-yl)-2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;
2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;
2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;
2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;
2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(imidazo[1,2-a]pyrazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(imidazo[1,2-b]pyridazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(6-fluoro-1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

N-(6-fluoro-1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

N-(1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(imidazo[1,2-a]pyrazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(imidazo[1,2-b]pyridazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(6-fluoro-1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(1,3-benzothiazol-2-yl)-2-(4-{[(4-{[(2R)-4-(dimethylamino)-1-phenoxybutan-2-yl]amino}-3-nitrophenyl)sulfonyl]carbamoyl}-1,3-thiazol-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide; and therapeutically acceptable salts, metabolites, prodrugs, salts of metabolites, and salts of prodrugs thereof.

Pharmaceutical Compositions, Combination Therapies, Methods of Treatment, and Administration Another embodiment comprises pharmaceutical compositions comprising a compound having Formula (I) and an excipient.

Still another embodiment comprises methods of treating cancer in a mammal comprising administering thereto a therapeutically acceptable amount of a compound having Formula (I).

Still another embodiment comprises methods of treating autoimmune disease in a mammal comprising administering thereto a therapeutically acceptable amount of a compound having Formula (I).

Still another embodiment pertains to compositions for treating diseases during which anti-apoptotic Bcl-xL proteins are expressed, said compositions comprising an excipient and a therapeutically effective amount of the compound having Formula (I).

Still another embodiment pertains to methods of treating disease in a patient during which anti-apoptotic Bcl-xL proteins are expressed, said methods comprising administering to the patient a therapeutically effective amount of a compound having Formula (I).

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer, said compositions comprising an excipient and a therapeutically effective amount of the compound having Formula (I).

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, prostate cancer, small cell lung cancer or spleen cancer in a patient, said methods comprising administering to the patient a therapeutically effective amount of a compound having Formula (I).

Still another embodiment pertains to compositions for treating diseases during which are expressed anti-apoptotic Bcl-xL proteins, said compositions comprising an excipient and a therapeutically effective amount of the compound having Formula (I) and a therapeutically effective amount of one additional therapeutic agent or more than one additional therapeutic agent.

Still another embodiment pertains to methods of treating disease in a patient during which are expressed anti-apoptotic Bcl-xL proteins, said methods comprising administering to the patient a therapeutically effective amount of a compound having Formula (I) and a therapeutically effective amount of one additional therapeutic agent or more than one additional therapeutic agent.

Still another embodiment pertains to compositions for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer, said compositions comprising an excipient and a therapeutically effective amount of the compound having Formula (I) and a therapeutically effective amount of one additional therapeutic agent or more than one additional therapeutic agent.

Still another embodiment pertains to methods of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer or spleen cancer in a patient, said methods comprising administering to the patient a therapeutically effective amount of the compound having Formula (I) and a therapeutically effective amount of one additional therapeutic agent or more than one additional therapeutic agent.

Metabolites of compounds having Formula (I), produced by in vitro or in vivo metabolic processes, may also have utility for treating diseases associated with anti-apoptotic Bcl-xL proteins.

Certain precursor compounds which may be metabolized in vitro or in vivo to form compounds having Formula (I) may also have utility for treating diseases associated with expression of anti-apoptotic Bcl-xL proteins.

Compounds having Formula (I) may exist as acid addition salts, basic addition salts or zwitterions. Salts of the compounds are prepared during isolation or following purification of the compounds. Acid addition salts of the compounds are those derived from the reaction of the compounds with an acid. For example, the acetate, adipate, alginate, bicarbonate, citrate, aspartate, benzoate, benzenesulfonate, bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate, and undecanoate salts of the compounds are contemplated as being embraced by this invention. Basic addition salts of the compounds are those derived from the reaction of the compounds with the hydroxide, carbonate or bicarbonate of cations such as lithium, sodium, potassium, calcium, and magnesium.

The compounds having Formula (I) may be administered, for example, bucally, ophthalmically, orally, osmotically, parenterally (intramuscularly, intraperitoneally intrasternally, intravenously, subcutaneously), rectally, topically, transdermally or vaginally.

Therapeutically effective amounts of compounds having Formula (I) depend on the recipient of the treatment, the disorder being treated and the severity thereof, the composition containing the compound, the time of administration, the route of administration, the duration of treatment, the compound potency, its rate of clearance and whether or not another drug is co-administered. The amount of a compound of this invention having Formula (I) used to make a composition to be administered daily to a patient in a single dose or in divided doses is from about 0.03 to about 200 mg/kg body weight. Single dose compositions contain these amounts or a combination of submultiples thereof.

Compounds having Formula (I) may be administered with or without an excipient. Excipients include, for example, encapsulating materials or additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Excipients for preparation of compositions comprising a compound having Formula (I) to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, and mixtures thereof. Excipients for preparation of compositions comprising a compound of this invention having Formula (I) to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound of this invention having Formula (I) to be administered osmotically include, for example, chlorofluorohydrocarbons, ethanol, water and mixtures thereof. Excipients for preparation of compositions comprising a compound of this invention having Formula (I) to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound of this invention having Formula (I) to be administered rectally or vaginally include, for example, cocoa butter, polyethylene glycol, wax and mixtures thereof.

Compounds having Formula (I) are expected to be useful when used with alkylating agents, angiogenesis inhibitors, antibodies, antimetabolites, antimitotics, antiproliferatives, antivirals, aurora kinase inhibitors, other apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(41R)-3-(morpholin-4-yl)-1-((phenylsulfanyl)methyl)propyl) amino)-3-((trifluoromethyl)sulfonyl)benzenesulfonamide) or ABT-737 (i.e., N-(4-(4-((4'-chloro(1,1'-biphenyl)-2-yl) methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al, *Cancer Research* 2008, 68(9), 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-308, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19 Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCl-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARD10xANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzumab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Data

Determination of the utility of compounds having Formula (I) as binders to and inhibitors of anti-apoptotic Bcl-xL proteins was performed using the Time Resolved-Fluorescence Resonance Energy Transfer (TR-FRET) Assay. Tb-anti-GST antibody was purchased from Invitrogen (Catalog No. PV4216).

Probe Synthesis

All reagents were used as obtained from the vendor unless otherwise specified. Peptide synthesis reagents including diisopropylethylamine (DIEA), dichloromethane (DCM), N-methylpyrrolidone (NMP), 2-(1H-benzotriazole-1-yl)-1, 1,3,3-tetramethyluronium hexafluorophosphate (HBTU), N-hydroxybenzotriazole (HOBt) and piperidine were obtained from Applied Biosystems, Inc. (ABI), Foster City, Calif. or American Bioanalytical, Natick, Mass. Preloaded 9-Fluorenylmethyloxycarbonyl (Fmoc) amino acid cartridges (Fmoc-Ala-OH, Fmoc-Cys(Trt)-OH, Fmoc-Asp (tBu)-OH, Fmoc-Glu(tBu)-OH, Fmoc-Phe-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Asn(Trt)-OH, Fmoc-Pro-OH, Fmor-Gln(Trt)-OH, Fmoc-Arg(Pbf)-OH, Fmoc-Ser(tBu)-OH, Fmoc-Thr(tBu)-OH, Fmoc-Val-OH, Fmoc-Trp(Boc)-OH, Fmoc-Tyr(tBu)-OH) were obtained from ABI or Anaspec, San Jose, Calif. The peptide synthesis resin (Fmoc-Rink amide MBHA resin) and Fmoc-Lys(Mtt)-OH were obtained from Novabiochem, San Diego, Calif. Single-isomer 6-carboxyfluorescein succinimidyl ester (6-FAM-NHS) was obtained from Anaspec. Trifluoroacetic acid (TFA) was obtained from Oakwood Products, West Columbia, S.C. Thioanisole, phenol, triisopropylsilane (TIS), 3,6-dioxa-1,8-octanedithiol (DODT) and isopropanol were obtained from Aldrich Chemical Co., Milwaukee, Wis. Matrix-assisted laser desorption ionization mass-spectra (MALDI-MS) were recorded on an Applied Biosystems Voyager DE-PRO MS). Electrospray mass-spectra (ESI-MS) were recorded on Finnigan SSQ7000 (Finnigan Corp., San Jose, Calif.) in both positive and negative ion mode.

General Procedure for Solid-Phase Peptide Synthesis (SPPS)

Peptides were synthesized with, at most, 250 μmol preloaded WANG resin/vessel on an ABI 433A peptide synthesizer using 250 μmol scale FASTMOC™ coupling cycles. Preloaded cartridges containing 1 mmol standard Fmoc-amino acids, except for the position of attachment of the fluorophore, where 1 mmol Fmoc-Lys(Mtt)-OH was placed in the cartridge, were used with conductivity feedback monitoring. N-terminal acetylation was accomplished by using 1 mmol acetic acid in a cartridge under standard coupling conditions.

Removal of 4-Methyltrityl (Mtt) from Lysine

The resin from the synthesizer was washed thrice with DCM and kept wet. 150 mL of 95:4:1 dichloromethane:triisopropylsilane:trifluoroacetic acid was flowed through the resin bed over 30 minutes. The mixture turned deep yellow then faded to pale yellow. 100 mL of DMF was flowed through the bed over 15 minutes. The resin was then washed thrice with DMF and filtered. Ninhydrin tests showed a strong signal for primary amine

Resin Labeling with 6-Carboxyfluorescein-NHS (6-FAM-NHS)

The resin was treated with 2 equivalents 6-FAM-NHS in 1% DIEA/DMF and stiffed or shaken at ambient temperature overnight. When complete, the resin was drained, washed thrice with DMF, thrice with (1×DCM and 1× methanol) and dried to provide an orange resin that was negative by ninhydrin test.

General Procedure For Cleavage And Deprotection Of Resin-Bound Peptide

Peptides were cleaved from the resin by shaking for 3 hours at ambient temperature in a cleavage cocktail consisting of 80% TFA, 5% water, 5% thioanisole, 5% phenol, 2.5% TIS, and 2.5% EDT (1 mL/0.1 g resin). The resin was removed by filtration and rinsing twice with TFA. The TFA was evaporated from the filtrates, and product was precipitated with ether (10 mL/0.1 g resin), recovered by centrifugation, washed twice with ether (10 mL/0.1 g resin) and dried to give the crude peptide.

General Procedure for Purification Of Peptides

The crude peptides were purified on a Gilson preparative HPLC system running Unipoint® analysis software (Gilson, Inc., Middleton, Wis.) on a radial compression column containing two 25×100 mm segments packed with Delta-Pak™ C18 15 µm particles with 100 Å pore size and eluted with one of the gradient methods listed below. One to two milliliters of crude peptide solution (10 mg/mL in 90% DMSO/water) was purified per injection. The peaks containing the product(s) from each run were pooled and lyophilized. All preparative runs were run at 20 mL/min with eluents as buffer A: 0.1% TFA-water and buffer B: acetonitrile.

General Procedure for Analytical HPLC

Analytical HPLC was performed on a Hewlett-Packard 1200 series system with a diode-array detector and a Hewlett-Packard 1046A fluorescence detector running HPLC 3D CHEMSTATION software version A.03.04 (Hewlett-Packard. Palo Alto, Calif.) on a 4.6×250 mm YMC column packed with ODS-AQ 5 µm particles with a 120 Å pore size and eluted with one of the gradient methods listed below after preequilibrating at the starting conditions for 7 minutes. Eluents were buffer A: 0.1% TFA-water and buffer B: acetonitrile. The flow rate for all gradients was 1 mL/min.

F-Bak: Peptide Probe Acetyl-GQVGRQLAIIGDK(6-FAM)INR-NH$_2$(SEQ ID NO: 1)

Fmoc-Rink amide MBHA resin was extended using the general peptide synthesis procedure to provide the protected resin-bound peptide (1.020 g). The Mtt group was removed, labeled with 6-FAM-NHS and cleaved and deprotected as described hereinabove to provide the crude product as an orange solid (0.37 g). This product was purified by RP-HPLC. Fractions across the main peak were tested by analytical RP-HPLC, and the pure fractions were isolated and lyophilized, with the major peak providing the title compound (0.0802 g) as a yellow solid; MALDI-MS m/z=2137.1 [(M+H)$^+$].

Alternative Synthesis of Peptide Probe F-Bak: Acetyl-GQVGRQLAIIGDK(6-FAM)INR-NH$_2$(SEQ ID NO: 1)

The protected peptide was assembled on 0.25 mmol Fmoc-Rink amide MBHA resin (Novabiochem) on an Applied Biosystems 433A automated peptide synthesizer running FASTMOCT™ coupling cycles using pre-loaded 1 mmol amino acid cartridges, except for the fluorescein(6-FAM)-labeled lysine, where 1 mmol Fmoc-Lys(4-methyltrityl) was weighed into the cartridge. The N-terminal acetyl group was incorporated by putting 1 mmol acetic acid in a cartridge and coupling as described hereinabove. Selective removal of the 4-methyltrityl group was accomplished with a solution of 95:4:1 DCM:TIS:TFA (v/v/v) flowed through the resin over 15 minutes, followed by quenching with a flow of dimethylformamide. Single-isomer 6 carboxyfluorescein-NHS was reacted with the lysine side-chain in 1% DIEA in N,N-dimethylformamide and confirmed complete by ninhydrin testing. The peptide was cleaved from the resin and side-chains deprotected by treating with 80:5:5:5:2.5:2.5 TFA/water/phenol/thioanisole/triisopropylsilane: 3,6-dioxa-1,8-octanedithiol (v/v/v/v/v/v), and the crude peptide was recovered by precipitation with diethyl ether. The crude peptide was purified by reverse-phase high-performance liquid chromatography, and its purity and identity were confirmed by analytical reverse-phase high-performance liquid chromatography and matrix-assisted laser-desorption mass-spectrometry (m/z=2137.1 ((M+H)+)).

Time Resolved-Fluorescence Resonance Energy Transfer (TR-FRET) Assay

The measurement of competition of compounds of Formula (I) with F-Bak for a Bcl-2 family protein (Bcl-xL) binding site using a Time Resolved Fluorescence Resonance Energy Transfer (TR-FRET) binding assay:

Test compounds were serially diluted in DMSO starting at 50 µM (2× starting concentration; 10% DMSO) and 10 µL transferred into a 384-well plate. Then 10 µL of a protein/probe/antibody mix is added to each well at final concentrations listed in Table 1.

TABLE 1

| Protein | Probe | Protein (nM) | Probe (nM) | Antibody | Antibody (nM) |
|---|---|---|---|---|---|
| GST-Bcl-xL | F-Bak (GQVGRQLAIIGDK(6-FAM)INR-amide) SEQ ID NO: 1 | 1 | 100 | Tb-anti-GST | 1 |

The samples are then mixed on a shaker for 1 minute then incubated for an additional 2 hours at room temperature. For each assay plate, a probe/antibody and protein/antibody/probe mixture were included as a negative and a positive control, respectively. Fluorescence was measured on the ENVISION plate reader (Perkin Elmer) using a 340/35 nm excitation filter and 520/525 (F-Bak) and 495/510 nm (Tb-labeled anti-his antibody) emission filters. Dissociation constants ($K_i$) were determined using Wang's equation (Wang, Z. X. An 20 exact mathematical expression for describing competitive binding of two different ligands to protein molecule. FEBS Lett. 1995 360:111-114). The TR-FRET assay can be performed in the presence of varying concentrations of human serum (HS) or fetal bovine serum (FBS). TR-FRET assay results ($K_i$ in nanomolar) for representative compounds of Formula (I) are provided below in Table 2.

For comparison, the measurement of the competition of compounds of Formula (I) for other Bcl-2 family protein binding sites (e.g., Bcl-2) using the TR-FRET binding assay was accomplished by substituting GST-Bcl-xL in the TR-FRET assay with other GST-labeled protein, e.g., GST-Bcl-2, prepared in-house.

In one embodiment, compounds of Formula (I) selectively inhibit the Bcl-2 family protein, Bcl-$x_L$, over other Bcl-2 family proteins, such as Bcl-2. For comparison, data ($K_i$ in micromolar) from the measurement of the competition by certain compounds of Formula (I) (i.e., Examples 1, 2, 3, 4, 5, 6, 7, 8, 9, 10, 12, 13, 14 and 15) with F-Bak for the Bcl-2 binding site using the TR-FRET binding assay are 0.031, 0.19, >1.2, 0.395, >1.2, 0.724, 0.230, >1.2, 0.106, >1.2, 0.034, 0.322, 0.092, 0.120 and >0.120, respectively.

FL5.12 Cellular Assay

The efficacy of the compounds of Formula (I) can also be determined in cell-based killing assays using a variety of cell lines and mouse tumor models. For example, their activity on cell viability can be assessed on a panel of cultured tumorigenic and non-tumorigenic cell lines, as well as primary mouse or human cell populations. In one exemplary set of conditions, mouse FL5.12 cells transfected with Bcl-XL were cultured under standard conditions in RPMI with 2 mM glutamine, 1% 100 mM sodium pyruvate, 2% 1 M HEPES, 4 µL/L of β-mercaptoethanol, 1% penicillinstreptomycin, 10% FBS, and 10% WEHI-3B conditioned media (for IL-3). For assaying the compound activity, the cells were exchanged into an IL-3-depleted deprivation media, which was identical to the growth media except for the absence of FBS and WEHI-3B conditional media, for 2 days. Then the cells were exchanged to 3% FBS assay media (RPMI with 2 mM glutamine, 1% 100 mM sodium pyruvate, 2% 1 M HEPES, 4 µL/L of β-mercaptoethanol, 1% penicillinstreptomycin, 3% FBS). Compounds in series dilutions were added, and the cells were cultured for 24 hours. Compounds in series dilutions were added, and the cells were cultured for 24 hours. Cell viability was assayed using the CellTiter-Glo assay (Promega Corp., Madison, Wis.) according to the manufacturer instructions. Individual determinations were the result of duplicate values. Cell viability assay results ($EC_{50}$ in nanomolar) for representative compounds are provided below in Table 2.

TABLE 2

| | In Vitro Data | |
|---|---|---|
| EX | TR-FRET binding Bcl-xL Ki (nM) | FL5.12 Bcl-xL, -IL3, EC 50 (nM) |
| 1 | 0.1 | 56 |
| 2 | 0.1 | 12 |
| 3 | 12 | >1,000 |
| 4 | 9 | >1,000 |
| 5 | 48 | >1,000 |
| 6 | 17 | >1,000 |
| 7 | 1.7 | >1,000 |
| 8 | 11 | >1,000 |
| 9 | 41 | >1,000 |
| 10 | 0.14 | n.d. |
| 11 | 0.06 | 22 |
| 12 | 0.04 | 3 |
| 13 | 0.8 | 94 |
| 14 | 0.2 | n.d |
| 15 | 5 | n.d. |

EX = Example,
n.d. = no data available

Molt-4 Cellular Assay

Molt-4 (ATCC, Manassas, Va.) human acute lymphoblastic leukemia cells were plated 50,000 cells per well in 96-well tissue culture plates in a total volume of 100 µL tissue culture medium supplemented with 10% human serum (Invitrogen, Carlsbad, Calif.) and treated with a 3-fold serial dilution of the compounds of interest from 5 µM to 0.020 µL. Each concentration was tested in duplicate at least 3 separate times. The number of viable cells following 48 hours of compound treatment was determined using the CellTiter 96® Aqueous non-radioactive cell proliferation MTS assay according to manufacturer's recommendations (Promega Corp., Madison, Wis.). Molt-4 cell viability results (i.e. $EC_{50}$ in micromolar) for certain compounds of Formula (I), (i.e., Examples 1, 2, 3, 4, 5, 6, 7, 8, 9, 11, 12, 13, and 14), are >5, 0.082, >5, >5, >5, >5, >5, >5, >5, >5, >5, 0.18, >5, and >5, respectively.

Data in Table 2 and cited Molt-4 data show the utility of compounds of the invention to functionally inhibit anti-apoptotic Bcl-xL protein in a cellular context. The ability of compounds to kill FL5.12 cells over-expressing Bcl-xL or human tumor cell lines that are dependant upon Bcl-xL such as Molt-4 cells is a direct measure of the compound's ability to inhibit anti-apoptotic Bcl-xL protein function. Compounds of the invention are very effective in killing FL5.12 cells over-expressing Bcl-xL or human tumor cell lines that are dependant upon Bcl-xL such as Molt-4 cells as demonstrated by low $EC_{50}$ values.

Overexpression of Bcl-xL proteins correlates with resistance to chemotherapy, clinical outcome, disease progression, overall prognosis or a combination thereof in various cancers and disorders of the immune system. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synoviomia, sweat gland carcinoma, testicular cancer (including germ cell testicular cancer), thyroid cancer, Waldenstrm's macroglobulinemia, testicular tumors, uterine cancer, Wilms' tumor and the like.

It is also expected that compounds having Formula (I) would inhibit growth of cells expressing Bcl-xL proteins derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia greata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GB S) infection, Grave's disease, haemosiderosis associated lung disease, hairy cell leukemia, hairy cell leukemia, Hallervorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, *legionella*, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multisystem disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, mycobacterium avium intracellulare, mycobacterium tuberculosis, myelodyplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epidydimitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease, Raynoud's disease, Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthopathy, sporadic, polyglandular deficiency type I, sporadic polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *yersinia* and *salmonella*-associated arthropathy and the like.

Schemes and Experimentals

The following abbreviations have the meanings indicated. ADDP means 1,1'-(azodicarbonyl)dipiperidine; AD-mix-β means a mixture of $(DHQD)_2PHAL$, $K_3Fe(CN)_6$, $K_2CO_3$, and $K_2SO_4$; 9-BBN means 9-borabicyclo(3.3.1)nonane; Boc means tert-butoxycarbonyl; $(DHQD)_2PHAL$ means hydroquinidine 1,4-phthalazinediyldiethyl ether; DBU means 1,8-diazabicyclo[5.4.0]undec-7-ene; DIBAL means diisobutylaluminum hydride; DIEA means diisopropylethylamine; DMAP means N,N-dimethylaminopyridine; DMF means N,N-dimethylformamide; dmpe means 1,2-bis(dimethylphosphino)ethane; DMSO means dimethylsulfoxide; dppb means 1,4-bis(diphenylphosphino)-butane; dppe means 1,2-bis(diphenylphosphino)ethane; dppf means 1,1'-bis(diphenylphosphino)ferrocene; dppm means 1,1-bis(diphenylphosphino)methane; EDACHClmeans 1-(3-dimethylaminopropyl)-3-ethylcarbodiimide hydrochloride; Fmoc means fluorenylmethoxycarbonyl; HATU means O-(7-azabenzotriazol-1-yl)-N,N'N'N'-tetramethyluronium hexafluorophosphate; HMPA means hexamethylphosphoramide; IPA means isopropyl alcohol; $MP-BH_3$ means macroporous triethylammonium methylpolystyrene cyanoborohydride; TEA means triethylamine; TFA means trifluoroacetic acid; THF means tetrahydrofuran; NCS means N-chlorosuccinimide; NMM means N-methylmorpholine; NMP means N-methylpyrrolidine; $PPh_3$ means triphenylphosphine.

The following schemes are presented to provide what is believed to be the most useful and readily understood description of procedures and conceptual aspects of this invention. Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Schemes

Scheme 1

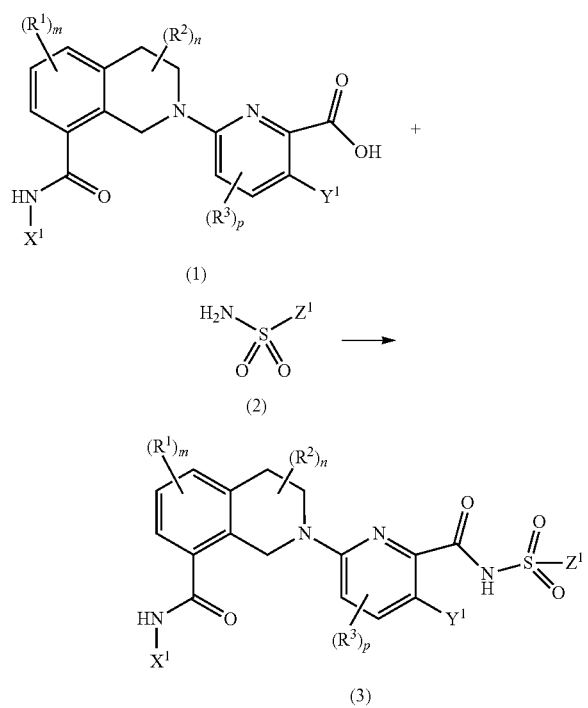

As shown in Scheme 1, compounds of formula (I) wherein $X^1, Y^1, R^1, R^2, R^3$, m, n, and p are as described herein, can be coupled with compounds of formula (2) wherein $Z^1$ is as described herein, in the presence of 4-(dimethylamino)pyridine and 1-ethyl-3-[3-(dimethylamino)propyl]-carbodiimide hydrochloride to provide compounds of formula (3) which are representative of compounds of formula (I). The reaction is typically performed at ambient temperature in a solvent such as, but not limited to, dichloromethane.

Scheme 2

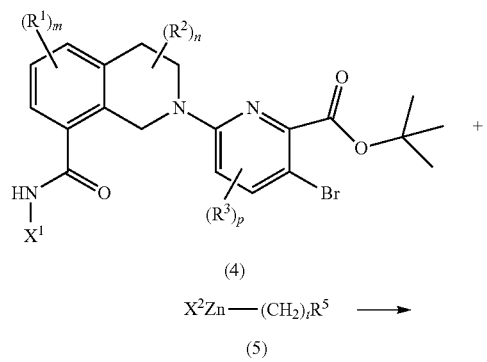

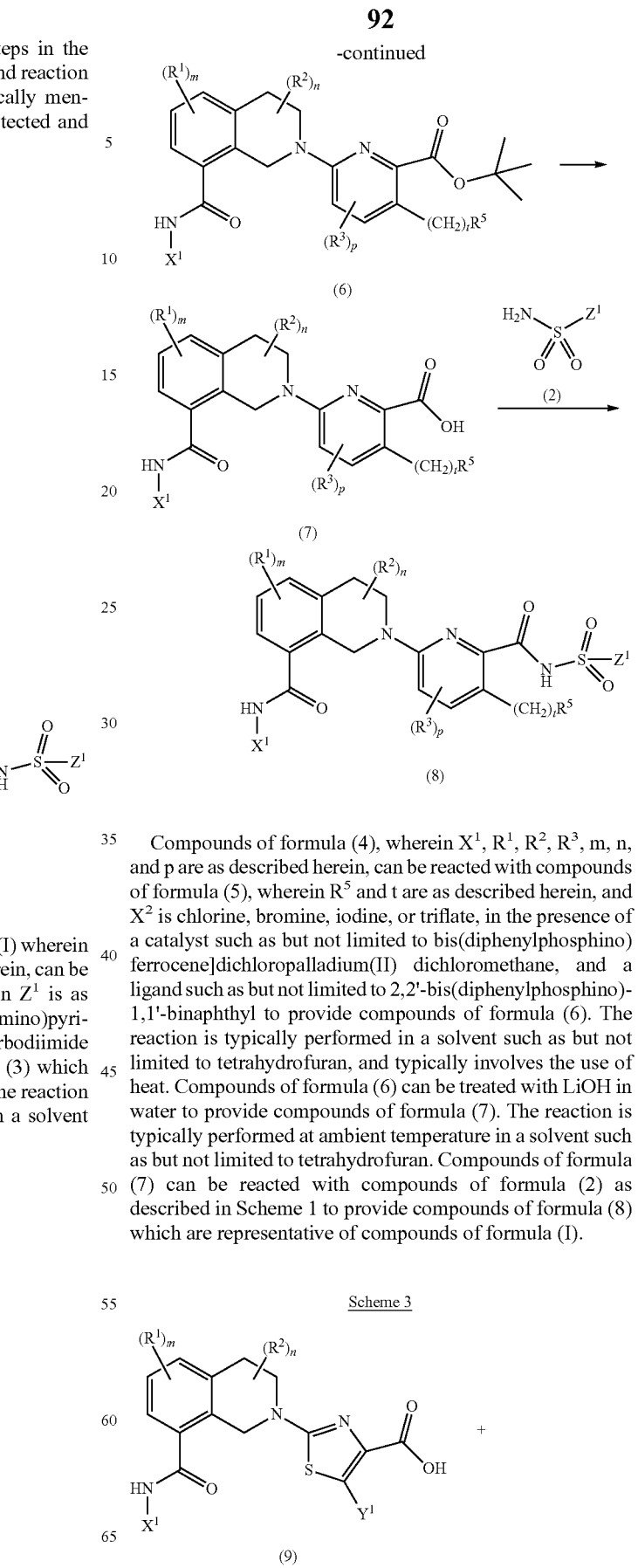

Compounds of formula (4), wherein $X^1$, $R^1$, $R^2$, $R^3$, m, n, and p are as described herein, can be reacted with compounds of formula (5), wherein $R^5$ and t are as described herein, and $X^2$ is chlorine, bromine, iodine, or triflate, in the presence of a catalyst such as but not limited to bis(diphenylphosphino)ferrocene]dichloropalladium(II) dichloromethane, and a ligand such as but not limited to 2,2'-bis(diphenylphosphino)-1,1'-binaphthyl to provide compounds of formula (6). The reaction is typically performed in a solvent such as but not limited to tetrahydrofuran, and typically involves the use of heat. Compounds of formula (6) can be treated with LiOH in water to provide compounds of formula (7). The reaction is typically performed at ambient temperature in a solvent such as but not limited to tetrahydrofuran. Compounds of formula (7) can be reacted with compounds of formula (2) as described in Scheme 1 to provide compounds of formula (8) which are representative of compounds of formula (I).

Scheme 3

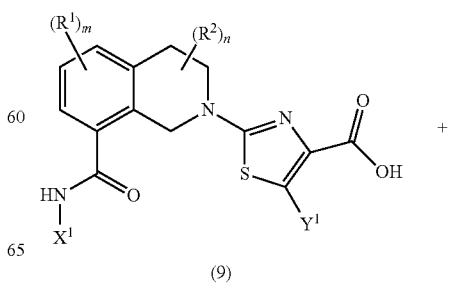

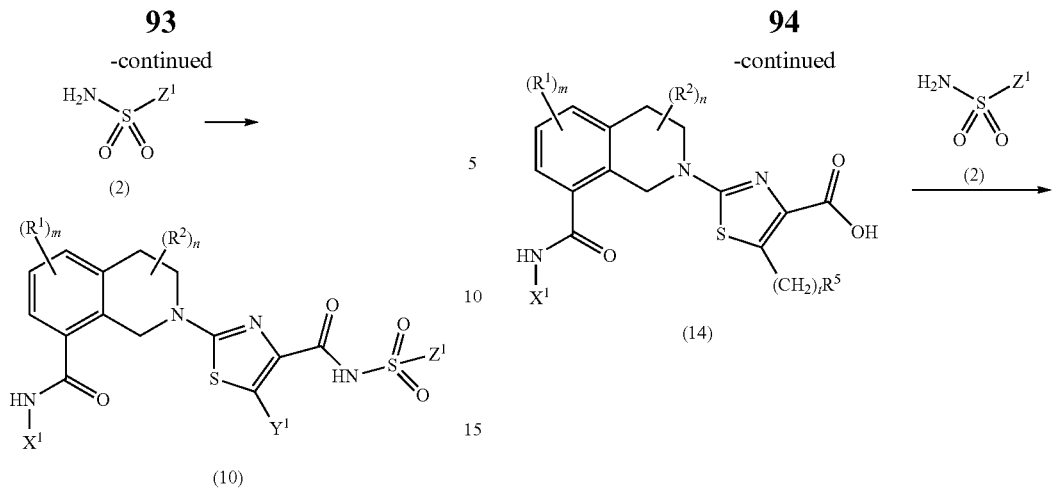

Compounds of formula (9), wherein $X^1$, $Y^1$, $R^1$, m, and n are as described herein, can be coupled with compounds of formula (2) wherein $Z^1$ is as described herein, in the presence of 4-(dimethylamino)pyridine and 1-ethyl-3-[3-(dimethylamino)propyl]-carbodiimide hydrochloride to provide compounds of formula (10) which are representative of compounds of formula (I). The reaction is typically performed at ambient temperature in a solvent such as but not limited to dichloromethane.

Scheme 4

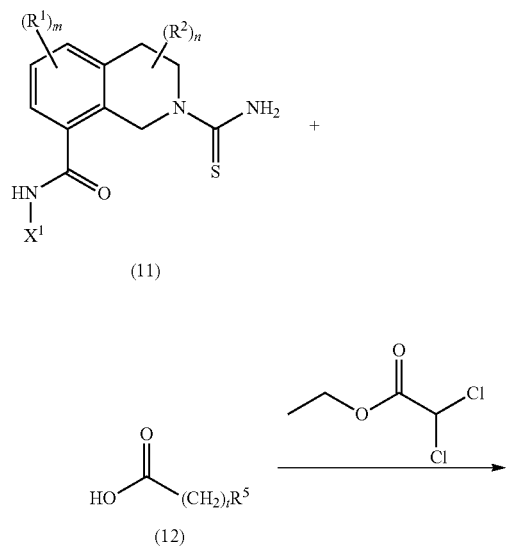

As shown in Scheme 4, an ethanolic mixture of ethyl 2,2-dichloroacetate and compounds of formula (12), wherein $R^5$ and t are as described herein, treated with a base such as but not limited to sodium hydride, can be reacted with compounds of formula (11), wherein $X^1$, $R^1$, $R^2$, m, and n are as described herein, to provide compounds of formula (13). The reaction is typically performed at a reduced temperature in a solvent, such as, but not limited to, N,N-dimethylformamide. Compounds of formula (13) can be treated with LiOH in water to provide compounds of formula (14). The reaction is typically performed at ambient temperature in a solvent such as, but not limited to, tetrahydrofuran. Compounds of formula (15), which are representative of the compounds of formula (I), can be prepared by coupling with compounds of formula (2) wherein $Z^1$ is as described herein, in the presence of 4-(dimethylamino)pyridine and 1-ethyl-3-[3-(dimethylamino)propyl]-carbodiimide hydrochloride. The reaction is typically performed at ambient temperature in a solvent such as but not limited to dichloromethane.

Scheme 5

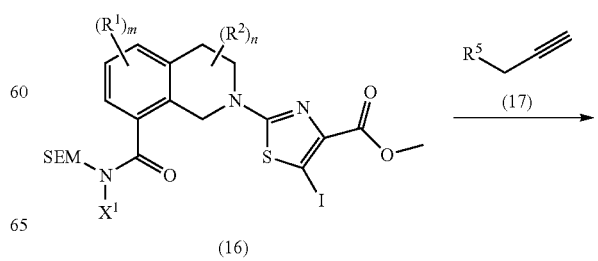

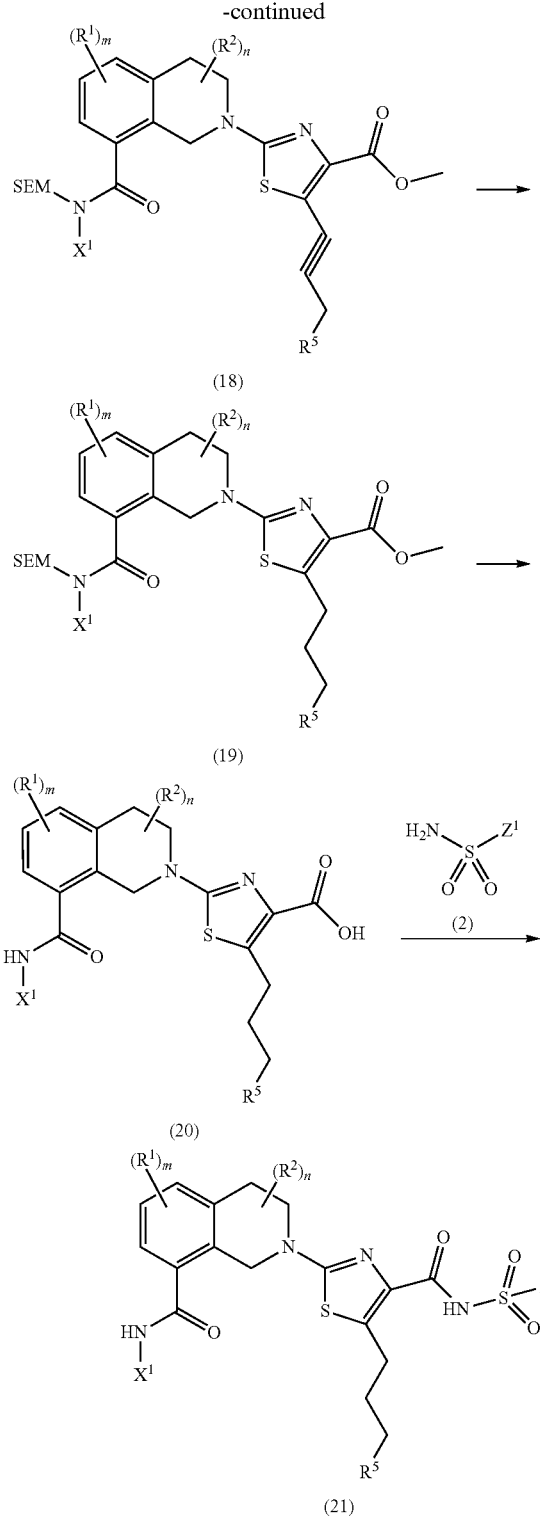

Compounds of formula (16), wherein $X^1$, $R^1$, $R^2$, m, and n are as described herein, and wherein SEM is a silyl ether protecting group, can be reacted with compounds of formula (17) wherein $R^5$ is as described herein, in the presence of a palladium catalyst such as, but not limited to, bis(triphenylphosphine)palladium (II) dichloride, a copper salt catalyst such as, but not limited to CuI, and a base such as but not limited to triethylamine, provide compounds of formula (18). The reaction is typically performed at ambient temperature and may be performed in a solvent such as, but not limited to, tetrahydrofuran. Compounds of formula (19) can be prepared by reacting compounds of formula (18) with hydrogen in the presence of Pd/C. The reaction is typically performed at ambient temperature in a solvent such as but not limited to ethyl acetate. Compounds of formula (19) can be treated with LiOH in water to provide compounds of formula (20). The reaction is typically performed at ambient temperature in tetrahydrofuran. Compounds of formula (21), which are representative of the compounds of this invention, can be prepared by coupling with compounds of formula (2) wherein $Z^1$ is as described herein, in the presence of 4-(dimethylamino) pyridine and 1-ethyl-3-[3-(dimethylamino)propyl]-carbodiimide hydrochloride. The reaction is typically performed at ambient temperature in a solvent such as but not limited to dichloromethane.

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

EXAMPLES

Example 1

N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide Example 1A 2-(8-(benzo[d]thiazol-2-ylcarbamoyl)-3,4-dihydroisoquinolin-2(1H)-yl)thiazole-4-carboxylic acid To a solution of 2-(tert-butoxycarbonyl)-1,2,3,4-tetrahydroisoquinoline-8-carboxylic acid (6.8 g) and benzo[d]thiazol-2-amine (5.52 g) in dichloromethane (80 mL) was added 1-ethyl-3-[3-(dimethylamino)propyl]-carbodiimide hydrochloride (9.4 g) and 4-(dimethylamino)pyridine (6 g). The mixture was stirred overnight, diluted with dichloromethane (400 mL) and washed with 5% aqueous HCl and brine. The organic layer was dried over $Na_2SO_4$ and concentrated to give the titled product.

Example 1B (R)-4-(4-(dimethylamino)-1-(phenylthio)butan-2-ylamino)-3-nitrobenzenesulfonamide To a solution of Example 1A (8.5 g) in dichloromethane (80 mL) was added 2N HCl in ether (80 mL). The reaction mixture was stirred overnight and concentrated to give the title product.

Example 1C methyl 2-(8-(benzo[d]thiazol-2-ylcarbamoyl)-3,4-dihydroisoquinolin-2(1H)-yl)thiazole-4-carboxylate To a solution of Example 1B (5.3 g) and methyl 2-chlorothiazole-4-carboxylate (2.5 g) in N,N-dimethylacetamide (60 mL) was added Cs$_2$CO$_3$ (25 g). The mixture was stirred at 50° C. overnight, cooled to room temperature and acidified with 5% aqueous HCl. The resulting mixture was extracted with dichloromethane and washed with water and brine. The organic layer was dried over Na$_2$SO4 and concentrated. The residue was purified by flash chromatography, eluting with 5% methanol in dichloromethane, to give the title compound.

Example 1D 2-(8-(benzo[d]thiazol-2-ylcarbamoyl)-3,4-dihydroisoquinolin-2(1H)-yl)thiazole-4-carboxylic acid To a solution of Example 1C (180 mg) in tetrahydrofuran (4 mL) and methanol (2 mL) was added 2N NaOH (2 mL). The mixture was stirred at 50° C. for 4 hours, cooled and neutralized by the slow addition of 5% aqueous HCl. The precipitates were collected by filtration and dried to provide the title compound.

Example 1E (R)—N,N-dimethyl-3-(2-nitro-4-sulfamoylphenylamino)-4-(phenylthio)butanamide The title compound was prepared as described in Example 10E, replacing morpholine with dimethylamine.

Example 1F (R)-4-(4-(dimethylamino)-1-(phenylthio)butan-2-ylamino)-3-nitrobenzenesulfonamide The title compound was prepared as described in Example 10F, replacing Example 10E with Example 1E.

Example 1G

N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide Example 1D (100 mg), Example 1F (117 mg) and 4-(dimethylamino)pyridine (84 mg) in dichloromethane were treated with 1-ethyl-3-[3-(dimethylamino)propyl]-carbodiimide hydrochloride (52.7 mg) overnight. The reaction mixture was concentrated, and the residue was purified by reverse phase chromatography, eluting with 40%-70% acetonitrile in water containing 01% v/v trifluoroacetic acid, to provide the title compound. $^1$H NMR (400 MHz, DMSO-d$_6$) δ ppm 12.93 (s, 1H), 9.42 (s, 1H), 8.57 (d, 1H), 8.32 (d, 1H), 8.03 (d, 1H), 7.87 (dd, 1H), 7.80 (d, 1H), 7.68-7.73 (m, 2H), 7.45-7.51 (m, 2H), 7.34-7.43 (m, 4H), 7.22-7.26 (m, 2H), 7.10-7.19 (m, 4H), 4.86 (s, 2H), 4.10-4.23 (m, 1H), 3.83-3.92 (m, 2H), 3.32-3.42 (m, 2H), 3.00-3.19 (m, 4H), 2.67-2.80 (m, 6H), 2.14 (q, 2H).

Example 2

N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide Example 2A (R)-tert-butyl 4-(phenylthio)-3-(4-sulfamoyl-2-(trifluoromethylsulfonyl)phenylamino)butanoate The title compound was prepared by following the procedure described in Example 10C, replacing 4-fluoro-3-nitrobenzenesulfonamide with 4-fluoro-3-(trifluoromethylsulfonyl)benzenesulfonamide.

Example 2B (R)-4-(phenylthio)-3-(4-sulfamoyl-2-(trifluoromethylsulfonyl)phenylamino)butanoic acid The title compound was prepared as described in Example 10D, replacing Example 10C with Example 2A.

Example 2C (R)-4-(4-morpholino-4-oxo-1-(phenylthio)butan-2-ylamino)-3-(trifluoromethylsulfonyl)benzenesulfonamide The title compound was prepared as described in Example 10E, replacing Example 10D with Example 2B.

Example 2D (R)-4-(4-morpholino-1-(phenylthio)butan-2-ylamino)-3-(trifluoromethylsulfonyl)benzenesulfonamide The title compound was prepared as described in Example 10F, replacing Example 10E with Example 2C.

Example 2E

N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide The title compound was prepared as described in Example 1G, replacing Example 1F with Example 2D. $^1$H NMR (500 MHz, DMSO-d$_6$) δ ppm 12.91 (s, 1H), 8.13 (d, 1H), 8.02 (d, 1H), 7.96 (dd, 1H), 7.79 (d, 1H), 7.68 (d, 1H), 7.44-7.54 (m, 3H), 7.31-7.42 (m, 4H), 7.27 (t, 2H), 7.18 (t, 1H), 7.00 (d, 1H), 6.90 (d, 1H), 4.84 (s, 2H), 4.06 (d, 1H), 3.82 (t, 2H), 3.57 (s, 4H), 3.24-3.39 (m, 6H), 3.04 (t, 2H), 2.53-2.71 (m, 2H), 1.92-2.05 (m, 1H), 1.79-1.90 (m, 1H).

Example 3

N-(1,3-benzothiazol-2-yl)-2-(6-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide

Example 3A tert-butyl 6-(8-(benzo[d]thiazol-2-ylcarbamoyl)-3,4-dihydroisoquinolin-2(1H)-yl)picolinate A mixture of Example 5D (0.9 g) and 10% Pd—C (0.169 g) in methanol (50 mL) was purged with hydrogen gas and stirred under a hydrogen atmosphere for 24 hours at ambient temperature. The insoluble material was filtered off and the filtrate was concentrated. The residue was purified by HPLC to provide the title compound.

Example 3B 6-(8-(benzo[d]thiazol-2-ylcarbamoyl)-3,4-dihydroisoquinolin-2(1H)-yl)picolinic acid Example 3A (110 mg) was dissolved in dichloromethane (3 mL) and treated with trifluoroacetic acid (3 mL) for 12 hours. The reaction mixture was concentrated to provide the title compound.

Example 3C

N-(1,3-benzothiazol-2-yl)-2-(6-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide The title compound was prepared as described in Example 1G, replacing Example 1D and Example 1F with Example 3B and Example 2D, respectively. $^1$H NMR (400 MHz, DMSO-$d_6$) δ ppm 12.87 (s, 1H), 11.18 (s, 1H), 8.21 (d, 1H), 7.97-8.04 (m, 2H), 7.80 (d, 1H), 7.69 (dd, 1H), 7.63 (d, 1H), 7.42-7.50 (m, 2H), 7.30-7.39 (m, 4H), 7.20-7.28 (m, 3H), 7.13-7.18 (m, 1H), 6.96-7.07 (m, 3H), 4.94 (s, 2H), 3.97-4.15 (m, 3H), 3.23-3.42 (m, 8H), 3.01 (t, 2H), 2.26-2.48 (m, 4H), 1.89-2.04 (m, 1H), 1.72-1.87 (m, 1H).

Example 4

N-(1,3-benzothiazol-2-yl)-2-[6-{[(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide

Example 4A 4-(3-(dimethylamino)propylamino)-3-nitrobenzenesulfonamide

The title compound was prepared by following the procedure described in Example 10C, replacing Example 10B with N',N'-dimethylpropane-1,3-diamine.

Example 4B

N-(1,3-benzothiazol-2-yl)-2-[6-{[(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide The title compound was prepared by following the procedure described in Example 1C, replacing Example 1A and Example 1B with Example 5F and Example 4A, respectively. $^1$H NMR (400 MHz, CDCl$_3$) δ ppm 9.07 (s, 1H), 8.86 (d, 1H), 8.07 (dd, 1H), 7.80 (d, 1H), 7.52-7.57 (m, 2H), 7.23-7.34 (m, 5H), 7.14-7.18 (m, 2H), 7.06-7.09 (m, 3H), 6.89 (d, 1H), 6.78 (d, 1H), 4.99 (s, 2H), 3.82 (t, 2H), 3.31 (q, 2H), 2.96 (t, 2H), 2.89 (t, 2H), 2.54 (t, 2H), 2.39 (t, 2H), 2.20 (s, 6H), 1.73-1.80 (m, 4H).

Example 5

N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide

Example 5A tert-butyl 8-(benzo[d]thiazol-2-ylcarbamoyl)-3,4-dihydroisoquinoline-2(1H)-carboxylate 2-(tert-Butoxycarbonyl)-1,2,3,4-tetrahydroisoquinoline-8-carboxylic acid (6.7 g), benzo[d]thiazol-2-amine (5.5 g) and 4-dimethylaminopyridine (6.6 g) in dichloromethane (78 mL) were treated with 1-ethyl-3-[3-(dimethylamino)propyl]-carbodiimide hydrochloride (9.3 g) at room temperature overnight. The reaction mixture was diluted with dichloromethane (450 mL) and washed with 3% aqueous HCl, water, and brine. The organic layer was dried over Na$_2$SO$_4$, filtered and concentrated to provide the title compound.

Example 5B

N-(benzo[d]thiazol-2-yl)-1,2,3,4-tetrahydroisoquinoline-8-carboxamide dihydrochloride Example 5A (6.7 g) in dichloromethane (70 mL) was treated with 2N HCl (in ether, 80 mL) at room temperature overnight. The reaction mixture was concentrated to provide the title compound.

Example 5C tert-butyl 3-bromo-6-chloropicolinate

To a solution of 2-chloro-5-bromo picolinic acid (4 g) and pyridine (9.2 mL) in t-butanol (33 mL) at 0° C. was added p-toluenesulfonyl chloride (7.7 g). The resulting mixture was stirred at room temperature for 12 hours. Saturated aqueous NaHCO$_3$ solution was added, and the resulting mixture was extracted with ethyl acetate. The combined organic phase was washed with brine, dried over Na$_2$SO$_4$, filtered and concentrated to provide the title compound.

Example 5D tert-butyl 6-(8-(benzo[d]thiazol-2-ylcarbamoyl)-3,4-dihydroisoquinolin-2(1H)-yl)-3-bromopicolinate A mixture of Example 5C (0.736 g), Example 5B (1.62 g), and Cs$_2$CO$_3$ (4.1 g) in N,N-dimethylformamide (15 mL) was heated at 120° C. for 12 hours, cooled, diluted with ethyl acetate, and acidified with 10% citric acid. The organic layer was washed with water and brine, dried over $Na_2SO_4$, filtered and concentrated. The residue was purified by silica gel chromatography, eluting with 0-40% ethyl acetate in hexanes, to provide the title compound.

Example 5E tert-butyl 6-(8-(benzo[d]thiazol-2-ylcarbamoyl)-3,4-dihydroisoquinolin-2(1H)-yl)-3-(3-phenylpropyl)picolinate To a mixture of Example 5D (200 mg), [1,1'-bis(diphenylphosphino)ferrocene]dichloropalladium(II) dichloromethane (28.9 mg) and 2,2'-bis(diphenylphosphino)-1,1'-binaphthyl (22 mg) in tetrahydrofuran (3 mL) was added (3-phenylpropyl)zinc(II) bromide (1.42 mL). The resulting suspension was heated in a Biotage microwave synthesizer at 100° C. for 30 minutes. The reaction mixture was filtered through a sintered glass funnel. The filtrate was concentrated, and the residue was purified by preparative TLC, eluting with 40% acetone in petroleum ether, to provide the title compound.

Example 5F 6-(8-(benzo[d]thiazol-2-ylcarbamoyl)-3,4-dihydroisoquinolin-2(1H)-yl)-3-(3-phenylpropyl)picolinic acid Example 5E (200 mg) in dichloromethane (5 mL) was treated with trifluoroacetic acid (5 mL) overnight. The solution was concentrated to provide the title compound.

Example 5G 4-(3-(dimethylamino)propylamino)-3-(trifluoromethylsulfonyl)benzenesulfonamide The title compound was prepared by following the procedure described in Example 10C, replacing Example 10B and 4-fluoro-3-nitrobenzenesulfonamide with N',N'-dimethylpropane-1,3-diamine and 4-fluoro-3-(trifluoromethylsulfonyl)benzenesulfonamide, respectively.

Example 5H

N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide The title compound was prepared by following the procedure described in Example 1C, replacing Example 1A and Example 1B with Example 5F and Example 5G, respectively.
$^1$H NMR (400 MHz, $CDCl_3$) δ ppm 8.44 (d, 1H), 8.16 (dd, 1H), 7.76-7.78 (m, 2H), 7.49 (d, 1H), 7.21-7.30 (m, 5H), 7.14-7.19 (m, 3H), 7.05-7.08 (m, 3H), 6.87 (d, 1H), 6.67 (d, 1H), 4.96 (s, 2H), 3.77 (t, 2H), 3.21-3.25 (m, 2H), 2.93 (t, 2H), 2.84-2.88 (m, 2H), 2.54 (t, 2H), 2.41 (t, 2H), 2.21 (s, 6H), 1.70-1.77 (m, 4H).

Example 6

N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide

Example 6A tert-butyl 6-(8-(benzo[d]thiazol-2-ylcarbamoyl)-3,4-dihydroisoquinolin-2(1H)-yl)-3-phenethylpicolinate The title compound was prepared by following the procedure described in Example 5E, replacing (3-phenylpropyl)zinc(II) bromide with phenethylzinc(II) bromide.

Example 6B 6-(8-(benzo[d]thiazol-2-ylcarbamoyl)-3,4-dihydroisoquinolin-2(1H)-yl)-3-phenethylpicolinic acid The title compound was prepared by following the procedure described in Example 5F, replacing Example 5E with Example 6A.

Example 6C

N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide The title compound was prepared by following the procedure described in Example 1C, replacing Example 1A and Example 1B with Example 6B and Example 4A, respectively.
$^1$H NMR (400 MHz, $CDCl_3$) δ ppm 8.98 (s, 1H), 8.90 (d, 1H), 8.09 (dd, 1H), 7.78-7.80 (m, 1H), 7.52 (d, 1H), 7.38-7.40 (m, 1H), 7.23-7.28 (m, 4H), 7.14-7.18 (m, 3H), 7.07-7.08 (m, 3H), 6.77-6.84 (m, 2H), 4.79 (t, 2H), 3.79 (t, 2H), 3.70 (t, 1H), 3.57 (t, 1H), 3.33 (q, 2H), 3.09 (t, 2H), 2.95 (t, 2H), 2.68 (t, 2H), 2.46 (t, 2H), 2.26 (s, 6H), 1.80-1.84 (m, 2H).

Example 7

N-(1,3-benzothiazol-2-yl)-2-(4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide The title compound was prepared by following the procedure described in Example 1C, replacing Example 1B with Example 5G. $^1$H NMR (400 MHz, $CDCl_3$) δ ppm 8.37 (s, 1H), 8.16 (d, 1H), 7.81 (d, 1H), 7.65 (d, 1H), 7.56 (d, 1H), 7.26-7.39 (m, 7H), 6.75 (dd, 1H), 4.91 (s, 2H), 3.81 (t, 2H), 3.30 (s, 2H), 3.04 (t, 2H), 2.47 (s, 2H), 2.26 (s, 6H), 1.84-1.79 (m, 2H).

Example 8

N-(1,3-benzothiazol-2-yl)-2-(5-b enzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide

Example 8A

To a mixture of Example 1B (1.1 g) and triethylamine (1.439 g) in DMF (18 mL) was added di-1H-imidazol-1-yl)

methanethione (0.76 g). The resulting solution was stirred at room temperature for 30 minutes, and 7 N ammonia in methanol (40 equiv) was added slowly. The reaction mixture was stirred for 12 hours and concentrated to give the title product, which was used in the next step without further purification.

Example 8B ethyl 2-(8-(benzo[d]thiazol-2-ylcarbamoyl)-3,4-dihydroisoquinolin-2(1H)-yl)-5-benzylthiazole-4-carboxylate NaH (74.9 mg) was added portionwise to ethanol (0.109 mL). The mixture was cooled in an ice-bath and slowly added to a mixture of ethyl 2,2-dichloroacetate (294 mg, 1.87) and 2-phenylacetaldehyde (225 mg) in N,N-dimethylformamide (20 mL) at 0° C. The resulting solution was stirred at 0° C. for 1.5 hours and diluted with ether. The layers were separated, and the organic was washed with brine, dried over $Na_2SO_4$, filtered and concentrated. The residue was added to a solution of Example 8A (690 mg) in N,N-dimethylformamide (20 mL). The resulting mixture was stirred at 50° C. overnight and diluted with ethyl acetate and washed with brine. The organic layer was dried over $MgSO_4$, filtered, and concentrated. The residue was purified by preparative TLC, eluting with 30% ethyl acetate in heptane, to give the title product.

Example 8C 2-(8-(benzo[d]thiazol-2-ylcarbamoyl)-3,4-dihydroisoquinolin-2(1H)-yl)-5-benzylthiazole-4-carboxylic acid Example 8B (669 mg) in tetrahydrofuran (3 mL) was treated with LiOH (289 mg) in water (1 mL) for 12 hours. The solution was acidified with concentrated HCl and concentrated. The residue was dissolved in dichloromethane and washed with brine. The organic layer was dried over $MgSO_4$, filtered and concentrated. The residue was purified by preparative TLC, eluting with 60% ethyl acetate in heptane, to provide the title compound.

Example 8D

N-(1,3-benzothiazol-2-yl)-2-(5-b enzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide The title compound was prepared by following the procedure described in Example 1C, replacing Example 1A and Example 1B with Example 8C and Example 5G, respectively.
$^1$H NMR (400 MHz, DMSO-$d_6$) δ ppm 8.15 (d, 1H), 8.05 (dd, 1H), 8.02 (d, 1H), 7.79 (d, 1H), 7.65 (d, 1H), 7.48 (t, 1H), 7.41 (d, 1H), 7.36 (t, 2H), 7.19-7.21 (m, 5H), 7.13-7.15 (m, 1H), 7.05 (d, 1H), 4.73 (s, 2H), 4.40 (s, 2H), 3.68 (t, 2H), 3.37-3.42 (m, 2H), 2.97 (t, 2H), 2.92 (t, 2H), 2.64 (s, 6H), 1.81-1.88 (m, 2H).

Example 9

N-(1,3-benzothiazol-2-yl)-2-(5-b enzyl-4-{[(4-{[3-(dimethylamino)propyl]amino}-3-nitrophenyl)sulfonyl]carbamoyl}-1,3-thiazol-2-yl)-1,2,3,4-tetrahydroisoquinoline-8-carboxamide The title compound was prepared by following the procedure described in Example 1C, replacing Example 1A and Example 1B with Example 8C and Example 4A, respectively.

$^1$H NMR (400 MHz, DMSO-$d_6$) δ ppm 8.52 (d, 1H), 8.03 (d, 1H), 7.91 (dd, 1H), 7.79 (d, 1H), 7.64 (d, 1H), 7.47 (t, 1H), 7.34-7.43 (m, 4H), 7.17-7.22 (m, 4H), 7.11-7.14 (m, 1H), 7.07 (d, 1H), 4.72 (s, 2H), 4.43 (s, 2H), 3.67 (t, 2H), 3.45 (q, 2H), 2.96 (t, 2H), 2.87-2.90 (m, 2H), 2.58 (s, 6H), 1.85-1.92 (m, 2H).

Example 10

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide Example 10A (R)-tert-butyl 3-(4(9H-fluoren-9-yl)methoxy)carbonyloxy)carbonylamino)-4-(phenylthio)butanoate To a solution of (R)-tert-butyl 3-(((9H-fluoren-9-yl)methoxy)carbonylamino)-4-hydroxybutanoate (2.6 g) in toluene (15 mL) was added 1,2-diphenyldisulfane (2.86 g) and tributylphosphine (1.588 g). The resulting solution was heated in a Biotage microwave synthesizer to 110° C. for 30 minutes and was concentrated. The residue was purified by preparative HPLC to provide the title compound.

Example 10B (R)-tert-butyl 3-amino-4-(phenylthio)butanoate

Example 10A (3.6 g) in dichloromethane (16 mL) was treated with piperidine (4 mL) at 25° C. for 6 hours. The solvent was removed to provide the title compound.

Example 10C (R)-tert-butyl 3-(2-nitro-4-sulfamoylphenylamino)-4-(phenylthio)butanoate 4-Fluoro-3-nitrobenzenesulfonamide (1.23 g) and Example 10B (1.49 g) in N,N-dimethylformamide (20 mL) were treated with N-ethyl-N-isopropylpropan-2-amine (2.88 g) at 25° C. overnight. The mixture was washed with water. The organic layer was dried over $Na_2SO_4$, filtered, and concentrated. The residue was purified by flash chromatography, eluting with 10% ethyl acetate in hexane, to give the title product.

Example 10D (R)-3-(2-nitro-4-sulfamoylphenylamino)-4-(phenylthio)butanoic acid

Example 10C (2.3 g) in dichloromethane (20 mL) was treated with 2,2,2-trifluoroacetic acid (4 mL) for 6 hours. The solvent was removed to provide the title compound.

Example 10E (R)-4-(4-morpholino-4-oxo-1-(phenylthio)butan-2-ylamino)-3-nitrobenzenesulfonamide To a mixture of Example 10D (0.75 g) and morpholine (0.318 g) in N,N-dimethylformamide (5 mL) were added N,N-dimethylpyridin-4-amine (0.445 g) and 1-ethyl-3-[3-(dimethylamino)propyl]-carbodiimide hydrochloride (0.699 g). The mixture was stirred overnight, diluted with ethyl acetate and washed with 5% aqueous HCl and water. The organic layer was dried over Na₂SO₄ and concentrated to give the title compound.

Example 10F (R)-4-(4-morpholino-1-(phenylthio)butan-2-ylamino)-3-nitrobenzenesulfonamide Example 10E (0.68 g) in tetrahydrofuan (5 mL) was treated with 1M BH₃-THF solution (5 mL) at 25° C. overnight. The solution was concentrated, and the residue was purified by flash chromatography, eluting with 10% methanol in dichloromethane, to provide the title compound.

Example 10G

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide The title compound was prepared by following the procedure described in Example 1G, replacing Example 1F with Example 10F, respectively. ¹H NMR (400 MHz, CDCl₃) δ ppm 8.77 (d, 1H), 8.55 (d, 1H), 7.90 (dd, 1H), 7.46-7.76 (m, 1H), 7.55 (d, 1H), 7.39 (s, 1H), 7.22-7.29 (m, 7H), 7.14-7.18 (m, 3H), 6.64 (d, 1H), 4.88 (s, 2H), 3.93-3.94 (m, 1H), 3.74 (t, 2H), 3.56-3.62 (m, 4H), 3.04-3.07 (m, 2H), 2.98 (t, 2H), 2.29-2.37 (m, 4H), 2.03-2.06 (m, 2H), 1.70-1.76 (m, 2H).

Example 11

N-(1,3-benzothiazol-2-yl)-2-[4-{[(4-{[3-(dimethylamino)propyl]amino}-3-[(trifluoromethyl)sulfonyl]phenyl)sulfonyl]carbamoyl}-5-(2-phenylethyl)-1,3-thiazol-2-yl]-1,2,3,4-tetrahydroisoquinoline-8-carboxamide Example 11A ethyl 2-(8-(benzo[d]thiazol-2-ylcarbamoyl)-3,4-dihydroisoquinolin-2(1H)-yl)-5-phenethylthiazole-4-carboxylate To a solution of 3-phenylpropanal (2 g) and ethyl 2,2-dichloroacetate (2.34 g) in diethyl ether (11 mL) at 0° C. was added a solution of NaH (0.656 g) in ethanol (0.8 mL) dropwise. The reaction mixture was stirred at 0° C. for 1.5 hours and diluted with diethyl ether. The resulting mixture was washed with brine, and the organic layer was dried over Na₂SO₄, filtered and concentrated. The residue was dried in vacuo and dissolved in ethanol (1.6 mL). The resulting solution was then treated with Example 8A (0.5 g) in N,N-dimethylformamide. The reaction mixture was heated at 50° C. for 12 hours and concentrated. The residue was dissolved in dichloromethane and purified by preparative TLC, eluting with 33% ethyl acetate in petroleum ether, to provide the title compound.

Example 11B 2-(8-(benzo[d]thiazol-2-ylcarbamoyl)-3,4-dihydroisoquinolin-2(1H)-yl)-5-phenethylthiazole-4-carboxylic acid The title compound was prepared by following the procedure described in Example 8C, replacing Example 8B with Example 11A.

Example 11C

N-(1,3-benzothiazol-2-yl)-2-[4-{[(4-{[3-(dimethylamino)propyl]amino}-3-[(trifluoromethyl)sulfonyl]phenyl)sulfonyl]carbamoyl}-5-(2-phenylethyl)-1,3-thiazol-2-yl]-1,2,3,4-tetrahydroisoquinoline-8-carboxamide The title compound was prepared by following the procedure described in Example 1C, replacing Example 1A and Example 1B with Example 11B and Example 5G, respectively. ¹H NMR (400 MHz, DMSO-d₆) δ ppm 8.15 (d, 1H), 8.03-8.06 (m, 2H), 7.80 (d, 1H), 7.65 (d, 1H), 7.48 (t, 1H), 7.43 (d, 1H), 7.34-7.39 (m, 2H), 7.19-7.24 (m, 5H), 7.11-7.15 (m, 1H), 7.04 (d, 1H), 4.74 (s, 2H), 3.72 (t, 2H), 3.21-3.26 (m, 4H), 3.00 (t, 2H), 2.85-2.89 (m, 2H), 2.77 (t, 2H), 2.60 (s, 6H), 1.71-1.86 (m, 2H).

Example 12

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide Example 12A (R)—N,N-dimethyl-4-(phenylthio)-3-(4-sulfamoyl-2-(trifluoromethylsulfonyl)phenylamino)butanamide The title compound was prepared by following the procedure described in Example 10E, replacing Example 10D and morpholine with Example 2B and dimethylamine, respectively.

Example 12B (R)-4-(4-(dimethylamino)-1-(phenylthio)butan-2-ylamino)-3-(trifluoromethylsulfonyl)benzenesulfonamide The title compound was prepared by following the procedure described in Example 10F, replacing Example 10E with Example 12A.

Example 12C

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide The title compound was prepared by following the procedure described in Example 1G, replacing Example 1F with Example 12B. ¹H NMR (400 MHz, CDCl₃) δ ppm 8.36 (s, 1H), 8.04 (d, 1H), 7.85 (d, 1H), 7.78 (d, 2H), 7.51 (t, 1H), 7.40-7.43 (m, 4H), 7.31 (d, 2H), 7.22 (t, 2H), 6.88 (d, 1H), 6.54 (d, 1H), 4.96 (s, 2H), 3.77 (t, 2H), 2.97-3.06 (m, 5H), 2.84-2.96 (m, 2H), 2.70 (s, 6H), 1.88-2.03 (m, 2H).

Example 13

N-(1,3-benzothiazol-2-yl)-2-[4-{[(4-{[3-(dimethylamino)propyl]amino}-3-nitrophenyl)sulfonyl]carbamoyl}-5-(2-phenylethyl)-1,3-thiazol-2-yl]-1,2,3,4-tetrahydroisoquinoline-8-carboxamide The title compound was prepared by following the procedure described in Example 1C, replacing Example 1A and Example 1B with Example 11B and Example 4A, respectively. $^1$H NMR (400 MHz, DMSO-$d_6$) δ ppm 8.55 (d, 2H), 8.04 (d, 1H), 7.92 (dd, 1H), 7.80 (d, 1H), 7.65 (d, 1H), 7.48 (t, 1H), 7.34-7.44 (m, 3H), 7.19-7.24 (m, 4H), 7.11-7.15 (m, 1H), 7.08 (d, 1H), 4.74 (s, 2H), 3.72 (t, 2H), 3.45 (q, 2H), 3.23-3.27 (m, 2H), 3.00 (t, 2H), 2.90-2.94 (m, 2H), 2.75-2.79 (m, 2H), 2.61 (s, 6H), 1.85-1.92 (m, 2H).

Example 14

N-(1,3-benzothiazol-2-yl)-2-(4-{[(4-{[(2R)-4-hydroxy-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide Example 14A (R)-tert-butyl 3-(((9H-fluoren-9-yl)methoxy)carbonylamino)-4-hydroxybutanoate (R)-2-(((9H-fluoren-9-yl)methoxy)carbonylamino)-4-tert-butoxy-4-oxobutanoic acid (8.2 g) in tetrahydrofuran (2 mL) was treated with BH$_3$-THF (39.9 mL) overnight. The reaction mixture was quenched with water and extracted with dichloromethane. The combined organic layer was washed with brine, dried over MgSO$_4$, filtered and concentrated. The residue was purified by flash chromatography, eluting with 30% ethyl acetate in petroleum ether, to provide the title compound.

Example 14B (R)-tert-butyl 3-(((9H-fluoren-9-yl)methoxy)carbonylamino)-4-(phenylthio)butanoate A mixture of Example 14A (2.2 g), tributylphosphine (1.23 g) and 1,2-diphenyldisulfane (1.81 g) in toluene (12 mL) was heated to 110° C. for 2 hours in a CME microwave synthesizer, cooled and diluted with ethyl acetate. The resulting solution was washed with brine, and the organic layer was dried over MgSO$_4$, filtered and concentrated. The residue was purified by flash chromatography, eluting with 20% ethyl acetate in petroleum ether, to provide the title compound.

Example 14C (R)-tert-butyl 3-amino-4-(phenylthio)butanoate

Example 14B (2.2 g) in dichloromethane (50 mL) was treated with piperidine (4.45 mL) overnight. The reaction mixture was diluted with dichloromethane and washed with water. The organic layer was dried over MgSO$_4$, filtered and concentrated. The residue was purified by silica gel chromatography, eluting with 30% ethyl acetate in petroleum ether, to provide the title compound.

Example 14D (R)-tert-butyl 4-(phenylthio)-3-(4-sulfamoyl-2-(trifluoromethylsulfonyl)phenylamino)butanoate A mixture of Example 14C (330 mg), 4-fluoro-3-(trifluoromethylsulfonyl)benzenesulfonamide (455 mg) and triethylamine (1 mL) in N,N-dimethylformamide (8 mL) was heated to 65° C. overnight and concentrated. The residue was dissolved in dichloromethane and washed with water. The organic layer was dried over MgSO$_4$, filtered and concentrated. The residue was purified by silica gel chromatography, eluting with 50% ethyl acetate in petroleum ether, to provide the title compound.

Example 14E (R)-4-(phenylthio)-3-(4-sulfamoyl-2-(trifluoromethylsulfonyl)phenylamino)butanoic acid Example 14D (250 mg) in dichloromethane (2 mL) was treated with trifluoroacetic acid (0.347 mL) for 2 hours. The reaction mixture was concentrated to provide the title compound.

Example 14F (R)-4-(4-hydroxy-1-(phenylthio)butan-2-ylamino)-3-(trifluoromethylsulfonyl)benzenesulfonamide Example 14E (60 mg) in tetrahydrofuran (1 mL) was treated with 1M BH$_3$-THF (1.204 mL) overnight. The reaction mixture was quenched with water, and the resulting aqueous mixture was extracted with dichloromethane. The combined organic layer was washed with brine, dried over MgSO$_4$, filtered and concentrated. The residue was purified by flash chromatography, eluting with 14% methanol in dichloromethane, to provide the title compound.

Example 14G (R)-2-(8-(benzo[d]thiazol-2-ylcarbamoyl)-3,4-dihydroisoquinolin-2(1H)-yl)-N-(4-(4-hydroxy-1-(phenylthio)butan-2-ylamino)-3-(trifluoromethylsulfonyl)phenylsulfonyl)thiazole-4-carboxamide A mixture of Example 1A (20 mg), Example 14F (22.2 mg), HATU (O-(7-azabenzotriazol-1-yl)-N,N,N',N'-tetramethyluronium hexafluorophosphate, 17.4 mg), triethylamine (0.007 mL) and 4-(dimethylamino)pyridine (5.6 mg) in dichloromethane were stirred at 50° C. overnight. The reaction mixture was cooled to room temperature and concentrated. The residue was purified by HPLC, eluting with a gradient of 40 to 80% acetonitrile in water containing 0.1% v/v trifluoroacetic acid, to provide the title compound.
$^1$H NMR (400 MHz, DMSO-$d_6$): 12.90 (s, 1H), 8.07 (s, 1H), 8.03 (d, 1H), 7.91 (d, 1H), 7.79 (d, 1H), 7.66 (d, 1H), 7.47 (dd, 3H), 7.38 (t, 2H), 7.34 (d, 3H), 7.27 (t, 2H), 7.17 (t, 1H), 6.95-7.07 (m, 2H), 4.83 (s, 2H), 4.70 (t, 1H), 4.07 (s, 1H), 3.79 (s, 2H), 3.40-3.50 (m, 2H), 3.04 (t, 2H), 1.91-1.83 (m, 1H), 1.80-1.71 (m, 1H), 1.24 (s, 1H).

Example 15

N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide

Example 15A methyl 2-(8-(benzo[d]thiazol-2-ylcarbamoyl)-3,4-dihydroisoquinolin-2(1H)-yl)-5-iodothiazole-4-carboxylate To a solution of Example 1B (2 g) and methyl 2-chloro-5-iodothiazole-4-carboxylate (1.66 g), in N,N-dimethylacetamide (10 mL) was added $Cs_2CO_3$ (8.5 g). The mixture was stirred at 60° C. overnight, then cooled to room temperature and acidified with 5% aqueous HCl. The resulting mixture was extracted with dichloromethane and washed with water, brine and dried over $Na_2SO_4$, and concentrated. The residue was purified by flash chromatography, eluting with 5% methanol in dichloromethane, to give the title compound.

Example 15B methyl 2-(8-(benzo[d]thiazol-2-yl((2-(trimethylsilyl)ethoxy)methyl)carbamoyl)-3,4-dihydroisoquinolin-2(1H)-yl)-5-iodothiazole-4-carboxylate To a solution of Example 15A (2.0 g) and (2-(chloromethoxy)ethyl)trimethylsilane (1.2 g) in dichloromethane (20 mL) was added triethylamine (1.55 g). The mixture was stirred at room temperature overnight and concentrated. The residue was purified by flash chromatography, eluting with 20% ethyl acetate in hexane, to give the title compound.

Example 15C methyl 2-(8-(benzo[d]thiazol-2-yl((2-(trimethylsilyl)ethoxy)methyl)carbamoyl)-3,4-dihydroisoquinolin-2(1H)-yl)-5-(3-phenylprop-1-ynyl)thiazole-4-carboxylate To a solution of Example 15B (1.69 g) in tetrahydrofuran (30 mL) was added bis(triphenylphosphine)palladium (II) dichloride (88 mg), CuI (4.8 mg), prop-2-ynylbenzene (584 mg) and triethylamine (1.5 mL). The mixture was stirred at room temperature for 3 hours, diluted with diethyl ether and washed with water and brine. The organic layer was dried over $Na_2SO_4$, filtered, and concentrated. The residue was purified by flash chromatography, eluting with 10% ethyl acetate in hexanes, to give the title compound.

Example 15D methyl 2-(8-(benzo[d]thiazol-2-yl((2-(trimethylsilyl)ethoxy)methyl)carbamoyl)-3,4-dihydroisoquinolin-2(1H)-yl)-5-(3-phenylpropyl)thiazole-4-carboxylate To a solution of Example 15C (1.2 g) in ethyl acetate (120 mL) was added Pd/C (500 mg, 5%). The mixture was stirred under an atmosphere of hydrogen (balloon) overnight. The insoluble material was filtered off and washed with ethyl acetate. The filtrate was concentrated to provide the title compound.

Example 15E 2-(8-(benzo[d]thiazol-2-ylcarbamoyl)-3,4-dihydroisoquinolin-2(1H)-yl)-5-(3-phenylpropyl)thiazole-4-carboxylic acid Example 15D (1.2 g) in dichloromethane (30 mL) was treated with trifluoroacetic acid (30 mL) overnight. The mixture was concentrated, and the residue was taken into ethyl acetate (400 mL) and washed with aqueous $NaHCO_3$, water, and brine. The organic layer was dried over $Na_2SO_4$, filtered and concentrated. The residue was dissolved in a solvent mixture of tetrahydrofuran (20 mL) and methanol (10 mL) and treated with solution of lithium hydroxide monohydrate (1.2 g) in water (10 mL) overnight. The mixture was concentrated. The residue was suspended in ethyl acetate (400 mL), washed with 2N aqueous HCl (60 mL) and brine, dried over $Na_2SO_4$, filtered and concentrated to provide the title compound.

Example 15F

N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide The title compound was prepared by following the procedure described in Example 1G, replacing Example 1D and Example 1F with Example 15E and Example 4A, respectively.

$^1$H NMR (300 MHz, DMSO-$d_6$) δ ppm 12.88 (s, 1H), 9.23 (s, 1H), 8.69 (m, 2H), 8.00 (m, 2H), 7.74 (m, 2H), 7.43 (m, 5H), 7.16 (m, 7H), 4.80 (s, 2H), 3.91 (t, 2H), 3.05 (m, 8H), 2.75 (m, 6H), 1.85 (m, 4H).

It has been contemplated that the following compounds of Formula (I) could be prepared using methods similar to those described in the Schemes and Experimental sections herein.

Example 16

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide

Example 17

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide

Example 18

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide

Example 19

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide

Example 20

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide

Example 21

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide

Example 22

N-(imidazo[1,2-a]pyridin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide

Example 23

N-(imidazo[1,2-a]pyridin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide

Example 24

N-(imidazo[1,2-a]pyrazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide

Example 25

N-(imidazo[1,2-a]pyrazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide

Example 26

N-(imidazo[1,2-b]pyridazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide

Example 27

N-(imidazo[1,2-b]pyridazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide

Example 28

N-(6-fluoro-1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide

Example 29

N-(6-fluoro-1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide

Example 30

N-(1,3-benzothiazol-2-yl)-2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide

Example 31

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide

Example 32

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-b]pyridin-2-yl)-1,2,3,4-tetrahydroisoquinoline-8-carboxamide

Example 33

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide

Example 34

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-c]pyridin-2-yl)-1,2,3,4-tetrahydroisoquinoline-8-carboxamide

Example 35

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide

Example 36

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[4,5-c]pyridin-2-yl)-1,2,3,4-tetrahydroisoquinoline-8-carboxamide

Example 37

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide

Example 38

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyridin-2-yl)-1,2,3,4-tetrahydroisoquinoline-8-carboxamide

Example 30

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyridin-2-yl)-1,2,3,4-tetrahydroisoquinoline-8-carboxamide

Example 40

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyrazin-2-yl)-1,2,3,4-tetrahydroisoquinoline-8-carboxamide

Example 41

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyrazin-2-yl)-1,2,3,4-tetrahydroisoquinoline-8-carboxamide

Example 42

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-b]pyridazin-2-yl)-1,2,3,4-tetrahydroisoquinoline-8-carboxamide

Example 43

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-b]pyridazin-2-yl)-1,2,3,4-tetrahydroisoquinoline-8-carboxamide

Example 44

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(6-fluoro-1,3-benzothiazol-2-yl)-1,2,3,4-tetrahydroisoquinoline-8-carboxamide

Example 45

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide

Example 46

N-(1,3-benzothiazol-2-yl)-2-(6-{[(3-{[chloro(difluoro)methyl]sulfonyl}-4-{[(2R)-4-(morpholin-4-yl)-1-(phenylsulfanyl)butan-2-yl]amino}-phenyl)sulfonyl]carbamoyl}pyridin-2-yl)-1,2,3,4-tetrahydroisoquinoline-8-carboxamide

Example 47

N-(1,3-benzothiazol-2-yl)-2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide

Example 48

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide

Example 49

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide

Example 50

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide

Example 51

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide

Example 52

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-

N-([1,3]thiazolo[4,5-c]pyridin-2-yl)-1,2,3,4-tetrahydroisoquinoline-8-carboxamide Example 53

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide Example 54

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide Example 55

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide Example 56

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide Example 57

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide Example 58

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide Example 59

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide Example 60

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(6-fluoro-1,3-benzothiazol-2-yl)-1,2,3,4-tetrahydroisoquinoline-8-carboxamide Example 61

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide Example 62

N-(1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide Example 63

N-(1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide Example 64

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-b]pyridin-2-yl)-1,2,3,4-tetrahydroisoquinoline-8-carboxamide Example 65

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide Example 66

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[5,4-c]pyridin-2-yl)-1,2,3,4-tetrahydroisoquinoline-8-carboxamide Example 67

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide Example 68

2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-N-([1,3]thiazolo[4,5-c]pyridin-2-yl)-1,2,3,4-tetrahydroisoquinoline-8-carboxamide

Example 69

2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide

Example 70

N-(imidazo[1,2-a]pyridin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide

Example 71

N-(imidazo[1,2-a]pyridin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide

Example 72

N-(imidazo[1,2-a]pyrazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide

Example 73

N-(imidazo[1,2-a]pyrazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide

Example 74

N-(imidazo[1,2-b]pyridazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide

Example 75

N-(imidazo[1,2-b]pyridazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide

Example 76

N-(6-fluoro-1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide

Example 77

N-(6-fluoro-1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide

Example 78

N-(1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide

Example 79

N-(1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide

Example 80

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide

Example 81

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide

Example 82

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide

Example 83

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide

Example 84

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide

Example 85

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide

Example 86

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide

Example 87

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide

Example 88

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide

Example 89

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide

Example 90

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide

Example 91

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide

Example 92

N-(6-fluoro-1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide

Example 93

N-(6-fluoro-1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide

Example 94

N-(1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide

Example 95

N-(1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide

Example 96

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-b]pyridin-2-yl)-1,2,3,4-tetrahydroisoquinoline-8-carboxamide

Example 97

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide

Example 98

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-c]pyridin-2-yl)-1,2,3,4-tetrahydroisoquinoline-8-carboxamide

Example 99

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide

Example 100

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[4,5-c]pyridin-2-yl)-1,2,3,4-tetrahydroisoquinoline-8-carboxamide

Example 101

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide

Example 102

N-(imidazo[1,2-a]pyridin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide

Example 103

N-(imidazo[1,2-a]pyridin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide

Example 104

N-(imidazo[1,2-a]pyrazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide

Example 105

N-(imidazo[1,2-a]pyrazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide

Example 106

N-(imidazo[1,2-b]pyridazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide

Example 107

N-(imidazo[1,2-b]pyridazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide

Example 108

N-(6-fluoro-1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide

Example 109

N-(6-fluoro-1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide

Example 110

N-(1,3-benzothiazol-2-yl)-2-(6-{[(4-{[(2R)-4-(dimethylamino)-1-phenoxybutan-2-yl]amino}-3-nitrophenyl)sulfonyl]carbamoyl}pyridin-2-yl)-1,2,3,4-tetrahydroisoquinoline-8-carboxamide

Example 111

N-(1,3-benzothiazol-2-yl)-2-(4-{[(4-{[(2R)-4-(dimethylamino)-1-phenoxybutan-2-yl]amino}-3-nitrophenyl)sulfonyl]carbamoyl}-1,3-thiazol-2-yl)-1,2,3,4-tetrahydroisoquinoline-8-carboxamide

Example 112

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide

Example 113

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide

Example 114

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide

Example 115

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide

Example 116

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide

Example 117

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide

Example 118

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyridin-2-yl)-1,2,3,4-tetrahydroisoquinoline-8-carboxamide

Example 119

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyridin-2-yl)-1,2,3,4-tetrahydroisoquinoline-8-carboxamide

Example 120

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyrazin-2-yl)-1,2,3,4-tetrahydroisoquinoline-8-carboxamide

Example 121

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyrazin-2-yl)-1,2,3,4-tetrahydroisoquinoline-8-carboxamide

Example 122

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-b]pyridazin-2-yl)-1,2,3,4-tetrahydroisoquinoline-8-carboxamide

Example 123

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-b]pyridazin-2-yl)-1,2,3,4-tetrahydroisoquinoline-8-carboxamide

Example 124

2-(6-{[(4-{[(2R)-4-(dimethylamino)-1-phenoxybutan-2-yl]amino}-3-nitrophenyl)sulfonyl]carbamoyl}pyridin-2-yl)-N-(6-fluoro-1,3-benzothiazol-2-yl)-1,2,3,4-tetrahydroisoquinoline-8-carboxamide

Example 125

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(6-fluoro-1,3-benzothiazol-2-yl)-1,2,3,4-tetrahydroisoquinoline-8-carboxamide

Example 126

N-(1,3-benzothiazol-2-yl)-2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-1,2,3,4-tetrahydroisoquinoline-8-carboxamide

Example 127

N-(1,3-benzothiazol-2-yl)-2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-1,2,3,4-tetrahydroisoquinoline-8-carboxamide

Example 128

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-b]pyridin-2-yl)-1,2,3,4-tetrahydroisoquinoline-8-carboxamide

Example 129

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide

Example 130

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-c]pyridin-2-yl)-1,2,3,4-tetrahydroisoquinoline-8-carboxamide

Example 131

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide

Example 132

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[4,5-c]pyridin-2-yl)-1,2,3,4-tetrahydroisoquinoline-8-carboxamide

Example 133

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide

Example 134

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyridin-2-yl)-1,2,3,4-tetrahydroisoquinoline-8-carboxamide

Example 135

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyridin-2-yl)-1,2,3,4-tetrahydroisoquinoline-8-carboxamide

Example 136

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyrazin-2-yl)-1,2,3,4-tetrahydroisoquinoline-8-carboxamide

Example 137

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyrazin-2-yl)-1,2,3,4-tetrahydroisoquinoline-8-carboxamide

Example 138

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-b]pyridazin-2-yl)-1,2,3,4-tetrahydroisoquinoline-8-carboxamide

Example 139

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-b]pyridazin-2-yl)-1,2,3,4-tetrahydroisoquinoline-8-carboxamide

Example 140

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(6-fluoro-1,3-benzothiazol-2-yl)-1,2,3,4-tetrahydroisoquinoline-8-carboxamide

Example 141

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(6-fluoro-1,3-benzothiazol-2-yl)-1,2,3,4-tetrahydroisoquinoline-8-carboxamide

Example 142

N-(1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide

Example 143

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide

---

We claim:
1. A compound having Formula (I)

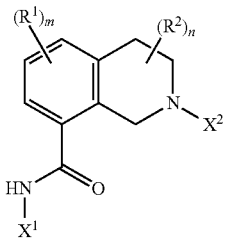

Formula (I)

or a therapeutically acceptable salt thereof, wherein
X$^1$ is heteroaryl; optionally substituted with one, two, three, or four R$^4$;
X$^2$ is

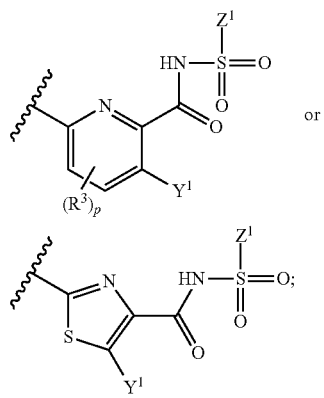

or

Y$^1$ is hydrogen, (CH$_2$)$_r$R$^5$, (CH$_2$)$_r$OR$^5$, (CH$_2$)$_r$NHR$^5$, (CH$_2$)$_r$N(R$^5$)$_2$, or (CH$_2$)$_r$SR$^5$;
R$^1$, at each occurrence, is independently selected from the group consisting of halo, C$_{1-6}$ alkyl, C$_{2-6}$ alkenyl, C$_{2-6}$ alkynyl, and C$_{1-6}$ haloalkyl;
R$^2$, at each occurrence, is independently selected from the group consisting of deuterium, halo, C$_{1-6}$ alkyl, C$_{2-6}$ alkenyl, C$_{2-6}$ alkynyl, and C$_{1-6}$ haloalkyl;
two R$^2$ that are attached to the same carbon atom, together with said carbon atom, optionally form a ring selected from the group consisting of heterocycloalkyl, heterocycloalkenyl, cycloalkyl, and cycloalkenyl;
R$^3$, at each occurrence, is independently selected from the group consisting of halo, C$_{1-6}$ alkyl, C$_{2-6}$ alkenyl, C$_{2-6}$ alkynyl, and C$_{1-6}$ haloalkyl;
R$^4$, at each occurrence, is independently selected from the group consisting of NR$^6$R$^7$, OR$^6$, CN, NO$_2$, halogen, C(O)OR$^6$, C(O)NR$^6$R$^7$, NR$^6$C(O)R$^7$, NR$^6$S(O)$_2$R$^8$, NR$^6$S(O)R$^8$, S(O)$_2$R$^8$, S(O)R$^8$ and R$^8$;
R$^5$ is aryl or heterocyclyl; optionally substituted with one, two, three, or four substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$ R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, CO(O)H, C(O)H, OH, CN, N$_3$, NO$_2$, F, Cl, Br and I;

R$^6$ and R$^7$, at each occurrence, are each independently selected from the group consisting of hydrogen, C$_{1-4}$ alkyl, C$_{2-4}$ alkenyl, C$_{2-4}$ alkynyl, C$_{1-4}$ haloalkyl and (CH$_2$)$_{1-4}$ phenyl;
R$^8$, at each occurrence, is independently selected from the group consisting of C$_{1-4}$ alkyl, C$_{2-4}$ alkenyl, C$_{2-4}$ alkynyl and C$_{1-4}$ haloalkyl;
R$^6$ and R$^7$, or R$^6$ and R$^8$, at each occurrence, together with the atom to which each is attached, are optionally combined to form a heterocyclyl;
R$^9$, at each occurrence, is independently selected from the group consisting of C$_{1-6}$ alkyl, C$_{2-6}$ alkenyl, C$_{2-6}$ alkynyl, and C$_{1-6}$ haloalkyl;
t is 1, 2, or 3;
m is 0, 1, 2, or 3;
n is 0, 1, 2, 3, 4, 5, or 6;
p is 0, 1, or 2;
Z$^1$ is aryl, heteroaryl, cycloalkyl, cycloalkenyl, heterocycloalkyl, or heterocycloalkenyl;
wherein Z$^1$ is unsubstituted or substituted with one or two or three or four or five independently selected R$^{10}$, OR$^{10}$, SR$^{10}$, S(O)R$^{10}$, SO$_2$R$^{10}$, C(O)R$^{10}$, C(O)OR$^{10}$, OC(O)R$^{10}$, NHR$^{10}$, N(R$^{10}$)$_2$, C(N)C(O)R$^{10}$, C(O)NHR$^{10}$, C(O)N(R$^{10}$)$_2$, C(O)NHOH, C(O)NHOR$^{10}$, C(O)NHSO$_2$R$^{10}$, NHC(O)R$^{10}$, NR$^{10}$C(O)R$^{10}$, NHC(O)OR$^{10}$, NR$^{10}$C(O)OR$^{10}$, NR$^{10}$C(O)NHR$^{10}$, NR$^{10}$C(O)N(R$^{10}$)$_2$, NHC(O)NH$_2$, NHC(O)NHR$^{10}$, NHC(O)N(R$^{10}$)$_2$, SO$_2$NH$_2$, SO$_2$NHR$^{10}$, SO$_2$N(R$^{19}$)$_2$, NHS(O)R$^{19}$, NHSO$_2$R$^{10}$, NR$^{10}$SO$_2$R$^{10}$, NHSO$_2$NHR$^{10}$, N(CH$_3$)SO$_2$N(CH$_3$)R$^{10}$, (O), NH$_2$, NO$_2$, N$_3$, OH, F, Cl, Br, I, CN, CF$_3$, OCF$_3$, CF$_2$CF$_3$, OCF$_2$CF$_3$, C(O)H, C(O)OH, C(N)NH$_2$, C(N)NHR$^{10}$, C(N)N(R$^{10}$)$_2$, CNOH, CNOCH$_3$, or C(O)NH$_2$ substituents;
R$^{10}$ is R$^{11}$, R$^{12}$, R$^{13}$ or R$^{14}$;
R$^{11}$ is aryl;
R$^{12}$ is heteroaryl;
R$^{13}$ is cycloalkyl, cycloalkenyl, cycloalkynyl, heterocycloalkyl or heterocycloalkenyl;
R$^{14}$ is alkyl, alkenyl or alkynyl, each of which is unsubstituted or substituted with one or two or three independently selected R$^{15D}$, NC(R$^{15A}$)(R$^{15B}$), R$^{15}$, OR$^{15}$, SR$^{15}$, S(O)R$^{15}$, SO$_2$R$^{15}$, NHR$^{15}$, N(R$^{15}$)$_2$, C(O)R$^{15}$, C(O)NH$_2$, C(O)NHR$^{15}$, C(O)N(R$^{15}$)$_2$, NHC(O)R$^{15}$, NR$^{15}$C(O)R$^{15}$, NHSO$_2$R$^{15}$, NHC(O)OR$^{15}$, SO$_2$NH$_2$, SO$_2$NHR$^{15}$, SO$_2$N(R$^{15}$)$_2$, NHC(O)NH$_2$, NHC(O)NHR$^{15}$, NHC(O)CH(CH$_3$)NHC(O)CH(CH$_3$)NH$_2$, NHC(O)CH(CH$_3$)NHC(O)CH(CH$_3$)NHR$^{15}$, OH, (O), C(O)OH, N$_3$, CN, NH$_2$, CF$_3$, CF$_2$CF$_3$, F, Cl, Br or I substituents;
R$^{15A}$ and R$^{15B}$ are independently selected alkyl or, together with the N to which they are attached, R$^{15C}$;
R$^{15C}$ is aziridin-1-yl, azetidin-1-yl, pyrrolidin-1-yl or piperidin-1-yl, each having one CH$_2$ moiety unreplaced or replaced with O, C(O), CNOH, CNOCH$_3$, S, S(O), SO$_2$ or NH;
R$^{15D}$ is C$_2$-C$_5$-spiroalkyl, each of which is unsubstituted or substituted with OH, (O), N$_3$, CN, CF$_3$, CF$_2$CF$_3$, F, Cl, Br, I, NH$_2$, NH(CH$_3$) or N(CH$_3$)$_2$;
R$^{15}$ is R$^{16}$, R$^{17}$, R$^{18}$ or R$^{19}$;
R$^{16}$ is aryl;
R$^{17}$ is heteroaryl;
R$^{18}$ is cycloalkyl, cycloalkenyl, heterocycloalkyl, or heterocycloalkenyl; and
R$^{19}$ is alkyl.
2. The compound of claim 1, or a therapeutically acceptable salt thereof, wherein X¹ is benzo[d]thiazolyl, thiazolo[5,4-b]pyridinyl, thiazolo[4,5-c]pyridinyl, imidazo[1,2-a]pyridinyl, thiazolo[5,4-c]pyridinyl, thiazolo[4,5-b]pyridinyl, imidazo[1,2-a]pyrazinyl, or imidazo[1,2-b]pyridazinyl, which are optionally substituted with one, two, three or four R⁴.

3. The compound of claim 1, or a therapeutically acceptable salt thereof, wherein
X¹ is

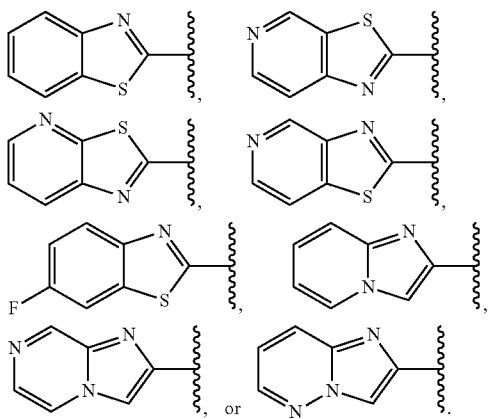

4. The compound of claim 3, or a therapeutically acceptable salt thereof, wherein

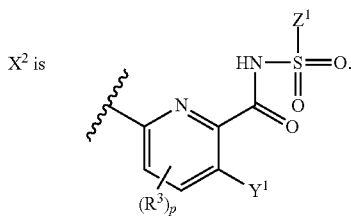

5. The compound of claim 3, or a therapeutically acceptable salt thereof, wherein
X² is

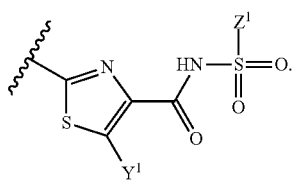

6. The compound of claim 4 or 5, or a therapeutically acceptable salt thereof, wherein
Y¹ is hydrogen.

7. The compound of claim 4 or 5, or a therapeutically acceptable salt thereof, wherein
Y¹ is (CH₂)ₜR⁵; R⁵ is aryl; and t is 1, 2, or 3.

8. The compound of claim 1, or a therapeutically acceptable salt thereof, wherein
Z¹ is unsubstituted or substituted phenyl.

9. The compound of claim 8, or a therapeutically acceptable salt thereof, wherein
Z¹ is substituted with NHR¹⁰ and SO₂CF₃, SO₂CF₂Cl, CF₃, NO₂, or F.

10. The compound of claim 1, or a pharmaceutically acceptable salt thereof, selected from the group consisting of
N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;
N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-(6-{[(4-{[(2R)-4-(morpholin-4-yl)-1-(phenyl sulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;
N-(1,3-benzothiazol-2-yl)-2-[6-[{(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide;
N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide;
N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide;
N-(1,3-benzothiazol-2-yl)-2-(4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-(5-benzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-(5-benzyl-4-{[(4-{[3-(dimethylamino)propyl]amino}-3-nitrophenyl)sulfonyl]carbamoyl}-1,3-thiazol-2-yl)-1,2,3,4-tetrahydroisoquinoline-8-carboxamide;
N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;
N-(1,3-benzothiazol-2-yl)-2-[4-{[(4-{[3-(dimethylamino)propyl]amino}-3-[(trifluoromethyl)sulfonyl]phenyl)sulfonyl]carbamoyl}-5-(2-phenylethyl)-1,3-thiazol-2-yl]-1,2,3,4-tetrahydroisoquinoline-8-carboxamide;
N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-[4-{[(4-{[3-(dimethylamino)propyl]amino}-3-nitrophenyl)sulfonyl]carbamoyl}-5-(2-phenylethyl)-1,3-thiazol-2-yl]-1,2,3,4-tetrahydroisoquinoline-8-carboxamide;
N-(1,3-benzothiazol-2-yl)-2-(4-{[(4-{[(2R)-4-hydroxy-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;
N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

N-(imidazo[1,2-a]pyridin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-a]pyridin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(imidazo[1,2-a]pyrazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-a]pyrazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(imidazo[1,2-b]pyridazin-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(imidazo[1,2-b]pyridazin-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(6-fluoro-1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide;

N-(6-fluoro-1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(4-{[(2R)-4-(dimethylamino)-1-(phenylsulfanyl)butan-2-yl]amino}-3-[(trifluoromethyl)sulfonyl]phenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(4-{[(2R)-4-(dimethylamino)-1-(phenylsulfanyl) butan-2-yl]amino}-3-[(trifluoromethyl)sulfonyl]phenyl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(4-{[(2R)-4-(dimethylamino)-1-(phenylsulfanyl) butan-2-yl]amino}-3-[(trifluoromethyl)sulfonyl]phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(1,3-benzothiazol-2-yl)-2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl] amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl] amino}phenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl] amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(3-{[chloro(difluoro)methyl]sulfonyl}-4-{[(2R)-4-(morpholin-4-yl)-1-(phenylsulfanyl)butan-2-yl] amino}phenyl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(3-{[chloro(difluoro)methyl]sulfonyl}-4-{[(2R)-4-(morpholin-4-yl)-1-(phenylsulfanyl)butan-2-yl] amino}phenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl] sulfonyl}carbamoyl)pyridin-2-yl]-N-([1,3]thiazolo[5,4-b]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl] sulfonyl}carbamoyl)-1,3-thiazol-2-yl]-N-([1,3]thiazolo[5,4-b]pyridin-2-yl)-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl] sulfonyl}carbamoyl)pyridin-2-yl]-N-([1,3]thiazolo[5,4-c]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl] sulfonyl}carbamoyl)-1,3-thiazol-2-yl]-N-([1,3]thiazolo[5,4-c]pyridin-2-yl)-1,2,3,4-tetrahydroisoquinoline-8-carboxamide;

2-[6-({[3-(methylsulfonyl)-4-{[(2R)-4-(morpholin-4-yl)-1-(phenylsulfanyl)butan-2-yl]amino}phenyl] sulfonyl}carbamoyl)pyridin-2-yl]-N-([1,3]thiazolo[4,5-c]pyridin-2-yl)-1,2,3,4-tetrahydroisoquinoline-8-carboxamide;

2-[4-({[3-(methylsulfonyl)-4-{[(2R)-4-(morpholin-4-yl)-1-(phenylsulfanyl)butan-2-yl]amino}phenyl] sulfonyl}carbamoyl)-1,3-thiazol-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[6-({[3-(methylsulfonyl)-4-{[(2R)-4-(morpholin-4-yl)-1-(phenylsulfanyl) butan-2-yl]amino}phenyl]sulfonyl}carbamoyl)pyridin-2-yl]-1,2,3,4-tetrahydroisoquinoline-8-carboxamide;

N-(imidazo[1,2-a]pyridin-2-yl)-2-[4-({[3-(methylsulfonyl)-4-{[(2R)-4-(morpholin-4-yl)-1-(phenylsulfanyl)

butan-2-yl]amino}phenyl]sulfonyl}carbamoyl)-1,3-thiazol-2-yl]-1,2,3,4-tetrahydroisoquinoline-8-carboxamide;

N-(imidazo[1,2-a]pyrazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-a]pyrazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(imidazo[1,2-b]pyridazin-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(imidazo[1,2-b]pyridazin-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(6-fluoro-1,3-benzothiazol-2-yl)-2-[6-({[3-(methylsulfonyl)-4-{[(2R)-4-(morpholin-4-yl)-1-(phenylsulfanyl)butan-2-yl]amino}phenyl]sulfonyl}carbamoyl)pyridin-2-yl]-1,2,3,4-tetrahydroisoquinoline-8-carboxamide;

N-(6-fluoro-1,3-benzothiazol-2-yl)-2-[4-({[3-(methylsulfonyl)-4-{[(2R)-4-(morpholin-4-yl)-1-(phenylsulfanyl)butan-2-yl]amino}phenyl]sulfonyl}carbamoyl)-1,3-thiazol-2-yl]-1,2,3,4-tetrahydroisoquinoline-8-carboxamide;

N-(1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

N-(6-fluoro-1,3-benzothiazol-2-yl)-2-(6-{[(3-fluoro-4-{[(2R)-4-(morpholin-4-yl)-1-(phenylsulfanyl)butan-2-yl]amino}phenyl)sulfonyl]carbamoyl}pyridin-2-yl)-1,2,3,4-tetrahydroisoquinoline-8-carboxamide;

N-(6-fluoro-1,3-benzothiazol-2-yl)-2-(4-{[(3-fluoro-4-{[(2R)-4-(morpholin-4-yl)-1-(phenylsulfanyl)butan-2-yl]amino}phenyl)sulfonyl]carbamoyl}-1,3-thiazol-2-yl)-1,2,3,4-tetrahydroisoquinoline-8-carboxamide;

N-(1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-b]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-b]pyridin-2-yl)-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[5,4-c]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[5,4-c]pyridin-2-yl)-1,2,3,4-tetrahydroisoquinoline-8-carboxamide;

2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-N-([1,3]thiazolo[4,5-c]pyridin-2-yl)-1,2,3,4-tetrahydroisoquinoline-8-carboxamide;

2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-N-([1,3]thiazolo[4,5-c]pyridin-2-yl)-1,2,3,4-tetrahydroisoquinoline-8-carboxamide;

N-(imidazo[1,2-a]pyridin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-a]pyridin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(imidazo[1,2-a]pyrazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-a]pyrazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(imidazo[1,2-b]pyridazin-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(imidazo[1,2-b]pyridazin-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(6-fluoro-1,3-benzothiazol-2-yl)-2-[6-({[4-{[(2R)-4-(morpholin-4-yl)-1-(phenylsulfanyl)butan-2-yl]amino}-3-(trifluoromethyl)phenyl]sulfonyl}carbamoyl)pyridin-2-yl]-1,2,3,4-tetrahydroisoquinoline-8-carboxamide;

N-(6-fluoro-1,3-benzothiazol-2-yl)-2-[4-({[4-{[(2R)-4-(morpholin-4-yl)-1-(phenylsulfanyl)butan-2-yl]amino}-3-(trifluoromethyl)phenyl]sulfonyl}carbamoyl)-1,3-thiazol-2-yl]-1,2,3,4-tetrahydroisoquinoline-8-carboxamide;

N-(1,3-benzothiazol-2-yl)-2-(6-{[(4-{[(2R)-4-(dimethylamino)-1-phenoxybutan-2-yl]amino}-3-nitrophenyl)sulfonyl]carbamoyl}pyridin-2-yl)-1,2,3,4-tetrahydroisoquinoline-8-carboxamide;

N-(1,3-benzothiazol-2-yl)-2-(4-{[(4-{[(2R)-4-(dimethylamino)-1-phenoxybutan-2-yl]amino}-3-nitrophenyl)sulfonyl]carbamoyl}-1,3-thiazol-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(4-{[(2R)-4-(dimethylamino)-1-phenoxybutan-2-yl]amino}-3-nitrophenyl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(4-{[(2R)-4-(dimethylamino)-1-phenoxybutan-2-yl]amino}-3-nitrophenyl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-1,2,3,4-tetrahydroisoquinoline-8-carboxamide;

N-(1,3-benzothiazol-2-yl)-2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-b]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-b]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[5,4-c]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[5,4-c]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-([1,3]thiazolo[4,5-c]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-([1,3]thiazolo[4,5-c]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyridin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyridin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-a]pyrazin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-a]pyrazin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(imidazo[1,2-b]pyridazin-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(imidazo[1,2-b]pyridazin-2-yl)-1,2,3,4-tetrahydroisoquinoline-8-carboxamide;

2-(6-{[(6-{[(2R)-4-(dimethylamino)-1-(phenylsulfanyl)butan-2-yl]amino}-5-nitropyridin-3-yl)sulfonyl]carbamoyl}pyridin-2-yl)-N-(6-fluoro-1,3-benzothiazol-2-yl)-1,2,3,4-tetrahydroisoquinoline-8-carboxamide;

2-(4-{[(6-{[(2R)-4-(dimethylamino)-1-(phenylsulfanyl)butan-2-yl]amino}-5-nitropyridin-3-yl)sulfonyl]carbamoyl}-1,3-thiazol-2-yl)-N-(6-fluoro-1,3-benzothiazol-2-yl)-1,2,3,4-tetrahydroisoquinoline-8-carboxamide;

N-(1,3-benzothiazol-2-yl)-2-(6-{[(4-{[(2R)-4-(morpholin-4-yl)-1-(phenylsulfanyl)butan-2-yl]amino}-3-nitrophenyl)sulfonyl]carbamoyl}pyridin-2-yl)-1,2,3,4-tetrahydroisoquinoline-8-carboxamide; and N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide.

11. The compound of claim 1, or a pharmaceutically acceptable salt thereof, selected from the group consisting of N-(1,3-benzothiazol-2-yl)-2-(4-{[(4-{[(2R)-4-(dimethylamino)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(6-{[(4-{[(2R)-4-(morpholin-4-yl)-1-(phenylsulfanyl)butan-2-yl]amino}-3-[(trifluoromethyl)sulfonyl]phenyl)sulfonyl]carbamoyl}pyridin-2-yl)-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-[(trifluoromethyl)sulfonyl]phenyl)sulfonyl]carbamoyl}-5-(3-phenylpropyl)pyridin-2-yl]-1,2,3,4-tetrahydroisoquinoline-8-carboxamide;

N-(1,3-benzothiazol-2-yl)-2-[6-{[(4-{[3-(dimethylamino)propyl]amino}-3-nitrophenyl)sulfonyl]carbamoyl}-5-(2-phenylethyl)pyridin-2-yl]-1,2,3,4-tetrahydroisoquinoline-8-carboxamide;

N-(1,3-benzothiazol-2-yl)-2-(4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(5-benzyl-4-{[(4-{[3-(dimethylamino)propyl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-(5-benzyl-4-{[(4-{[3-(dimethylamino)propyl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-(4-{[(4-{[(2R)-4-(morpholin-4-yl)-1-(phenylsulfanyl)butan-2-yl]amino}-3-nitrophenyl)sulfonyl]carbamoyl}-1,3-thiazol-2-yl)-1,2,3,4-tetrahydroisoquinoline-8-carboxamide;

N-(1,3-benzothiazol-2-yl)-2-([4-{[(4-{[3-(dimethylamino)propyl]amino}-3-[(trifluoromethyl)sulfonyl]phenyl)sulfonyl]carbamoyl}-5-(2-phenylethyl)-1,3-thiazol-2-yl]-1,2,3,4-tetrahydroisoquinoline-8-carboxamide;

N-(1,3-benzothiazol-2-yl)-2-(4-{[(4-{[(2R)-4-(dimethylamino)-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide;

N-(1,3-benzothiazol-2-yl)-2-[4-{[(4-{[3-(dimethylamino)propyl]amino}-3-nitrophenyl)sulfonyl]carbamoyl}-5-(2-phenylethyl)-1,3-thiazol-2-yl]-1,2,3,4-tetrahydroisoquinoline-8-carboxamide;

N-(1,3-benzothiazol-2-yl)-2-(4-{[(4-{[(2R)-4-hydroxy-1-(phenylsulfanyl)butan-2-yl]amino}-3-[(trifluoromethyl)sulfonyl]phenyl)sulfonyl]carbamoyl}-1,3-thiazol-2-yl)-1,2,3,4-tetrahydroisoquinoline-8-carboxamide; and N-(1,3-benzothiazol-2-yl)-2-[4-{[(4-{[3-(dimethylamino)propyl]amino}-3-nitrophenyl)sulfonyl]carbamoyl}-5-(3-phenylpropyl)-1,3-thiazol-2-yl]-1,2,3,4-tetrahydroisoquinoline-8-carboxamide.

12. A composition for treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, a lymphoid malignancy of T-cell or B-cell origin, melanoma, myelogenous leukemia, myeloma, oral cancer, ovarian cancer, non-small cell lung cancer, prostate cancer, small cell lung cancer or spleen cancer, said composition comprising an excipient and a therapeutically effective amount of a compound of claim 1 or a pharmaceutically acceptable salt thereof.

13. A method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, a lymphoid malignancy of T-cell or B-cell origin, melanoma, myelogenous leukemia, myeloma, oral cancer, ovarian cancer, non-small cell lung cancer, prostate cancer, small cell lung cancer or spleen cancer in a patient, said method comprising administering to the patient a therapeutically effective amount of a compound of claim 1, or a pharmaceutically acceptable salt thereof.

14. A method of treating bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, a lymphoid malignancy of T-cell or B-cell origin, melanoma, myelogenous leukemia, myeloma, oral cancer, ovarian cancer, non-small cell lung cancer, prostate cancer, small cell lung cancer or spleen cancer in a patient, said method comprising administering to the patient therapeutically effective amount of the compound of claim 1, or a pharmaceutically acceptable salt thereof, and a therapeutically effective amount of one additional therapeutic agent or more than one additional therapeutic agent.

* * * * *

UNITED STATES PATENT AND TRADEMARK OFFICE
CERTIFICATE OF CORRECTION

PATENT NO.       : 8,883,784 B2                                     Page 1 of 1
APPLICATION NO.  : 13/964556
DATED            : November 11, 2014
INVENTOR(S)      : Judd et al.

It is certified that error appears in the above-identified patent and that said Letters Patent is hereby corrected as shown below:

In the Claims

Column 127, line 17, claim 1: "is heteroaryl;" to read as --is heteroaryl--

Column 128, line 29, claim 1: "$SO_2N(R^{19})_2$," to read as --$SO_2N(R^{10})_2$,--

Column 128, line 30, claim 1: "$NHS(O)R^{19}$," to read as --$NHS(O)R^{10}$,--

Column 130, line 18, claim 10: "[{(4-" to read as --{[(4- --

Signed and Sealed this
Fifteenth Day of September, 2015

Michelle K. Lee
*Director of the United States Patent and Trademark Office*

```
                        SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: F-Bak Probe Peptide
<220> FEATURE:
<221> NAME/KEY: MOD_RES
<222> LOCATION: 1
<223> OTHER INFORMATION: Gly is modified with acetyl
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with NH2

<400> SEQUENCE: 1

Gly Gln Val Gly Arg Gln Leu Ala Ile Ile Gly Asp Lys Ile Asn Arg
1               5                   10                  15
```